US008188140B2

(12) United States Patent
Beatch et al.

(10) Patent No.: US 8,188,140 B2
(45) Date of Patent: *May 29, 2012

(54) USES OF ION CHANNEL MODULATING COMPOUNDS

(75) Inventors: Gregory N. Beatch, Vancouver (CA); Alan M. Ezrin, Miami, FL (US)

(73) Assignee: Cardiome Pharma Corp.

( * ) Notice: Subject to any disclaimer, the term of this patent is extended or adjusted under 35 U.S.C. 154(b) by 0 days.

This patent is subject to a terminal disclaimer.

(21) Appl. No.: 12/900,330

(22) Filed: Oct. 7, 2010

(65) Prior Publication Data

US 2011/0118329 A1    May 19, 2011

Related U.S. Application Data

(62) Division of application No. 11/947,679, filed on Nov. 29, 2007, now Pat. No. 7,820,712, which is a division of application No. 10/838,470, filed on May 3, 2004, now Pat. No. 7,345,086.

(60) Provisional application No. 60/559,405, filed on Apr. 1, 2004, provisional application No. 60/544,941, filed on Feb. 13, 2004, provisional application No. 60/528,251, filed on Dec. 8, 2003, provisional application No. 60/527,169, filed on Dec. 4, 2003, provisional application No. 60/526,911, filed on Dec. 3, 2003, provisional application No. 60/516,248, filed on Oct. 31, 2003, provisional application No. 60/516,486, filed on Oct. 31, 2003, provisional application No. 60/493,392, filed on Aug. 7, 2003, provisional application No. 60/467,159, filed on May 2, 2003.

(51) Int. Cl.
    *A61K 31/40*    (2006.01)
(52) U.S. Cl. ......................................... 514/424
(58) Field of Classification Search .................... 514/424
    See application file for complete search history.

(56) References Cited

U.S. PATENT DOCUMENTS

| 2,954,380 | A | 9/1960 | Shapiro et al. |
| 3,218,328 | A | 11/1965 | Shapiro et al. |
| 4,145,435 | A | 3/1979 | Szmuszkovicz |
| 4,179,501 | A | 12/1979 | Szmuszkovicz |
| 4,598,087 | A | 7/1986 | Horwell |
| 4,656,182 | A | 4/1987 | Horwell |
| 4,663,343 | A | 5/1987 | Horwell et al. |
| 4,855,316 | A | 8/1989 | Horwell et al. |
| 4,880,800 | A | 11/1989 | Wallis |
| 4,906,655 | A | 3/1990 | Horwell et al. |
| 5,019,588 | A | 5/1991 | Horwell et al. |
| 5,051,428 | A | 9/1991 | Horwell et al. |
| 5,059,620 | A | 10/1991 | Stout et al. |
| 5,492,825 | A | 2/1996 | Jan et al. |
| 5,506,257 | A | 4/1996 | MacLeod et al. |
| 5,637,583 | A | 6/1997 | MacLeod et al. |
| 5,670,335 | A | 9/1997 | Jan et al. |
| 5,728,535 | A | 3/1998 | Lester et al. |
| 5,734,021 | A | 3/1998 | Lester et al. |
| 5,750,537 | A | 5/1998 | Nomura et al. |
| 5,817,698 | A | 10/1998 | Brown et al. |
| 5,885,984 | A | 3/1999 | MacLeod et al. |
| 6,174,879 | B1 | 1/2001 | MacLeod et al. |
| 6,180,632 | B1 | 1/2001 | Myers et al. |
| 6,210,809 | B1 | 4/2001 | Okutomi et al. |
| 6,214,809 | B1 | 4/2001 | Fermini et al. ................. 514/75 |
| 6,451,819 | B2 | 9/2002 | Alanine et al. ................ 514/326 |
| 6,521,619 | B2 | 2/2003 | Link et al. .................. 514/237.2 |
| 6,649,603 | B2 | 11/2003 | Lum ........................ 514/210.01 |
| 6,979,685 | B1 | 12/2005 | Beatch et al. ............... 514/231.2 |
| 7,053,087 | B1 | 5/2006 | Beatch et al. ............... 514/237.8 |
| 7,057,053 | B2 | 6/2006 | Beatch et al. ................. 548/541 |
| 7,101,877 | B2 | 9/2006 | Bain et al. .................. 514/231.2 |
| 7,259,184 | B2 | 8/2007 | Beatch et al. ................. 514/424 |
| 7,345,086 | B2 | 3/2008 | Beatch et al. ................. 514/424 |
| 7,524,879 | B2 | 4/2009 | Beatch et al. ................. 514/424 |
| 7,820,712 | B2 | 10/2010 | Beatch et al. ................. 514/424 |
| 2007/0190156 | A1 | 8/2007 | Beatch et al. ................. 424/489 |
| 2008/0312309 | A1 | 12/2008 | Wheeler et al. ............... 514/424 |
| 2009/0041841 | A1 | 2/2009 | Beatch et al. ................. 424/465 |
| 2010/0056603 | A1 | 3/2010 | Beatch et al. ................. 514/424 |
| 2011/0207730 | A1* | 8/2011 | Bain et al. .................. 514/233.5 |

FOREIGN PATENT DOCUMENTS

| CA | 1234808 | 4/1988 |
| CA | 1235122 | 4/1988 |
| CA | 2004575 | 6/1990 |
| CA | 2058502 | 6/1993 |
| CA | 2172513 | 3/1995 |
| CA | 2240728 | 9/1997 |
| CA | 2008391 | 12/1997 |
| CA | 2289055 | 1/1999 |
| CA | 2268590 A1 | 10/2000 |
| CA | 2132841 | 3/2001 |
| DE | 2 259 260 | 6/1974 |
| DE | 2 658 401 | 7/1978 |
| DE | 3 517 901 | 12/1985 |
| EP | 0147085 A2 | 7/1985 |

(Continued)

OTHER PUBLICATIONS

Abstract of DE 2 259 260, Derwent World Patents Index, Jun. 6, 1974. Abstract of JP 02-270864, espacenet database, Nov. 5, 1990.
Adcock, J.J. et al., (2003) "RSD931, a novel anti-tussive agent acting on airway sensory nerves" Br J Pharm, 138:407-416.
Altria, Kevin D. et al., (2001) "Capillary Electrophoresis as a Routine Analytical Tool in Pharmaceutical Analysis" LCGC 19(9): 972-985.
Amin et al., (1996) "RPR 101821, a New Potent Cholesterol-lowering Agent: Inhibition of Squalene Synthase and 7-Dehydrocholesterol Reductase", Naunyn-Schmiedeberg's Arch Pharmacol 353:233-240.

(Continued)

Primary Examiner — Rebecca Anderson

(57) ABSTRACT

Methods, formulations, dosing regimes, and routes of administration for the treatment or prevention of arrhythmias, including the treatment or prevention of atrial fibrillation. In these methods, the disease or condition is treated or prevented by administering one or more ion channel modulating compounds to a subject, where the ion channel modulating compound or compounds produce specific plasma levels in the subject. The ion channel modulating compounds may be cycloalkylamine ether compounds, particularly cyclohexylamine ether compounds.

17 Claims, 21 Drawing Sheets

FOREIGN PATENT DOCUMENTS

| | | |
|---|---|---|
| EP | 0222533 A1 | 5/1987 |
| EP | 0147085 B1 | 3/1990 |
| EP | 0372466 A2 | 6/1990 |
| EP | 0380063 A1 | 8/1990 |
| EP | 0380063 B1 | 7/1993 |
| EP | 0552386 A1 | 7/1993 |
| EP | 0720605 BI | 12/2001 |
| HU | 215963 B | 2/1998 |
| JP | 02-270864 | 11/1990 |
| WO | WO 93/19056 | 9/1993 |
| WO | WO 94/07843 | 4/1994 |
| WO | WO 94/14435 | 7/1994 |
| WO | WO 95/08544 | 3/1995 |
| WO | WO 95/28155 | 10/1995 |
| WO | WO 96/18615 | 6/1996 |
| WO | WO 96/23894 | 8/1996 |
| WO | WO 97/32857 | 9/1997 |
| WO | WO 97/49680 | 12/1997 |
| WO | WO 99/02159 | 1/1999 |
| WO | WO 99/03468 | 1/1999 |
| WO | WO 99/11252 | 3/1999 |
| WO | WO 99/16431 | 4/1999 |
| WO | WO 99/50205 | 10/1999 |
| WO | WO 99/50225 | 10/1999 |
| WO | WO 00/47547 | 8/2000 |
| WO | WO 00/51981 | 9/2000 |
| WO | WO 01/96335 | 12/2001 |
| WO | WO 03/105756 | 12/2003 |
| WO | WO 2004/008103 | 1/2004 |
| WO | WO 2004/098525 | 11/2004 |
| WO | WO 2004/099137 | 11/2004 |

OTHER PUBLICATIONS

Bain et al., (1997) "Better Antiarrhythmics? Development of Antiarrhythmic Drugs Selective for Ischaemia-Dependent Arrhythmias", Drug Development Research 42:198-210.

Barret, T. D. et al., (1996) "Glibenclamide Possesses Transient, Ischaemia Selective Class III Antiarrhythmic Actions But does not Prevent Ischaemic Arrhythmias" BPS Proceedings 116P.

Barrett, T. D. et al., (1997) "A model of myocardial ischemia for the simultaneous assessment of electrophysiological changes and arrhythmias in intact rabbits" J Pharmacol Toxicol Methods, 37:27-36.

Barrett, T.D. (2000) "Ischaemia selectivity confers efficacy for suppression of ischaemia-induced arrhythmias in rats" Eur J Pharm, 398:365-374.

Barrett, T.D. et al., (1996) "Atypical Dose Response curves for Antiarrhythmic Drugs" BPS Proceedings 115P.

Barrett, Terrance D. (1997) "Ischemia Selective Electrophysiological and antiarrhythmic actions of RSD1019 in ischemic cardiac tissue" J Mol Cell Cardiol, pp. 197.

Barrett, Terrance D. et al., (2000) "RSD 1019 suppresses ischaemia-induced monophasic action potential shortening and arrhythmias in anaesthetized rabbits" Br J Pharm,131.405-414.

Beatch et al., (2002) "RSD1235 Selectively Prolongs Atrial Refractoriness and Terminates AF in Dogs with Electricially Remodeled Atria", Pharmacologist, 44(2) (Supplement I), A15: XIVth World Congress of Pharmacology: Meeting Abstracts.

Beatch, G. et al., "Effect of a Novel Anti-tussive Compound CP1 Against Citric Acid Induced Cough in Guinea-Pigs" Proc West Pharmacol Soc 2001.

Beatch, G. N. et al., "RSD1235, A Novel Atrial-Selective Antiarrhythmic Drug, Shows Rapid and Extensive Oral Absorption in Man" 12th International Congress on Cardiovascular Pharmacotherapy, May 7-10, 2003, Barcelona, Spain.

Beatch, G. N. et al., (2002) "Ventricular Fibrillation, and Uncontrolled Arrhythmia Seeking New Targets" Drug Develop Res 55: 45-52.

Beatch, G.N. et al., (1996) "Antihistamine-induced Ventricular Arrhythmias" BPS Proceedings 120P.

Beatch, G.N. et al., (1997) "Characterization of a Non-Human Primate Model of Drug-Induced Torsades De Pointes" Proc.West. Pharmacol. Soc., 40: 13-16.

Beatch, G.N. et al., (2002) "RSD1235 Selectively Prolongs Atrial Refractoriness and Terminates AF in Dogs with Electrically Remodeled Atria" PACE 24(Part II):698. Abstract 702.

Bian et al., (1998)"Effects of K-opioid receptor stimulation in the heart and the involvement of protein kinase C" Brit. J. Pharmacol. 124:600-606.

Billman, (2003) "RSD-1235 Cardiome", Current Opinion Investigational Drugs 4(3):352-354.

Boiadjiev et al., (1996) "pH-Sensitive Exciton Chirality Chromophore..Solvatochromic Effects on Circular Dichroism Spectra", Tetrahedron: Asymmetry 7(10):2825-2832.

Bowen et al., (1992)"Characterization of the enantiomers of cis-n-[2-(3,4-Dichlorophenyl)Ethyl]-N-Methyl-2-(1-Pyrrolidinyl)Cyclohexylamine (BD737 and BD738): Novel Compounds with High Affinity, Selectivity and Biological Efficacy at Sigma Receptors" J. Pharmacol. Exp. Ther. 262(1):32-40.

Cardiome Drug Effective for Heart Patients. Press Release Sep. 3, 2002, 3 pages.

Cardiome Pharma Completes Phase I Safety Study. New Release Transmitted by CNN Newswire, Jul. 30, 2001. 2 pages.

Cardiome Pharma Corp. Healthcare (Underweight) Company Report Dec. 12, 2002. 26 pages.

Cardiome Reports Dosing of First Patient in Pivotal Phase II Study. Press Release Jan. 17, 2002. 3 pages.

Cardiome Reports Oral Absorption of RSD1235 in Humans. News Release via Canada Newswire (2002).3 pages.

Clohs, L. et al., (2002) "Validation of a capillary electrophoresis assay for assessing the metabolic stability of verapamil in human liver microsomes" J Cap Elec & Microchip Tech. 007: 113-117.

Clohs, Lilian "Capillary Electrophoresis and its Applications in the Pharmaceutical Industry" Short Course: One Platform Fits Many Applications. CSC 2002 Short Course, 52 pages.

Clohs, Lilian "Capillary Electrophoresis as an Analytical Tool in the Drug Discovery Process" Presentation CE Symposium, Aug. 2000, 40 pages.

Clohs, Lilian "The Versatility of CE for Drug Pharmacokinetics and Metabolism Studies" Presentation CE Symposium, Aug. 2001, 46 pages.

Clohs, Lilian (2001) "Pharmacokinetics profiling of new drug candidates: a key process in drug discovery" 4(1): 6.

Clohs, Lilian et al., (2002) "CE Analysis of Propranolol in Human Serum Using Dynamic Capillary Coating" CE Currents: LCGC Europe, Reader Service 14, pp: 289-293.

Clohs, Lilian. "Bio-Analytical Applications of Capillary Electrophoresis in a Drug Discovery Setting" CSC Seminar Jun. 2002, 29 pages.

Clohs, Lilian. "CE and Drug Metabolism Studies: A Powerful Combination in Drug Discovery" CE Symposium Washington, DC, (Aug. 2002), 31 pages.

Crotti et al., (1998) "Synthesis and Ring-Opening Reactions of the Diastereoisomeric cis-and trans-Epoxides Derived from 3-(Benzyloxy)cyclopentene and 2-(Benzyloxy)-2,5-dyhydrofuran" Eur. J. Org. Chem. 8:1675-1686.

Crotti et al., "Regiochemical Control of the Ring-Opening of Epoxides by Means of Chelating Processes. Part 13. Synthesis and Ring-Opening Reactions of the Diastereoisomeric cis- and Transepoxides Derived From 3-(benzyloxy)cyclopentene and 2-(benzyloxy)-2, 5-dihydrofuran," Chemical Abstracts 129(17):662-663, abstract No. 216472k, Oct. 26, 1998.

De Costa, Brian R. (1990) "Synthesis and Evaluation of N-Substituted cis-N-Methy1-2-(1-pyrrolidinyl)cyclohexylamines as High Affinity σ Receptor Ligands. Identification of a New Class of Highly Potent and Selective σ Receptor Probes" J Med Chem, 33:3100-3110.

Doci, A. "Local Anesthetic Effects of Intradermal RSD921 in Healthy Subjects" Clin Pham & Therapeutics, 65(2): 177, Feb. 1999.

Duan, D. et al., (1993) "Potassium Channel Blocking Properties of Propafenone in Rabbit Atrial Myocytes" J Pharm Exp Ther 264(3): 1113-1123.

Ezrin et al., (2002) "Safety and Pharmaccokinetics of RSD1235, a Novel Atrial Fibrillation Converting Drug, in Health Volunteers", Abstracts: 11th Int. Congress Cardiovasc. Pharmacother. 16 Abstract P297.

Ezrin, Alan M. et al., (2002) "A Dose-Ranging Study of RSD1235, A Novel Antiarrhythmic Agent, In Healthy Volunteers" Pharmacologist, 44(2) (Supplement I), A15: XIVth World Congress of Pharmacology: Meeting Abstracts.

Ezrin, Alan M. et al., (2002) "Safety and Pharmacokinetics of RSD1235, a Novel Atrial Fibrillation Converting Drug, in Healthy Volunteers" Poster Presented at Int. Soc. of Cardiovascular Pharmacotherapy, Montreal, 2002.

Fedida, D. et al., (2002) " Kv1.5 is an Important Component of Repolarrizing K$^+$ Current in Canine Atrial Myocytes" Circulation Research Peer Review Plus Manuscript PDF, 38 pages.

Franciosi, Luigi G. et al., "Phase II Clinical Trial of RSD921 as a Local Anaesthetic in Patients Undergoing Venous Cannulation for Elective Treatment" 28th Annual ACCP Meet Abstract 32, pp. 977, Feb. 2000.

Franciosi, Sonia et al. (2001) "pH-dependent blocking actions of three novel antiarrhythmic compounds on K$^+$ and Na$^+$ currents in rat ventricular myocytes" Eur J Pharm, 425:95-107.

Franqueza, L. et al., (1998) "Effects of propafenone and 5-hydroxy-propafenone on hKv1.5 channels" Br J Pharm 125:969-978.

Friess et al., (1961) "Central Activity Evoked in the Cat by Cis-Trans Isomers of 1,2-Aminocyclohexanol Dervivatives" Taxicol. Appl. Pharmacol. 3:638-653.

Grant, (1998) "Mechanisms of Atrial Fibrillation and Action of Drugs Used in its Management", Am J Cardiol 82:43N-49N.

Halfpenny, Paul R. (1990) "Highly Selective k-Opioid Analgesics. 3. Synthesis and Structure-Activity Relationships of Novel N-[2-(1-Pyrrolidiny1)4- or -5-substituted-cyclohexyl]arylacetamide Derivatives" J Med Chem, 33:289-291.

Halfpenny, Paul R. et al., (1989) "Highly Selective k-Opioid Analgesics. 2. Synthesis and Structure-Activity Relationships of Novel N-[(2-Aminocyclohexyl)aryl]acetamide Derivatives" J Med Chem, 32:1620-1626.

Hayes, E. S. et al., (1996) "RSD992 Enhances Erection and Copulation in Rats and Erection in Primates" Int J Impotence Res, pp. 189, (Abstract P24).

Hayes, ES. Et al., (1997) "Actions of Arylpiperazines on Corpus Cavernosum Smooth Muscle In Vitro" Asia Pac J Pharmacol, 12:97-103.

Hayes, ES. et al., (1997) "Direct Actions of Arylpiperazines on Rabbit and Human Corpus Caversonal Smooth Muscle In Vitro" Asia Par J Pharmacol, Abstract S15.

Hesketh, J., et al., "Safety of RSD1235 in a rabbit purkinje fiber model", (XIVth World Congress of Phar.: Meeting Abstracts: Dec. 22, 2002.

Keefe, D. et al. (1981) "New Antiarrhythmic Drugs: Their Place in Therapy" Drugs 22:363-400.

Kertesz, R. et al., "The Electrophysiological and Antiarrhythmic Actions of RSD Analogs of U50,488H in Rats" Proc west Pharmacol Soc ab. 9 pages, 1994.

Lang, C. C. et al., (2000) "Clinical Evaluation of RSD921 as a Local Anaesthetic in Patients Undergoing Venous Connulation for Elective Treatment" Clin Pham & Therapeutics, pp. 142.

Lewis et al., (1995) "Enzyme inhibition during the conversion of squalene to cholesterol", Steroids 60:475-483.

Li, GR. et al., (1996) "Adrenergic Modulation of Ultrarapid Delayed Rectifier K$^+$ current in Human Atrial Myocytes" Circ. Res.78:903-915.

Malayev, A. A. et al., (1995) "Mechanism of Clofilium Block of the Human Kv1.5 Delayed Rectifier Potassium Channel" Mol Pharm 47:198-205.

Martens et al., (1989) "Einfache Synthese neuer anellierter Pyrrole", J. Synth. Org. Chem. 12:965-967.

Matyus et al., (1997) "Antiarrhythmic Agents: Current Status and Perspective", Medicinal Research Reviews 17(5):427-451.

McLarnon, J. et al., (1996) "Mixed Block of K and Na Currents by KC8851, A Structural of Tedisamil In Vitro and In Vivo Studies" BPS Proceedings 114P.

Moorman et al., (1986) "pK$_a$ Does Not Predict pH Potentiation of Sodium Channel Blockade by Lidocaine and W6211 in Guinea Pig Ventricular Myocardium[1]", The Journal of Pharmacology and Experimental Therapeutics 238(1):159-166.

Morisawa et al., "Preparation of Flourocarbocylic Nucleosides as Antitumor Agents," *Chemical Abstracts* 115(5):904-905, abstract No. 50215n, Aug. 5, 1991.

Nakahsima, H. et al., (2002) "Angiotensin II Type I Receptor Antagonist Prevents the Promotion of Atrial Fibrillation" Pace 24(Part II):698. Abstract 701.

Nattel et al., (1998) "Effects of the novel antiarrhythmic agent azimilide on experimental atrial fibrillation and atrial electrophysiologic properties", Cardiovascular Research 37:627-635.

Nattel et al., (2001) "P2362: RSD1235: a novel antiarrhythmic agent with a unique electrophysiological profile that terminates AF in dogs", Eur. Heart J 22(Suppl):448 (Abstract P2362).

Nattel, (1998) "Experimental evidence for proarrhythmic mechanisms of antiarrhythmic drugs", Cardiovascular Research 37:567-577.

Nattel, S. et al, "The role of channel opening in transient outward current block by quinidine, flecainide, and 4-aminopyridine in human atrial myocytes," Abstract No. Tu-Pos403, p. A209, 1994.

Nishi et al., (1985) "Studies on 2-Oxoquinoline Derivatives as Blood Platelet Aggregation Inhibitors. IV." Synthesis and Biological Activity of the Metabolites of 6-[4-(1-Cyclohexyl-1 H-5-tetrazolyl)butoxy]-2-oxo-1,2,3,4-tetrahydroquinoline (OPC-13013), Chem. Pharm. Bull 33(3):1140-1147.

Nortran Arrhythmia Drug Demonstrates Oral Bioavailability. New Release Transmitted by CNN Newswire, Jun. 21, 2001. 2 pages.

Orth et al., "Cyclopentane-1-amines," *Chemical Abstracts* 89(15):555, abstract No. 129113f, Oct. 9, 1978.

Orth, Peter et al., "The Novel AF Conversion Agent RSD1235 Preferentially Blocks a Late Component of the Human Heart (h1) Na$^+$ Current Active During Repolarization" EP abstracts Oct. 2003.

Pugsley and Goldin (1999) "Molecular analysis of the Na$^+$ channel blocking actions of the novel class I antiarrhythic" Br J Pharm, 127:9-18.

Pugsley, M.K. et al., "Electropharmacology of two new class 1 agents" Heart and Stroke Annual Conference, p. 12, 1995.

Pugsley, M.K. et al., (1998) "Sodium Channel-Blocking Properties of Spiradoline, a K Receptor Agonist, are Responsible for its Antiarrhythmic Action in the Rat" J Cardiovas Pharmacol, 32:863-974.

Pugsley, M.K. et al., (1999) "Are the arrhythmias due to myocardial ischaemia and infarction dependent upon the sympathetic system?" Cardiol Res, 43:830-831.

Ribeiro, W. et al., (2001) "Determination of RSD921 in human plasma by high-performance liquid chromatography-tandem mass spectrometry using tri-deuterated RSD921 as internal standard: application to a phase I clinical trial" J Mass Spectrom, 36:1133-1139.

Rich, T. C. et al. "Quinidine Block of the Human Cardiac hKv1.5 Channel in Inside-Out Patches" Abstract No. TU-Pos404, 1999.

Roden et al., (1996) "The Cardiac Ion Channels: Relevance to Management of Arrhythmias", Annu Rev. Med. 47:135-148.

Roy, D. et al., (2003) "RSD1235 Rapidly and Effectively Terminates Atrial Fibrillation" Eur Heart J.

Rynbrandt, Ronald H, et al., (1971) "Cis-1-[2-(p-Anisidinomethyl)cyclohexyl]piperidine and Related Compounds Oral Hypoglycemic Agents" J Med Chem, 14(10): 985-987.

Sanguinetti M. C. (1992) "Modulation of Potassium Channels by Antiarrhythmic and Antihypertensive Drugs" Hypertension 19(3):228-236.

Singh, (1998) "Antiarrhythmic Drugs: A Reorientation in Light of Recent Developments in the Control of Disorders of Rhythm", Am J Cardiol 81(6A):3D-13D.

Singh, (2003) "Atrial Fibrillation: Epidemiologic Considerations and Rationale for Conversion and Maintenance of Sinus Rhythm", J. Cardiovasc. Pharmacol. Ther. 8(Suppl 1):S13-S26.

Snyders, D. J. et al., (1993) "A Rapidly Activating and Slowly Inactivating Potassium Channel Cloned from Human Heart" J. Gen. Physiol. 101:513-542.

Snyders, D. J. et al., (1995) "Determinants of Antiarrhythmic Drug Action Electrostatic and Hydrophobic Components of Block of the Human Cardiac hKv1.5 Channel" Circ. Res. 77 (3):575-583.

Srilatha, B. et al., (1997) "Alterations in Rabbit Corpus Cavernosal Pharmacology by High Cholesterol Diet" Asia Par J Pharmacol, Abstract S15.

Steinbeck, G. (1992) "Proarrhythmische Wirkungen von Antiarrhythmika-theoretische und Klinische Aspekte" Z Kardiol. 81: Suppl. 4,139-143.

Tong, V. et al., (2001) "Determination of an arylether antiarrhythmic and its N-dealkyl metabolite in rat plasma and hepatic microsomal incubates using liquid chromatography-tandem mass spectrometry" J Chromatog B., 759:256-266.

Valenzuela, C. et al. (1997) "Comparative effects of nonsedating histamine $H_1$ receptor antagonists, ebastine and terfenadine, on human Kv1.5 channels" Eur J Pharm 326:257-263.

Valenzuela, C. et al., (1997) "Effects of Ropivacaine on a Potassium Channel (hKv1.5) Cloned from Human Ventricle" Anesthesiology 86:718-728.

Walker, J. A. (2002) "Antiarrhythmic Drug Development—Illusion and Disillusion" Drug Develop Res 55:1-2.

Walker, M. L. et al., (1996) "Determination of an arylacetamide antiarrhythmic in rat blood and tissues using reversed-phase high-performance liquid chromatography" J Chromatog B., 675:257-263.

Walker, M.L. et al., (1996) "Increased Electrophsiological Activity in Raised K and low pH Improves Antiarrhythmic efficacy for a group of morpholinocyclohexyl Derivatives" BPS Proceedings 118P.

Walker, Michael J.A. and Guppy, Leon J. "Targeting Ischemic Ventricular Arrhythmias" Cardiac Drug Development, pp. 175-201, 2002-2003.

Wang, Z. et al., (1995) "Effects of Flecainide, Quinidine, and 4-Aminopyridine on Transient Outward and Ultrarapid Delayed Rectifier Currents in Human Atrial Myocytes[1]" J Pharm Exp Ther.,272(1):184-196.

Wang. Z. et al., (1993) "Sustained Depolarization-Induced Outward Current in Human Atrial Myocytes" Circ. Res. 73:1061-1076.

Wat, J.Y.K. et al., "Effects of Arylbenzacetamides on Neuromuscular Preparation" Proc West Pharmacol Soc 1994.

Wolf, et al. (1998) "Impact of Atrial Fibrillation on Mortality Stroke, and Medical Costs" Arch Intern Med 158: 229-234.

Wong, Judy et al., "Protein Binding Study of AA5, A New Antiarrhythmic Drug" Poster Conference, Aug. 2000.

Wong, J. et al., "Capillary Electrophoresis Assay to Assess In Vitro Metabolic Stability of Novel Compounds in Human Liver Microsomes," AAPS Poster, Oct. 2001.

Yeola, S. W. et al., (1996) "Molecular Analysis of a Binding Site for Quinidine in a Human Cardiac Delayed Rectifier K+ Channel" Circ. Res. 78(6): 1105-1114.

Yong et al., (1997) "Low pKa Predicts Antiarrhythmic Efficacy in a Series of Aminocyclohexyl Esters" J. Mol. and Cell Cardiol. 29(6):A169.

Yong et al., (1999) "RSD1000: A novel antiarrhythmic agent with increased potency under acidic and high-potassium conditions" J. Pharm. Exp. Ther. 289(1):236-244.

Yong, S.L. et al. (1996) "RSD1000: A Novel Antiarrhythmic Agent with an Improved Therapeutic Index" BPS Proceedings 119P.

Yong, S.L. et al., (1996) "SAR Evidence that Antiarrhythmic Activity is Unrelated to Opioid Kappa Agonist Activity" BPS Proceedings 117P.

Zhang et al., (1997) "Inhibition of [$^3$H]-U69593 binding and the cardiac effects of U50, 488H by calcium channel blockers in the rat heart" Brit. J. Pharmacol. 120:827-832.

Zolotoy, Alexander B. et al., (2003) "Physicochemical Determinants for Drug Induced Blockade of HERG Potassium Channels: Effect of Charge and Charge Shielding" Curr Med Chem 1(3): 1-17.

Stevenson et al., Dec. 2, 2004, N. Engl. J. Med, 351; 23, 2437-2440.

Alzheimer's Disease Information Page [online], [retrieved on Oct. 3, 2006]. Retrieved from the Internet, URL; <http://www.ninds.nih.gov/disorders/alzheimersdisease/alzheimersdisease.htm>.

Pratt et al., Oral vernakalant (RSD1235-SR) prevents recurrence of atrial fibrillation following cardioversion, poster presented at the 2007 Heart Rhythm Society Annual Meeting (2007).

Wheeler et al., "Controlled Release Oral Formulations of Ion Channel Modulating Compounds and Related Methods for Preventing Arrhythmia," Office Action mailed Feb. 24, 2010, U.S. Appl. No. 12/114,652, filed May 2, 2008, 24 pages.

Beatch et al., "Ion Channel Modulating Compounds and Uses Thereof," Office Action mailed Oct. 18, 2006, U.S. Appl. No. 11/342,270, filed Jan. 27, 2006, 40 pages.

Beatch et al., "Ion Channel Modulating Compounds and Uses Thereof," Office Action mailed Jul. 1, 2008, U.S. Appl. No. 11/757,880, filed Jun. 4, 2007, 12 pages.

Beatch et al., "Ion Channel Modulating Compounds and Uses Thereof," Office Action mailed Apr. 16, 2008, U.S. Appl. No. 11/619,136, filed Jan. 2, 2007, 24 pages.

Beatch et al., "Ion Channel Modulating Compounds and Uses Thereof," Final Office Action mailed Nov. 20, 2008, U.S. Appl. No. 11/619,136, filed Jan. 2, 2007, 10 pages.

Beatch et al., "Electrophysiological Profile of RSD1235, A New Drug for Conversion of Atrial Fibrillation" AHA Scientific Sessions, Orlando, FL, Nov. 8-12, 2003, 1 page.

Plouvier et al., "Synthesis and Structure Activity Relationships of a Series of 2-Aminocyclohexyl . . . as Potential Ischaemia Selective Ventricular Antiarrhythmics" 85th CSC Conference & Exhibition, Vancouver, BC, Jun. 1-5, 2002, 1 page.

Pugsley et al., "A characterization of the antiarrhythmic and electrophysiological properties of RSD992, A novel arylpiperazine drug" XIVth World Congress of Pharmacology: Meeting Abstracts: Abstract 22.7, San Francisco, CA, Jul. 7-12, 2002, 1 page.

Beatch, Gregory N., et al., "Electrophysiological Profile of RSD1235, a New Drug for Conversion of Atrial Fibrillation," AHA Scientific Sessions, Nov. 8-12, 2003, Orlando FL, 1 page.

Plouvier, B., et al., "Synthesis and Structure Activity Relationships of a Series of 2-Aminocyciahexl . . . as Potential Ischaemia Selective Ventricular Antiarrhythmics," BMPS 994, 85th CSC Conference & Exhibition, Jun. 1-5, 2002, Vancouver B.C., 1 page.

Pugsley, M.K., et al., "A Characterization of the Antiarrythmic and Electrophysiological Properties of RSD992, a Novel Arylpiperazine Drug," XIVth World Congress of Pharmacology: Meeting Abstract 22.8, Jul. 7-12, 2002, San Fracisco CA, 1 page.

* cited by examiner

USES OF ION CHANNEL MODULATING COMPOUNDS

CROSS REFERENCES TO RELATED APPLICATIONS

This application is a divisional of U.S. application Ser. No. 11/947,679, filed Nov. 29, 2007, now issued as U.S. Pat. No. 7,820,712 on Oct. 26, 2010, which is a divisional of U.S. application Ser. No. 10/838,470, filed May 3, 2004, now issued as U.S. Pat. No. 7,345,086 on Mar. 18, 2008, which claims the priority benefit of the following patent applications: U.S. provisional patent application No. 60/467,159, filed May 2, 2003; U.S. provisional patent application No. 60/493,392, filed Aug. 7, 2003; U.S. provisional patent application No. 60/516,486, filed Oct. 31, 2003; U.S. provisional patent application No. 60/516,248, filed Oct. 31, 2003; U.S. provisional patent application No. 60/526,911, filed Dec. 3, 2003; U.S. provisional patent application No. 60/527,169, filed Dec. 4, 2003; U.S. provisional patent application No. 60/528,251, filed Dec. 8, 2003; U.S. provisional patent application No. 60/544,941, filed Feb. 13, 2004; and U.S. provisional patent application No. 60/559,405, filed Apr. 1, 2004. The contents of each of these patent applications is incorporated herein by reference in its entirety.

TECHNICAL FIELD

The methods and formulations described in this patent relate to the use of ion channel modulating compounds to treat or prevent arrhythmia and other diseases. Specific plasma level concentrations, dosage levels and other characterizations of ion channel modulating compounds used to treat or prevent arrhythmia and other diseases, and in particular atrial fibrillation, are described.

BACKGROUND

Cardiac arrhythmias often occur as complications to cardiac diseases such as myocardial infarction and heart failure. In serious cases, arrhythmias can cause sudden death.

Atrial flutter and atrial fibrillation are the most commonly sustained cardiac arrhythmias in clinical practice. In this patent we refer to atrial fibrillation as either "atrial fibrillation" or "AF." Currently, the development or exacerbation of AF often prompts emergency department (ED) presentations. The incidence of arrhythmias increases with age, and with the aging population in developed countries, the prevalence is expected to rise substantially over the next several decades. Overall, there are a variety of management strategies for acute atrial fibrillation and the outcomes are generally good; however, catastrophic events can occur as a result of atrial fibrillation such as congestive heart failure, thrombo-embolic phenomenon (particularly strokes), and serious adverse effects associated with treatment.

Treatment of arrhythmias such as atrial fibrillation is complex and aspects of care, especially the decision to control the ventricular rate vs. convert the arrhythmia, remain controversial. Conversion of atrial fibrillation to sinus rhythm is often attempted in the acute setting to improve symptoms and to prevent the detrimental hemodynamic effects that atrial fibrillation may have in some patients (e.g., valvular disease or left ventricular dysfunction). Early conversion of atrial fibrillation may also prevent the development of electrical remodeling and the embolic risks associated with intra-atrial thrombus formation. Electrical cardioversion is effective in restoring sinus rhythm but requires procedural sedation or anesthesia and is not successful in all cases.

Currently available converting agents have highly variable efficacy and several safety limitations associated with their use. In addition, placebo-controlled trials that establish the efficacy and safety of these pharmacological therapies for acute conversion are limited.

An efficacious, simple, and safe pharmacological alternative to existing methods of cardioversion would be a welcome development for patients with arrhythmias and their treating physicians.

SUMMARY

Described in this patent are methods, formulations, dosing regimes, and routes of administration for the treatment or prevention of various diseases or conditions, including arrhythmias, and particularly the treatment or prevention of atrial fibrillation. In these methods, the disease or condition is treated or prevented by administering one or more ion channel modulating compounds to a subject, where the ion channel modulating compound or compounds produce specific plasma levels in the subject. Also provided are methods for providing specified plasma levels of ion channel modulating compounds in a subject.

Various subjects to which the ion channel compound or compounds may be administered are described in detail in the Detailed Description section. In one version of the methods, the subject is a human subject.

Various formulations, routes of administration, and dosing regimes that may be used are described in detail in the Detailed Description section. In one version of the methods, the formulation is an intravenous formulation. In one version of the methods, the formulation is an oral formulation. The formulations may include one or more ion channel modulating compounds together with other optional components. The formulations may be administered in a variety of dosing regimes, including administering one or more formulations that may or may not be administered via the same route of administration. The formulations may also be delivered by repeat dosing and by substantially continuous dosing.

Regarding the levels of ion channel modulating compounds produced in the blood plasma by administration of the ion channel modulating compound or compounds, the plasma levels may be characterized using a variety of characterizations, including (1) that the characterization that the concentration is above some concentration level for some amount of time, (2) that the $C_{max}$ of the concentration profile is above some specified level or in some range of levels, (3) that the mean trough value is below some specified level or is in a range of levels, and (4) that the steady state value is below some specified level or is in a range of levels.

Examples of blood plasma level concentration profiles that may be produced using the methods described in this patent include those in which the concentration of the ion channel modulating compound or compounds (1) is greater than about 0.1 µg/ml for at least some time; (2) has a $C_{max}$ of greater than about 0.1 µg/ml; (3) has a $C_{max}$ of between about 0.3 µg/ml and about 20 µg/ml; (4) has a $C_{max}$ of between about 0.3 µg/ml and about 15 µg/ml; (5) is greater that about 0.1 µg/ml for a period of time of at least about 10 hours; (6) is greater that about 1.0 µg/ml for a period of time of at least about 2 hours; (7) has a mean trough concentration of less than about 20 µg/ml; (8) has a steady state concentration of less than about 20 µg/ml; (9) has a mean trough concentration of less than about 10 µg/ml; (10) has a steady state concentration of less than about 10 µg/ml; (11) has a mean trough concentration of between about 1 ng/ml and about 10 μg/ml; (12) has a mean trough concentration of between about 0.3 μg/ml and about 10 μg/ml; (13) has a steady state concentration of between about 0.3 μg/ml and about 10 μg/ml; (14) has a mean trough concentration of between about 0.3 μg/ml and about 3 μg/ml; (15) has a steady state concentration of between about 1 ng/ml and about 10 μg/ml; (16) has a steady state concentration of between about 0.3 μg/ml and about 3 μg/ml. The total ion channel modulating compound concentration may possess one or more of these characterizations.

In the methods of treating arrhythmias, including atrial fibrillation, the ion channel modulating compound or compounds are administered to the subject to produce a total ion channel modulating compound concentration that (1) is greater than about 0.1 μg/ml for at least some time; (2) has a $C_{max}$ of greater than about 0.1 μg/ml; (3) has a $C_{max}$ of between about 0.3 μg/ml and about 20 μg/ml; (4) has a $C_{max}$ of between about 0.3 μg/ml and about 15 μg/ml; (5) is greater that about 0.1 μg/ml for a period of time of at least about 10 hours; or (6) is greater that about 1.0 μg/ml for a period of time of at least about 2 hours. The total ion channel modulating compound concentration may possess one or more of these characterizations.

In the methods of preventing or postponing onset of arrhythmias, including atrial fibrillation, the ion channel modulating compound or compounds are administered to the subject to produce a total ion channel modulating compound concentration that (1) has a mean trough concentration of less than about 20 μg/ml; (2) has a steady state concentration of less than about 20 μg/ml; (3) has a mean trough concentration of less than about 10 μg/ml; (4) has a steady state concentration of less than about 10 μg/ml; (5) has a mean trough concentration of between about 0.3 μg/ml and about 10 μg/ml; (6) has a steady state concentration of between about 0.3 μg/ml and about 10 μg/ml; (7) has a mean trough concentration of between about 0.3 μg/ml and about 3 μg/ml; (8) has a steady state concentration of between about 0.3 μg/ml and about 3 μg/ml. The total ion channel modulating compound concentration may possess one or more of these characterizations.

Various ion channel modulating compounds that may be used in the methods provided in this patent are described in detail in the Detailed Description section. In one version the ion channel modulating compound may be a compound of formula

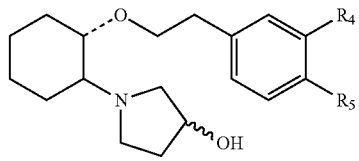

where $R_4$ and $R_5$ are independently selected from hydrogen, hydroxy and $C_1$-$C_6$alkoxy. In one version, the ion channel modulating compound is a monohydrochloride salt of the formula

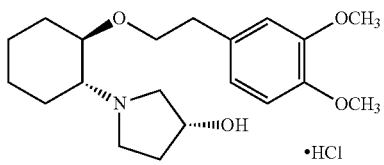

In one version, the ion channel modulating compound is a cycloalkylamine ether compound of formula

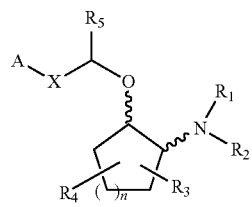

where n=1, 2, 3, or 4 and the other substituents are as defined in the Detailed Description section.

For all ion channel modulating compounds described above and elsewhere in this patent, isolated enantiomeric, diastereomeric and geometric isomers of the compounds may be used and mixtures of the compounds may be used. In addition, solvates or pharmaceutically acceptable salts of the compounds may be used.

Other aspects of the methods provided in this patent are described in detail in the Detailed Description section.

DETAILED DESCRIPTION

Figure 1:
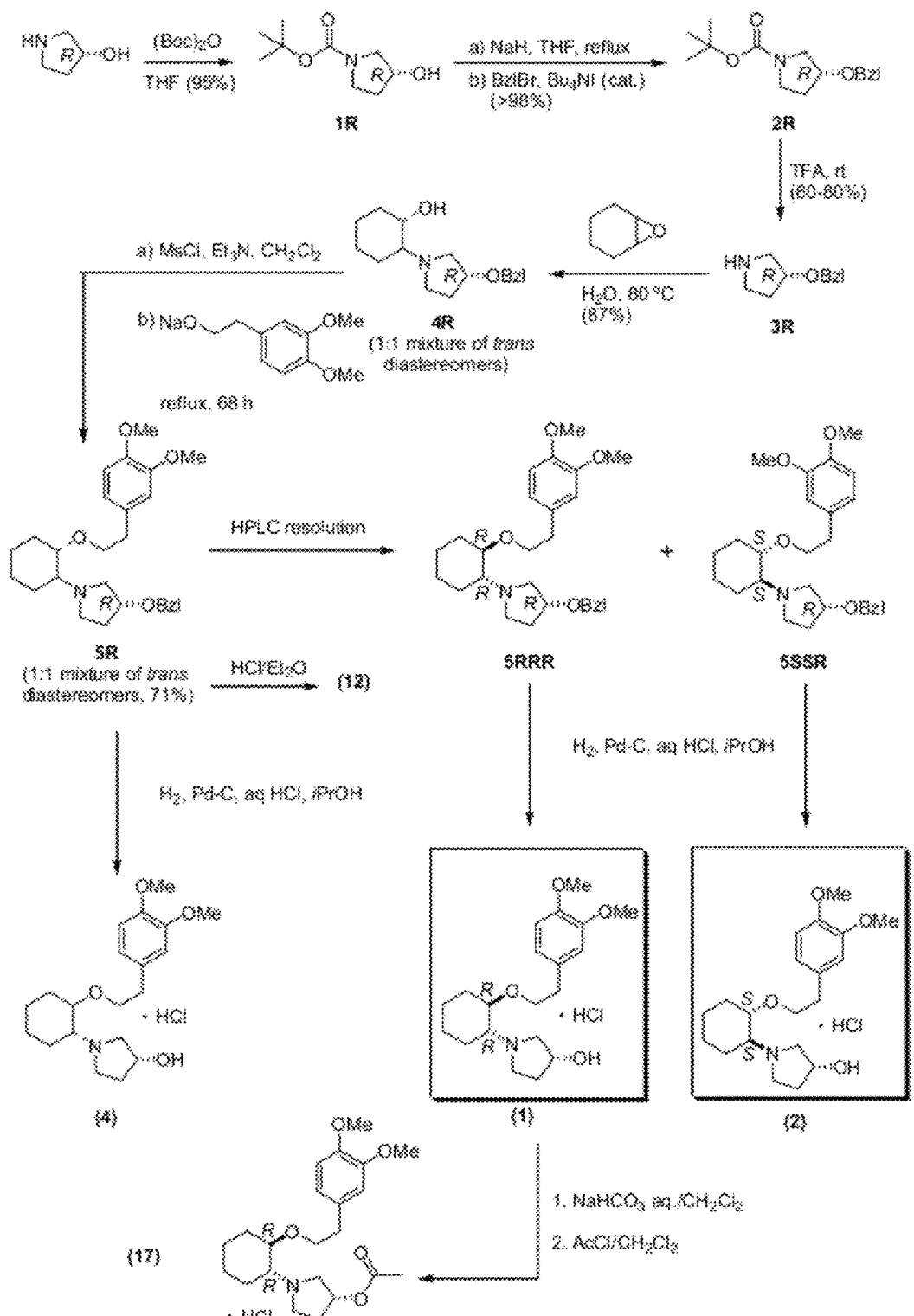
FIG. 1 illustrates a reaction sequence whereby certain aminocyclohexyl ether compounds of the present invention may be synthesized.

Described in this patent are methods, formulations and routes of administration for achieving a blood plasma level of an ion channel modulating compound in a subject. Also described in this patent are methods, formulations and routes of administration for treating a subject suffering from arrhythmia by achieving a blood plasma level. Also described are methods, formulations, and routes of administration for preventing or postponing onset of arrhythmia in a subject by achieving a blood plasma level.

Atrial fibrillation is one type of arrhythmia specifically referred to throughout this description. However the methods, formulations and routes of administration described herein are not limited to atrial fibrillation, and may be used to treat, prevent and/or postpone the onset of any arrhythmia, including but not limited to: ventricular arrhythmias (e.g., ventricular tachycardia, ventricular fibrillation, premature ventricular contractions), supraventricular arrhythmias (e.g., supraventricular tachycardia, atrial fibrillation, Wolff-Parkinson-White Syndrome, atrial flutter, premature supraventricular contractions), heart block, Long Q-T Syndrome, and sick sinus syndrome. It is also believed that the formulations and routes of administration described in this patent may be used to treat other diseases, which are described in this Detailed Description section.

Generally, the subject in which arrhythmia or other diseases may be treated or prevented is any mammal. In one version the subject is a human subject. In one version the subject is any domestic animal, including but not limited to dogs, and cats. In one version, the subject is any livestock animal, including but not limited to pigs, horses, cows and sheep. In one version, the subject is any zoo animal, including but not limited to: Bengel tigers, camels and giraffes.

In this Detailed Description, we first describe methods for treating arrhythmia (e.g. atrial fibrillation) and formulations and routes of administration that may be used in these methods. We then describe methods for preventing or postponing onset of arrhythmia and formulations and routes of administration that may be used in these methods. We then describe useful plasma levels and other diseases that it is believed may be treated using these plasma levels. We also describe specific compounds and general classes of compounds, and general formulations, routes of administration, and dosage forms that may be used in the methods described in this patent. We also present examples demonstrating the methods described in this patent.

Methods and Formulations for Treating Arrhythmia

In the treatment methods described in this section, a subject suffering from arrhythmia, including but not limited to atrial fibrillation, is treated by administering to the subject a formulation containing one or more ion channel modulating compounds. The formulation may optionally contain one or more additional components.

As used in this patent, unless the context makes clear otherwise, "treatment," and similar word such as "treated," "treating" etc, is an approach for obtaining beneficial or desired results, including and preferably clinical results. In the context of treatment of arrhythmia, treatment preferably means termination of arrhythmia. Treatment may also mean a return to normal sinus rhythm for the subject suffering from arrhythmia. Treatment may also mean a lessening of the severity of the arrhythmia. Treatment may include the use of the methods, formulations and routes of administration described herein in conjunction with other therapies, for example, electrical cardioversion.

In one version, the arrhythmia treated is atrial fibrillation.

Generally, the subject in which arrhythmia may be treated is any mammal. In one version, the subject is a human subject. In other versions the subject is a domestic animal, including but not limited to dogs and cats; or a farm animal, including but not limited to . . . .

Ion Channel Modulation Compounds that May be Used in the Methods of Treating Arrhythmia Generally, any ion channel modulating compound capable of treating arrhythmia (e.g. atrial fibrillation) may be used in the methods and formulations described in this section. Specific ion channel modulating compounds that may be used are described in the Ion Channel Modulating Compounds section of this patent, and generally any of the ion channel modulating compounds described in that section may be used.

In one version of the methods and formulations described in this section, the ion channel modulating compound is (1R, 2R)-2-[(3R)-hydroxypyrrolidinyl]-1-(3,4-dimethoxyphenethoxy)cyclohexane monohydrochloride.

Formulations and Routes of Administration that May be Used in the Methods of Treating Arrhythmia Generally, the formulation used for treating arrhythmia (e.g. atrial fibrillation) in the methods described in this patent can be a pure ion channel modulating compound, a mixture of one or more ion channel modulating compounds, a pure ion channel modulating compound formulated with one or more additional components, or a mixture of one or more ion channel modulating compounds formulated with one or more additional components. The ion channel modulating compound or compounds may generally be any of the compounds as described in the Ion Channel Modulating Compounds section of this patent.

Generally, any formulation, route of administration, and dosage form capable of being used in the methods for treating arrhythmia described in this patent may be used. General formulations, routes of administration, and dosage forms that may be used are described in the Formulations, Routes of Administration, and Dosage Forms section in the patent. Specific nonlimiting examples of formulations, routes of administration, and dosage forms that may be used for treating arrhythmia using the methods described in this patent are described in more detail below in this section.

In one nonlimiting example, the formulation is an oral dosage formulation or an intravenous dosage formulation. An example of a formulation that may be used for treating arrhythmia is an intra-venous formulation of one or more ion channel modulating compound in a pharmaceutically acceptable solution. The one or more ion channel modulating compound may generally be any ion channel modulating compound described in the Ion Channel Modulating Compounds section of this patent. A specific example of an ion channel modulating compound that may be used is (1R,2R)-2-[(3R)-hydroxypyrrolidinyl]-1-(3,4-dimethoxyphenethoxy)cyclohexane monohydrochloride.

One specific example of a formulation that may be used to treat arrhythmia by intravenous administration is a 20 mg/ml (1R,2R)-2-[(3R)-hydroxypyrrolidinyl]-1-(3,4-dimethoxyphenethoxy)cyclohexane monohydrochloride isotonic intravenous solution in 40 mM sodium Citrate, pH 5.5. Other preferred formulations include immediate (fast or "flash") release oral, sublingual, nasal, and inhaled formulations.

Amounts of Ion Channel Modulating Compounds and Dosing Regimes for Methods of Treating Arrhythmia Generally, the formulation used for treatment of arrhythmia (e.g. atrial fibrillation) will contain an amount of the one or more ion channel modulating compounds such that administration of a dose of the formulation containing a therapeutically effective amount of the ion channel modulating compound or compounds will treat the arrhythmia in the subject.

As used in this section, a "therapeutically effective amount" of the one or more ion channel modulating compounds is that amount sufficient to effect the desired treatment of arrhythmia in the subject to which the one or more ion channel modulating compounds are administered.

The formulation containing the therapeutically effective amount of the ion channel modulating compound or compounds may be administered in repeated doses. When administered as repeated doses, each individual does may or may not deliver a therapeutically effective amount of the ion channel modulating compound or compounds but the cumulative effect of the repeated doses will deliver a therapeutically effective amount of the ion channel modulating compound or compounds.

In one example for treating a human subject, the formulation is administered in a dose delivering between about 0.1 mg/kg and about 10 mg/kg of the ion channel modulating compound or compounds or compounds to the subject. In another version, the formulation is administered in a dose delivering between about 0.5 mg/kg and about 5 mg/kg of the ion channel modulating compound or compounds or compounds. As used in this patent, "mg/kg" means the amount of ion channel modulating compound or compounds per kg body weight of the subject. For example, but without limitation, to administer 0.1 mg/kg of ion channel modulating compound to a subject of mass 50 kg the administered dose contains 5 mg of ion channel modulating compound or compounds.

In other versions, the formulation is delivered by repeat dosing where a first dose delivers between about 0.1 mg/kg and about 10 mg/kg of ion channel modulating compound or compounds and a second dose delivers between about 0.1 mg/kg and about 10 mg/kg of ion channel modulating compound or compounds. These first two doses may optionally be followed by one or more subsequent doses. In other versions, the first dose delivers between about 0.1 mg/kg and 5.0 mg/kg of ion channel modulating compound or compounds and the second dose delivers between about 0.5 mg/kg and about 10 mg/kg of ion channel modulating compound or compounds; or the first dose delivers between about 1.0 mg/kg and about 5 mg/kg of ion channel modulating compound or compounds and the second dose delivers between about 1.0 mg/kg and about 5 mg/kg of ion channel modulating compound or compounds.

In the above repeated dosing examples the time between repeated dosing may generally be any time such that the repeated dosing delivers a therapeutically effective amount of the ion channel modulating compound or compounds. In one example, the time between repeated doses may be between about 5 minutes and about 1 hour, or in another version between about 15 minutes and about 45 minutes. In one version repeated doses of between about 0.01 mg/kg and about 10 mg/kg are delivered per hour for up to 36 hours.

Generally, repeated doses do not have to be administered via the same route of administration. For example, a first dose may be administered intravenously followed by a second dose administered orally. In addition, a therapeutically effective amount of the ion channel modulating compound or compounds may be delivered by administering more than one formulation at the same time. As a nonlimiting example, a therapeutically effective amount of the ion channel modulating compound or compounds may be delivered by simultaneous or near simultaneous administration of both oral and intravenous formulations.

Plasma Levels of Ion Channel Modulating Compounds in Methods of Treating Arrhythmias Generally the concentration of the ion channel modulating compound or compounds present in the subject blood plasma after administration will be at a level sufficient to effect the required treatment of the subject's arrhythmia.

As used in this patent, unless the context makes it clear otherwise, the blood plasma level is the concentration of the ion channel modulating compound or compounds in the blood plasma of the subject.

In one example in the treatment of a subject, the blood plasma level of the ion channel modulating compound or compounds has a $C_{max}$ of at least 0.1 μg/ml during and/or following administration of one or more doses of the formulation.

In another version, the blood plasma level of the ion channel modulating compound or compounds has a $C_{max}$ of between about 0.3 μg/ml and about 20 μg/ml during and/or following administration of one or more doses. In one version, the blood plasma level of the ion channel modulating compound or compounds has a $C_{max}$ of between about 0.3 µg/ml and about 15 µg/ml during and/or following administration of one or more doses.

In one example in the treatment of a subject, the blood plasma levels of the ion channel modulating compound or compounds is at least about 1 µg/ml for a time of about 2 hours during and/or following the administration of the first dose of formulation. In another version, the blood plasma level of the ion channel modulating compound or compounds is at least about 0.1 µg/ml for a time of about 10 hours during and/or following the administration of the first dose of the formulation. In one nonlimiting example, these blood plasma levels are maintained by administering two or more repeated doses of the specific intravenous formulation described above in this section.

Methods and Formulations for Preventing or Postponing Onset of Arrhythmia

In the prevention or postponement of onset of arrhythmia methods described in this section, a formulation containing one or more ion channel modulating compounds is administered to a subject to prevent or postpone onset of arrhythmia (e.g. atrial fibrillation) in the subject. Prevention and postponement of onset include prevention and postponement of onset of recurrence of arrhythmia; that is, the prevention or postponement of onset of arrhythmia in a subject that has previously undergone one or more arrhythmias. The formulation may optionally contain one or more additional components.

As used in this patent, unless the context makes clear otherwise, "prevention," and similar word such as "prevented," "preventing" etc, is an approach for obtaining beneficial or desired results, including and preferably clinical results. In the context of prevention of arrhythmia, prevention preferably means stopping the occurrence of arrhythmia. Prevention may also include not only an absolute stopping of the occurrence of arrhythmia but may also include a lessening of the severity of arrhythmia if it does occur. The methods described in this section may also be used to postpone the time for onset of arrhythmia if it does occur. The methods described in this section may also be used to lessen the probability that the subject will suffer from arrhythmia.

In one version the arrhythmia to be prevented is atrial fibrillation.

Generally, the subject in which arrhythmia may be prevented or for which onset may be postponed is any mammal. In one version, the subject is a human subject. In one version, the subject is any domestic animal, including, but not limited to cats, dogs, etc. In one version, the subject is any farm animal, including, but not limited to pigs, cows, horses, etc.

Ion Channel Modulation Compounds that May be Used in the Methods of Preventing or Postponing Onset of Arrhythmia Generally, any ion channel modulating compound capable of preventing or postponing onset of arrhythmia (e.g. atrial fibrillation) may be used in the methods and formulations described in this section. Specific ion channel modulating compounds that may be used are described in the Ion Channel Modulating section of this patent, and generally any of the ion channel modulating compounds described in that section may be used.

In one version of the methods and formulations described in this section, the ion channel modulating compound is (1R, 2R)-2-[(3R)-hydroxypyrrolidinyl]-1-(3,4-dimethoxyphenethoxy)cyclohexane monohydrochloride.

Formulations and Routes of Administration that May be Used in the Methods of Preventing or Postponing Onset of Arrhythmia Generally, the formulation used for preventing or postponing onset of arrhythmia in the methods described in this patent can be a pure ion channel modulating compound, a mixture of one or more ion channel modulating compounds, a pure ion channel modulating compound formulated with one or more additional components, or a mixture of one or more ion channel modulating compounds formulated with one or more additional components. The ion channel modulating compound or compounds may generally be any of the compounds as described in the Ion Channel Modulating Compounds section of this patent.

Generally, any formulation, route of administration, and dosage form capable of being used in the methods for preventing or postponing onset of arrhythmia described in this patent may be used. General formulations, routes of administration, and dosage forms that may be used are described in the Formulations, Routes of Administration, and Dosage Forms section in the patent. Specific nonlimiting examples of formulations, routes of administration, and dosage forms that may be used for preventing or postponing onset of arrhythmia using the methods described in this patent are described in more detail below in this section. In one nonlimiting example, the formulation is an oral dosage formulation.

An example of a formulation that may be used for preventing or postponing onset of arrhythmia is an oral dosage formulation of one or more ion channel modulating compound. The oral dosage formulation may be a solid formulation or may be a liquid formulation. The one or more ion channel modulating compound may generally be any ion channel modulating compound described in the Ion Channel Modulating Compounds section of this patent. A specific example of an ion channel modulating compound that may be used is (1R,2R)-2-[(3R)-hydroxypyrrolidinyl]-1-(3,4-dimethoxyphenethoxy)cyclohexane monohydrochloride.

One specific example of a formulation that may be used to prevent or postpone onset arrhythmia by oral administration is a controlled release (CR) formulation, described below.

Amounts of Ion Channel Modulating Compounds and Dosing Regimes for Methods of Preventing or Postponing Onset of Arrhythmia Generally, the formulation used for preventing or postponing onset of arrhythmia will contain an amount of the one or more ion channel modulating compounds such that administration of a dose of the formulation containing a therapeutically effective amount of the ion channel modulating compound or compounds will prevent or postpone onset of the arrhythmia in the subject. As used in this section, a "therapeutically effective amount" of the one or more ion channel modulating compounds is that amount sufficient to effect the desired prevention or postponement of onset of arrhythmia in the subject to which the one or more ion channel modulating compounds are administered.

The formulation containing the therapeutically effective amount of the ion channel modulating compound or compounds may be administered in repeated doses. When administered as repeated doses, each individual does may or may not deliver a therapeutically effective amount of the ion channel modulating compound or compounds but the cumulative effect of the repeated doses will deliver a therapeutically effective amount of the ion channel modulating compound or compounds or compounds.

In one example for preventing or postponing onset of arrhythmia in a human subject, the formulation is administered in a dose delivering between about 0.1 mg/kg and about 50 mg/kg per day of the ion channel modulating compound or compounds or compounds to the subject. In another version, the formulation is administered in a dose delivering between about 0.5 mg/kg and about 20 mg/kg per day of the ion channel modulating compound or compounds or compounds. In another version, the formulation is administered in a dose delivering between about 5.0 mg/kg and about 20 mg/kg per day of the ion channel modulating compound or compounds or compounds.

In other versions, the formulation is delivered by repeat dosing where a first dose delivers between about 0.1 mg/kg and about 10 mg/kg of the ion channel modulating compound or compounds or compounds and a second dose delivers between about 0.1 mg/kg and about 10 mg/kg of the ion channel modulating compound or compounds or compounds. These first two doses may optionally be followed by one or more subsequent doses. In other versions, the first dose delivers between about 0.1 mg/kg and 5.0 mg/kg of the ion channel modulating compound or compounds and the second dose delivers between about 0.5 mg/kg and about 10 mg/kg of the ion channel modulating compound or compounds or compounds; or the first dose delivers between about 1.0 mg/kg and about 3 mg/kg of the ion channel modulating compound or compounds or compounds and the second dose delivers between about 1.0 mg/kg and about 5 mg/kg of the ion channel modulating compound or compounds or compounds.

In the above repeated dosing examples the time between repeated dosing may generally be any time such that the repeated dosing delivers a therapeutically effective amount of the ion channel modulating compound or compounds. In one example, the time between repeated doses may be between about 5 minutes and about seven days, or in another version between about 1 hour and about 24 hours. In one version, the time between repeated doses is between about 4 hours and about every seven days, or in another version between about 8 hours and 24 hours. In one version the time between doses is about 12 hours.

Generally, repeated doses do not have to be administered via the same route of administration. For example, a first dose may be administered orally followed by a second dose administered intravenously. In addition, a therapeutically effective amount of the ion channel modulating compound or compounds may be delivered by administering more than one formulation at the same time. As a nonlimiting example, a therapeutically effective amount of the ion channel modulating compound or compounds may be delivered by simultaneous or near simultaneous administration of both oral and intravenous formulations.

Plasma Levels of Ion Channel Modulating Compounds in Methods of Preventing or Postponing Onset of Arrhythmia Generally the concentration of the ion channel modulating compound or compounds present in the subject blood plasma after administration will be at a level sufficient to effect the required prevention or postponement of onset of the subject's arrhythmia (e.g. atrial fibrillation).

In one example in the prevention or postponing onset of arrhythmia in a subject, the blood plasma level of the ion channel modulating compound or compounds has a $C_{max}$ of at least 50 ng/ml following administration of one or more doses of the formulation. In another version, the blood plasma level of the ion channel modulating compound or compounds has a $C_{max}$ of between about 50 ng/ml and about 50 $\mu$g/ml following administration of one or more doses. In other versions, the blood plasma level of the ion channel modulating compound or compounds following administration of one or more doses has a $C_{max}$ of between about 50 ng/ml and about 30 $\mu$g/ml; or between about 50 ng/ml and about 20 $\mu$g/ml; or between about 50 ng/ml and about 10 $\mu$g/ml; or between about 0.3 $\mu$g/ml and about 3 $\mu$g/ml; or between about 10 $\mu$g/ml and about 50 $\mu$g/ml; or between about 20 $\mu$g/ml and about 50 $\mu$g/ml; or between about 30 $\mu$g/ml and about 50 $\mu$g/ml.

In one example in the prevention or postponing onset of arrhythmia in a subject, the blood plasma levels of the ion channel modulating compound or compounds is at least about 0.1 $\mu$g/ml for a time of about 3 hours during and/or following the administration of the first dose of formulation. In one nonlimiting example, these blood plasma levels are maintained by administering one or more repeated doses of the oral formulation described above in this section.

Figure 18:
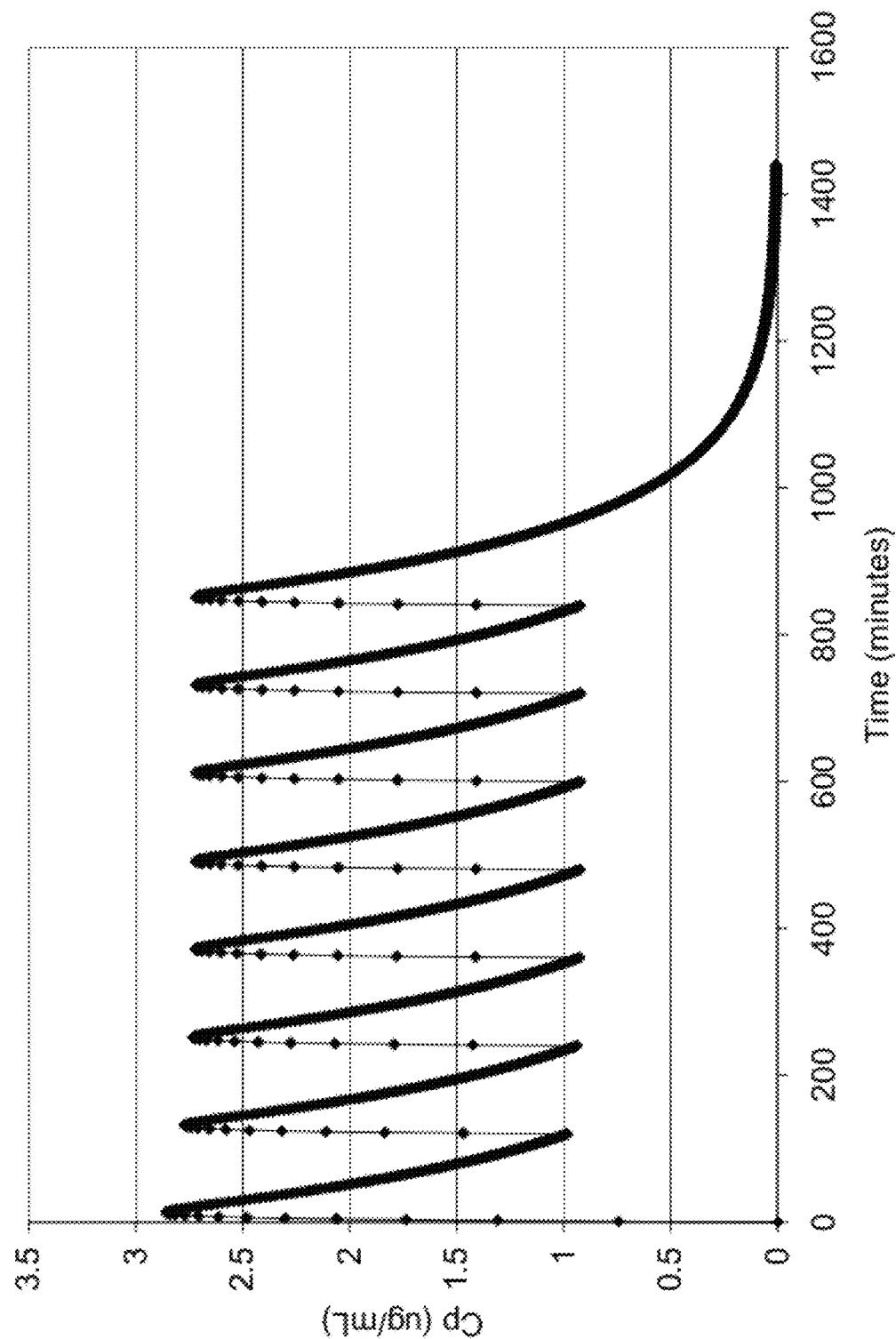
FIG. 18 shows a simulated pharmacokinetic profile for a multiple dosing regime of a loading dose of 150 mg followed by a maintenance dose of 100 mg given orally every two hours.

In one example in the prevention or postponing onset of arrhythmia in a subject, the blood plasma levels of the ion channel modulating compound or compounds has a mean trough value of between about 50 ng/ml and about 30 $\mu$g/ml. In another version, the mean trough value is between about 50 ng/ml and about 20 $\mu$g/ml. In another version, the mean trough value is between about 50 ng/ml and about 10 $\mu$g/ml. In another version, the mean trough value is between about 1 ng/ml to 10 $\mu$g/ml. In another version, the mean trough value is between about 0.3 $\mu$g/ml and about 3 $\mu$g/ml. As used herein, unless the context makes clear otherwise, the mean trough value is the average of the trough values for the blood plasma levels of the ion channel modulating compounds during a course of dosing; where the trough value is the lowest concentration of the ion channel modulating compound in the blood plasma immediately before a subsequent dose of the ion channel modulating compound. For example, but without limitation, the mean trough value for the course of closing illustrated in FIG. 18 is the average of the seven local minimum values of the blood plasma levels immediately preceeding doses two through eight of the ion channel modulating compounds.

In one version of the methods of treatment or methods of prevention, it may be possible to provide blood plasma levels by a continuous or substantially continuous delivery of the ion channel modulating compounds. In this situation, the characterization of the total concentration of ion channels modulating compounds by the mean trough levels is ambiguous since there are not a discrete number of doses with concomitant trough levels immediately preceding each dose. Instead, the continuous or substantially continuous delivery of ion channel modulating compound will provide, after some initial time, a steady state concentration of ion channel modulating compound or compounds. In this situation, the ranges of mean trough valves described for the multiple dosing regime is replaced by ranges for the steady state concentration. For example, in one version the steady state concentration is less than about 20 $\mu$g/ml. In another version, the steady state concentration is less than about 10 $\mu$g/ml. In another version, the steady state concentration is between 1 ng/ml and 10 $\mu$g/ml. In another version, the steady state concentration is between 0.3 $\mu$g/ml and 3 $\mu$g/ml.

Rates and Mechanism for Absorption of Ion Channel Modulating Compounds

In one version of the methods described in this patent, the ion channel modulating compound or compounds that are administered to a subject have a rate of absorption that is substantially independent of the site or route of administration. In one version, the rate of absorption of the ion channel modulating compound or compounds administered to a subject orally is approximately equivalent to the rate of absorption of the ion channel modulating compound or compounds administered in the duodenum of the subject. In one version, the rate of absorption of the ion channel modulating compound or compounds administered to a subject orally is approximately equivalent to the rate of absorption of the ion channel modulating compound or compounds administered in the colon of the subject. In one version, the rate of absorption of the ion channel modulating compound or compounds administered to a dog is substantially independent of the site or route of administration. In one version, the rate of absorption of the ion channel modulating compound or compounds administered to a dog orally is approximately equivalent to the rate of absorption of the ion channel modulating compound or compounds administered in the duodenum of the dog. In one version, the rate of absorption of the ion channel modulating compound or compounds administered to a dog orally is approximately equivalent to the rate of absorption of the ion channel modulating compound or compounds administered in the colon of the dog.

In one version of the methods described in this patent, following administration of the ion channel modulating compound or compounds to a subject, the blood plasma level of the ion channel modulating compound or compounds is substantially independent of the route of administration. In one version, the blood plasma level of the ion channel modulating compound or compounds following oral administration to the subject is substantially equivalent to the blood plasma level of the ion channel modulating compound or compounds following administration to the subject's colon. In one version, the blood plasma level of the ion channel modulating compound or compounds following oral administration to the subject is substantially equivalent to the blood plasma level of the ion channel modulating compound or compounds following administration to the subject's duodenum. In one version the subject is a dog.

As used herein, unless the context makes it clear otherwise, the rate of absorption of the ion channel modulating compound or compounds may be measured by the blood plasma level of the ion channel modulating compound or compounds over time. In one version, the rate of absorption of the ion channel modulating compound or compounds is measured by the area under the curve (AOC) of the blood plasma level of the ion channel modulating compound or compounds over time. In one version, the rate of absorption of the ion channel modulating compound or compounds is measured by the peak blood plasma level ($C_{max}$) of the ion channel modulating compound or compounds and the time after administration that the peak blood plasma level occurs ($T_{max}$).

As used in this patent, unless the context makes it clear otherwise, a second rate of absorption is substantially equivalent to a first rate of absorption if the value of the second rate of absorption is within about twenty percent of the value of the first rate of absorption, or within about ten percent of the value of the first rate of absorption, or within about five percent of the value of the first rate of absorption. As used in this patent, unless the context makes it clear otherwise, a second blood plasma level is substantially equivalent to a first blood plasma level if the value of the second blood plasma level is within about twenty percent of the value of the first blood plasma level, or within about ten percent of the value of the first blood plasma level, or within about five percent of the value of the first blood plasma level.

Methods for Producing Blood Plasma Levels of Ion Channel Modulating Compounds

Generally, described in this section are specific useful blood plasma levels of ion channel modulating compounds and methods of producing the levels. As described in the section above, the blood plasma levels of ion channel modulating compounds may be used to treat or prevent arrythmias including atrial fibrillation. However, it is also believed that the blood plasma levels of ion channel modulating compounds may be used to treat or prevent other diseases. Examples of diseases which it is believed may be treated are described in this section.

Useful blood plasma levels in a subject of ion channel modulating compounds in a subject include: (1) greater than about 0.1 μg/ml for at least some time; (2) $C_{max}$ greater than about 0.1 μg/ml; (3) $C_{max}$ between about 0.3 μg/ml and about 20 μg/ml; (4) $C_{max}$ between about 0.3 μg/ml and about 15 μg/ml; (5) greater that about 0.1 μg/ml for a period of time of at least about 10 hours; (6) greater that about 1.0 μg/ml for a period of time at least about 2 hours; (7) mean trough less than about 20 μg/ml; (8) steady state concentration less than about 20 μg/ml; (9) mean trough less than about 10 μg/ml; (10) steady state concentration less than about 10 μg/ml; (11) mean trough concentration between about 1 ng/ml and about 10 μg/ml; (12) mean trough concentration between about 0.3 μg/ml and about 10 μg/ml; (13) steady state concentration between about 0.3 μg/ml and about 10 μg/ml; (14) mean trough concentration between about 0.3 μg/ml and about 3 μg/ml; (15) steady state concentration between about 1 ng/ml and about 10 μg/ml; (16) steady state concentration between about 0.3 μg/ml and about 3 μg/ml.

The above blood plasma levels are useful when provided in a human subject. The above blood plasma levels are also useful when provided in a dog or pig subject. It is believed that the above blood plasma levels may also be useful when produced in other subjects such as those described elsewhere in this patent.

The blood plasma levels described in this section may be produced in a subject by administering to the subject one or more channel modulating compounds in an amount sufficient to produce the blood plasma levels described.

Generally, any formulations, routes of administration, and closing regimes capable of producing the blood plasma levels may be used. General examples of formulations routes of administration and dosages that may be used are described in the Formulations, Routes of Administration and Dosage section. Specific, nonlimiting formulations, routes of administration and dosage regimes that may be used to produce the blood plasma levels are described in the examples and in the method of treating and method of preventing sections above. With this information, together with their knowledge of the field, someone with knowledge of drug delivery technologies will be able to straightforwardly produce the described blood plasma levels in a subject.

As shown elsewhere in this patent, the blood plasma levels described in this section may be used to treat or prevent arrythmias, including but not limited to atrial fibrillation. It is also believed that the ion channel modulating compounds at the blood plasma levels described may also be used to treat or prevent other diseases including at least the following diseases and conditions: disease of the central nervous system (CNS disorders), Lou Gehrig's disease (Amyotrophic Lateral Sclerosis), Alzheimer, AIDS-related dementia, Multiple Sclerosis (MS), convulsion, seizures, epileptic spasms, depression, insomnia, anxiety, schizophrenia, Parkinson's disease, trigeminal pain, phantom limb pain, back pain, smoke cessation, respiratory disorders, cystic fibrosis, asthma, cough, inflammation and inflammatory disorders, irritable bowel disorders, irritable bowel syndrome Crohn's disease, prostatic hyperplasia, insect bites, psoriasis, arthritis, allergies, gastrointestinal disorders, urinary incontinence, cardio-vascular disorders, arrhythmia, heart failure, hypotension, cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, alopecia, diseases or dysfunctions of ion channels and receptors, diseases of voltage-gated ion channels, paralysis. This list is illustrative of the kinds of disorders for which the present invention could be used, and is not intended to be either limiting or exhaustive.

The methods and formulations described herein may be used for at least the following treatments: antitoxin, antivenom, antiviral, antibiotic, antiparasitic, antineoplastic, antinociceptive, sedative, anesthetic, analgesic, painkiller, painkiller, antipsychotic, local anaesthetic, topical anesthetic, antiangiogenic, cardioplegia, cardioprotectant.

For certain of the ion channel modulating compounds described in this patent application, the unique combination of activity with affect on the atria and devoid of or substantially devoid of similar effects on the ventricle leads to the development of an agent that may be used for the treatment and/or prevention of electrical rhythm disturbances in the atria without subsequent effects on the electrical activity in the ventricle.

The methods and ion channel modulating compounds described in this patent application are proposed for use in diseases and conditions including without limitation the management of atrial fibrillation, flutter and other supraventricular rhythm disturbance without adverse effects or substantial adverse effects on the electrical activity and rhythm of the ventricles.

In one version of the methods described in this patent application an ion channel modulating compound is administered to treat and/or prevent diseases and conditions including without limitation a host of supraventicular rhythm disturbances whilst not affecting or substantially affecting the ventricles and being a safer agent for patients with impaired LV function and useful for managing rate and rhythm disturbances in acute MI and CHF.

In one version of the methods described in this patent application an ion channel modulating compound is administered to treat and/or prevent diseases or conditions by modulating the late sodium current. The late sodium current may also be referred to as the persistent sodium current. In one version of the methods described in this patent application an ion channel modulating compound is administered to treat and/or prevent and/or diagnose diseases or conditions in which the late sodium current is enhanced. In one version of the methods described in this patent application an ion channel modulating compound is administered to treat and/or prevent and/or diagnose diseases or conditions in which the late sodium current is enhanced in skeletal muscle. In one version of the methods described in this patent application an ion channel modulating compound is administered to treat and/or prevent and/or diagnose congenital myotonia.

In one version of the methods described in this patent application an ion channel modulating compound is administered to treat and/or prevent acute rhythm disturbances in the heart under pathological conditions (i.e. acute ischemia) in which normal electrophysiology of the heart is altered and under which $I_{Kr}$ is of minimal importance and repolarization time course is dominated by $I_{to}$ and/or $I_{kur}$. In one embodiment, acute rhythm disturbances in the heart resulting from slowing conduction (e.g. reentrant arrhythmia under acute ischemia or other disease state) can be treated or prevented by reducing risks associated with alteration in cardiac rhythm. In one method described in this patent application, a therapeutically effective amount of a composition effective to treat and/or prevent and/or diagnose acute rhythm disturbances in the heart under pathological conditions is given to a patient in need thereof.

In one version of the methods described in this patent application an ion channel modulating compound is administered to treat and/or prevent rhythm disorders in the ischemic heart where such rhythm disturbances are mediated by prolonging refractoriness mediated by $I_{kur}$ and $I_{to}$ thusly prolonging the voltage time course of repolarization.

In one version of the methods described in this patent application an ion channel modulating compound is administered to treat and/or prevent rhythm disorders of the heart by inhibiting sodium currents of excitation and prolonging refractoriness mediated by $I_{kur}$ and $I_{to}$. In one method described in this patent application an ion channel modulating compound is administered to treat and/or prevent and/or diagnose rhythm disturbances by affecting abnormal conduction and prolonging the voltage time course of repolarization.

In one version of the methods described in this patent application an ion channel modulating compound is administered to treat and/or prevent rhythm disturbances by inhibiting sodium currents of excitation, inhibiting inward Na current associated with the plateau of the cardiac action potential (i.e. late window current) and prolonging refractoriness mediated by $I_{kur}$ and $I_{to}$. In one method described in this patent application an ion channel modulating compound is administered to treat and/or prevent and/or diagnose rhythm disturbances by affecting abnormal conduction and prolonging the voltage time course of repolarization.

In one version of the methods described in this patent application an ion channel modulating compound is administered to treat and/or prevent rhythm disorders in patients in need thereof wherein the ion channel modulating compound is used in conjunction with devices (i.e. pacemakers or implantable defibrillators) to facilitate the patients response to the device to restore normal rhythm and that are used to manage patients with rhythm disturbances.

In one version of the methods described in this patent application an ion channel modulating compound is administered to treat and/or prevent the early return of atrial fibrillation following electrical cardioversion. In one method described in this patent application an ion channel modulating compound is administered to treat and/or prevent and/or diagnose the early return of atrial fibrillation following electrical cardioversion to improve the ease of cardioversion in patients requiring transthroacic or internal cardioversion to restore normal rhythm.

In one version of the methods described in this patent application an ion channel modulating compound is administered to improve atrial contractility and/or to treat and/or prevent blood stasis via electrical stunning following a cardiac procedure. Examples of cardiac procedures include but are not limited to the maze procedure, surgery or cardiac bypasss, or any other procedure in which the atria are stunned precluding effective mechanical function leading to blood statsis, clotting, and potential of thromobosis.

In one version of the methods described in this patent application an ion channel modulating compound is administered to diagnose, treat and/or prevent electrical abnormalities of the heart in patients suffering from impaired electrical conduction of the heart.

In one version of the methods described in this patent application an ion channel modulating compound is administered to diagnose, treat and/or prevent contractile dysfunction and/or stunning of the atria. In one version of the methods described in this patent application an ion channel modulating compound is administered to reduce thrombosis, cardiac and cerebral ischemia due to atrial dyskenesis and clot formation in patients suffering from impaired electrical and mechanical function of the heart.

In one version of the methods described in this patent application an ion channel modulating compound is administered to treat and/or diagnose vasoconstriction. In one version of the methods described in this patent application an ion channel modulating compound is administered to treat and/or prevent vasoconstriction in patients with reduced blood flow based upon inhibition of $I_{to}$ and $I_{kur}$. In one version of the methods described in this patent application an ion channel modulating compound is administered to treat and/or prevent vasoconstriction by improving blood flood to selected organs and tissues.

In one version of the methods described in this patent application an ion channel modulating compound is administered to treat and/or prevent vasospasm. In one version of the methods described in this patent application an ion channel modulating compound is administered to improve respiratory function based upon relaxation of smooth muscle mediated by blockade of $I_{to}$ and $I_{kur}$ resulting in improvements in airway flow.

In one version of the methods described in this patent application an ion channel modulating compound is administered to treat and/or prevent smooth muscle spasm. In one version of the methods described in this patent application an ion channel modulating compound is administered to improve renal function and urinary flow based upon relaxation of smooth muscle mediated by blockade of $I_{to}$ and $I_{kur}$ resulting in improvements in urine flow. In one version of the methods described in this patent application an ion channel modulating compound is administered to improve gall bladder function and bile flow based upon relaxation of smooth muscle mediated by blockade of $I_{to}$ and $I_{kur}$.

In one version of the methods described in this patent application an ion channel modulating compound is administered to treat and/or prevent diseases or conditions which are mediated by inhibiting sodium currents and potassium currents. In one version of the methods described in this patent application an ion channel modulating compound is administered to treat and/or prevent diseases or conditions which are mediated by inhibiting sodium currents and potassium currents by inhibiting sodium channels and $I_{kur}$ and/or $I_{to}$. In one version of the methods described in this patent application an ion channel modulating compound is administered to improve smooth muscle contractile function in body structures associated with physiological processes. Example of such physiological processes include but are not limited to the passage of fluids and material through the body in the gut, urinary, respiratory or circulatory system for the reduction in blood pressure, intraocular pressure, humoral flow associated with glaucoma.

In one version of the methods described in this patent application an ion channel modulating compound is administered to treat and/or prevent diseases or conditions of the blood. In one version of the methods described in this patent application an ion channel modulating compound is administered to treat and/or prevent diseases or conditions of the blood by modifying $I_{kur}$ or $I_{to}$. Examples of diseases or conditions of the blood include but are not limited to sickle cell anemia and abnormal leukocyte or lymphochyte function (e.g. abnormal leukocyte or lymphochyte function associated with limiting an inflammation and/or immune response, particularly those mediated by changes in $I_{kur}$ or $I_{to}$).

In one version of the methods described in this patent application an ion channel modulating compound is administered to treat and/or prevent diseases or conditions of low flow ischemia, shock and/or reperfusion injury. In one version of the methods described in this patent application an ion channel modulating compound is administered to treat and/or prevent diseases or conditions of low flow ischemia, shock and/or reperfusion injury by inhibiting sodium currents and potassium currents mediated by $I_{kur}$ and $I_{to}$.

In one version of the methods described in this patent application an ion channel modulating compound is provided as an enzyme modulator. Enzyme that may be modulated (inhibited or activated) may include but are not limited to lactate dehydrogenase (LDH); kinases such as map kinases and other kinases; transaminase; ATPase; xanthine oxidase; and Cytochrome oxidase.

In one version of the methods described in this patent application an ion channel modulating compound is provided as an anti-helminthic or vermifuge, i.e. de-worming medication for human or other mammals.

In one version of the methods described in this patent application an ion channel modulating compound is administered to influence heart rate or rhythm. In one version of the methods described in this patent application an ion channel modulating compound is administered to influence heart rate or rhythm in the normal heart. In one version of the methods described in this patent application an ion channel modulating compound is administered to influence heart rate or rhythm in the diseased heart.

In one version of the methods described in this patent application an ion channel modulating compound is used as a research tool or diagnostic tool. In one version of the methods described in this patent application an ion channel modulating compound is used as a research tool or diagnostic tool by modulating $I_{to}$ and $I_{kur}$ and $I_{Na}$. In one version of the methods described in this patent application an ion channel modulating compound is used as a research tool or diagnostic tool based on its association with the protein or molecules mediating $I_{to}$ and $I_{kur}$ and $I_{Na}$. In one version of the methods described in this patent application an ion channel modulating compound is used as a ligand or affinity probe for proteins or molecules (i.e. ion channels). In one version of the methods described in this patent application an ion channel modulating compound is used as a research tool or diagnostic tool to create antibodies.

In one version of the methods described in this patent application an ion channel modulating compound is used as a research tool or diagnostic tool to identify cellular or subcellular processes associated with cardiac function. In one version of the methods described in this patent application an ion channel modulating compound is used as a research tool or diagnostic tool to identify receptor function and/or signal transduction. In one version of the methods described in this patent application an ion channel modulating compound is used as a research tool or diagnostic tool to identify mechanisms associated with disease of the body (such as cardiac disorders).

Ion Channel Modulating Compounds

In this section are described various compounds and classes of compounds that may be used as ion channel modulating compounds in the methods, formulations, etc. described in this patent.

In this section are first described a series of specific classes of ion channel modulating compounds together with specific example compounds, followed by a general description of compounds that may be used as ion channel modulating compounds.

Specific Classes of Ion Channel Modulating Compounds and Exemplary Ion Channel Modulating Compounds Examples of specific classes of ion channel modulating compounds and exemplary ion channel modulating compounds are described below and in U.S. provisional patent application No. 60/516,248, U.S. patent application Ser. No. 10/674,684, and U.S. patent application Ser. No. 09/913,373, each of which applications is incorporated herein by reference in its entirety.

In the variations described in this section on Specific Classes of Ion Channel Modulating Compounds and Exemplary Ion Channel Modulating Compounds, all enantiomeric and diastereomeric forms of the ion channel modulating compounds are intended. Pure stereoisomers, mixtures of enantiomers and/or diastereomers, and mixtures of different ion channel modulating compounds are described. Thus, the ion channel modulating compounds may occur as racemates, racemic mixtures and as individual diastereomers, or enantiomers with all isomeric forms being included in the present invention. A racemate or racemic mixture does not imply a 50:50 mixture of stereoisomers. Where a given structural formula or chemical name is presented for a compound it is intended that all possible solvates, pharmaceutically acceptable salts, esters, amides, complexes, chelates, stereoisomers, geometric isomers, crystalline or amorphous forms, metabolites, metabolic precursors or prodrugs of the compound are also separately described by the chemical structural formula or chemical name.

As used in this patent, unless the context make plain otherwise, the following terms are defined to have following meanings:

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Acyl" refers to branched or unbranched hydrocarbon fragments terminated by a carbonyl —(C=O)— group containing the specified number of carbon atoms. Examples include acetyl[$CH_3C=O—$, a $C_2$acyl] and propionyl [$CH_3CH_2C=O—$, a $C_3$acyl].

"Alkanoyloxy" refers to an ester substituent wherein the ether oxygen is the point of attachment to the molecule. Examples include propanoyloxy[($CH_3CH_2C=O—O—$, a $C_3$alkanoyloxy] and ethanoyloxy[$CH_3C=O—O—$, a $C_2$alkanoyloxy].

"Alkoxy" refers to an O-atom substituted by an alkyl group, for example, methoxy[-$OCH_3$, a $C_1$alkoxy].

"Alkoxyalkyl" refers to a alkylene group substituted with an alkoxy group. For example, methoxyethyl [$CH_3OCH_2CH_2—$] and ethoxymethyl($CH_3CH_2OCH_2—$] are both $C_3$alkoxyalkyl groups.

"Alkoxycarbonyl" refers to an ester substituent wherein the carbonyl carbon is the point of attachment to the molecule. Examples include ethoxycarbonyl[$CH_3CH_2OC=O—$, a $C_3$alkoxycarbonyl] and methoxycarbonyl[$CH_3OC=O—$, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene[-$CH_2CH_2CH_2—$, a $C_3$alkylene].

"Alkylcarboxy" refers to a branched or unbranched hydrocarbon fragment terminated by a carboxylic acid group [—COOH]. Examples include carboxymethyl [HOOC—$CH_2—$, a $C_2$alkylcarboxy] and carboxyethyl[HOOC—$CH_2CH_2—$, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2—$, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7—$), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing an hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S—$, a $C_1$thioalkyl).

"Modulating" in connection with the activity of an ion channel means that the activity of the ion channel may be either increased or decreased in response to administration of a compound or composition or method of the present invention. Thus, the ion channel may be activated, so as to transport more ions, or may be blocked, so that fewer or no ions are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

Aminocyclohexyl Ether Ion Channel Modulating Compounds

One class of compounds that are ion channel modulating compounds are compounds that comprise an aminocyclohexyl ether core structure having an ether oxygen atom at position 1 of a cyclohexane ring, and an amine nitrogen atom at position 2 of the cyclohexane ring. This core structure is shown below, with other positions numbered in corresponding order:

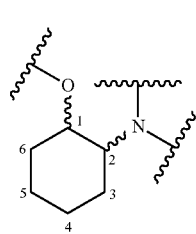

(A)

The bonds from the cyclohexane ring of A to the 1-oxygen and 2-nitrogen atoms in the above formula may be relatively disposed in either a cis or trans relationship. In one variation, the stereochemistry of the amine and ether substituents of the cyclohexane ring is either (R,R)-trans or (S,S)-trans. In another variation, the stereochemistry at these positions is either (R,S)-cis or (S,R)-cis.

In one version of the amino cyclohexyl ether ion channel modulating compounds, the ion channel modulating compound is a compound of the formula:

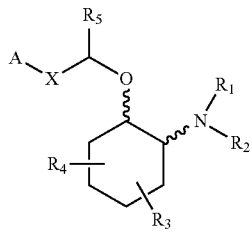

(I)

Compounds of formula (I) are aminocyclohexyl ethers. More specifically, these aminocyclohexyl ethers are substituted at position 2 of the cyclohexyl ring with an amine group —$NR_1R_2$. The cyclohexyl ring may also be substituted with additional substituents (designated as $R_3$ and $R_4$) as described in more detail below. Examples of specific compounds represented by formula (I) are described below.

Depending upon the selection of substituents $R_1$ and $R_2$, the compounds of formula (I) may be primary, secondary, or tertiary amines (i.e., both $R_1$ and $R_2$ are hydrogen, only one of $R_1$ and $R_2$ is hydrogen, or neither of $R_1$ and $R_2$ are hydrogen, respectively). In one embodiment of the invention, the compounds of formula (I) are tertiary amines, i.e., neither $R_1$ nor $R_2$ is hydrogen. Where the amine is tertiary, it may be a cyclic amine. Amine substituents $R_1$ and $R_2$ may be independently selected from substituents which include hydrogen, alkyl groups containing from one to eight carbon atoms (i.e., $C_1$-$C_8$alkyl), alkoxyalkyl groups containing from three to eight carbon atoms (i.e., $C_3$-$C_8$alkoxyalkyl), alkyl groups containing from one to eight carbon atoms where one of the carbon atoms is substituted with a hydroxyl group (i.e., $C_1$-$C_8$hydroxyalkyl), and aralkyl groups containing from seven to twelve carbon atoms (i.e., $C_7$-$C_{12}$aralkyl). In one version, $R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl. In another version, $R_1$ and $R_2$ are independently selected from $C_3$-$C_8$alkoxyalkyl, $C_1$-$C_8$hydroxyalkyl, and $C_7$-$C_{12}$aralkyl.

Alternatively, $R_1$ and $R_2$, when taken together with the nitrogen atom to which they are directly attached in formula (I), may form a ring denoted by formula (II):

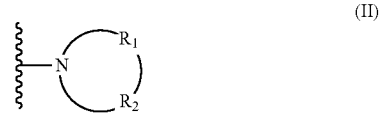

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur (e.g., an acetal, thioacetal, ketal, or thioketal group); and any two adjacent additional carbon ring atoms may be fused to a $C_3$-$C_8$-carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl. Examples of substituents containing a fused ring system include the perhydroindolyl and 1,2,3,4-tetrahydroisoquinolinyl groups.

In connection with the ring of formula (II), any two adjacent ring atoms may be joined together by single or double bonds. Thus, the ring of formula (II) may be saturated or unsaturated, and an unsaturated ring may contain one, or more than one, sites of unsaturation. In other words, the ring of formula (II) may contain one or more double bonds, it being understood, however, that the unsaturated ring of formula (II) is chemically stable.

Alternatively, $R_1$ and $R_2$, when taken together with the 2-amino nitrogen of formula (I), may complete a bicyclic ring. Bicyclic rings include, for example, 3-azabicyclo[3.2.2] nonane, 2-azabicyclo[2.2.2]octane, 3-azabicyclo[3.1.0]hexane, and 3-azabicyclo[3.2.0]heptane. For these derivatives, the 2-substituents of the cyclohexyl ethers of formula (I) are the following groups: 3-azabicyclo[3.2.2]nonan-3-yl, 2-azabicyclo-[2.2.2]octan-2-yl, 3-azabicyclo[3.1.0]hexan-3-yl, and 3-azabicyclo[3.2.0]heptan-3-yl.

$R_1$ and $R_2$, when taken together may contain only a single heteroatom. Preferred heteroatoms include nitrogen, oxygen and sulfur. An example of a ring in which $R_1$ and $R_2$ together include an oxygen heteroatom is the morpholinyl group. An example of a ring where $R_1$ and $R_2$ together include a second nitrogen heteroatom is the piperazinyl group.

Cyclohexane substituents $R_3$ and $R_4$ may be independently attached to ring positions 3, 4, 5 or 6 (i.e., both $R_3$ and $R_4$ may be attached to the same ring position or each attached to different ring positions). $R_3$ and $R_4$ are independently selected from hydrogen, hydroxy, $C_1$-$C_6$alkyl, and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur. Preferred heterocyclic substituents contain either a single oxygen or a single sulfur ring atom.

Depending upon the identity of X, the ether side chain, —CH($R_5$)—X-A, in formula (I) may take several forms. For example, a compound of formula (I) may have X as a —C($R_6$,$R_{14}$)—Y— group, where Y may be any of a direct bond, an oxygen atom (O), a sulfur atom (S) or a $C_1$-$C_4$alkylene group. $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl. Thus, compounds of the invention include compounds of formula (I) where $R_6$ and $R_{14}$ are hydrogen and Y is a direct bond, such that X may be $CH_2$.

Alternatively, X may be an alkenylene moiety, e.g., a cis- or trans-alkenylene moiety, C($R_{13}$)=CH, where $R_{13}$ may be any of hydrogen, $C_1$-$C_6$alkyl, $C_3$-$C_8$cycloalkyl, aryl or benzyl. For compounds of formula (I) where X is an alkenylene moiety, X is preferably a trans-alkenylene moiety.

Alternatively, X may be a direct bond. Independent of the selections for A, X and other variables, $R_5$ is selected from hydrogen, $C_1$-$C_6$alkyl, aryl and benzyl.

In one variation, X is either a —C($R_6$,$R_{14}$)—Y— or a C($R_{13}$)=CH group, and is not a direct bond. In another variation, the compounds of the invention exclude those compounds wherein X is a direct bond when $R_1$ and $R_2$ are hydrogen. In another variation, X is selected from a direct bond, —C($R_6$,$R_{14}$)—Y—, and —C($R_{13}$)=CH—, with the proviso that when X is a direct bond and A is formula (III) then at least one of $R_7$, $R_8$ and $R_9$ is not hydrogen. In another variation, the compounds of the invention exclude those compounds wherein X is a direct bond when A is formula (III) and each of $R_7$, $R_8$ and $R_9$ is hydrogen. In another variation, the compounds of the invention exclude those compounds wherein X is a direct bond when A is formula (III).

Ether side chain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_5$-$C_{12}$alkyl and $C_3$-$C_{13}$-carbocyclic rings. Particularly preferred cyclic hydrocarbons include selected aromatic groups such as phenyl, 1-naphthyl, 2-naphthyl, indenyl, acenaphthyl, and fluorenyl and are represented by formulae (III), (IV), (V), (VI), (VII), or (VIII) respectively.

A suitable "A" group in the formula above is a phenyl ring represented by formula (III):

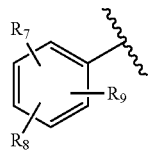

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, aryl and N($R_{15}$,$R_{16}$) where $R_{15}$ and $R_{16}$ are independently selected from hydrogen, acetyl, methanesulfonyl, and $C_1$-$C_6$alkyl.

For compounds of formula (I) where X is a direct bond or $CH_2$, at least one of $R_7$, $R_8$ and $R_9$ is preferably selected from amine (—N$R_{15}R_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$allyl, $C_1$-$C_6$alkoxy, $C_2$-$C_7$alkylcarbonyl, $C_1$-$C_6$thioalkyl or aryl groups. For compounds of formula (I) when X is CH=CH, and $R_3$ and $R_4$ are hydrogen, at least one of $R_7$, $R_8$ and $R_9$ is preferably a substituent other than hydrogen. In one variation, the present invention provides compounds of formula (I) where A includes phenyl groups of formula (IIII) such that at least one of $R_7$, $R_8$ and $R_9$ is not hydrogen, i.e., formula (III) is a phenyl group that contains at least one non-hydrogen substituent. In another variation, $R_7$, $R_3$ and $R_9$ are selected from amine (—N$R_{15}R_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$alkyl, $C_1$-$C_6$alkoxy, $C_2$-$C_7$alkylcarbonyl and $C_1$-$C_6$thioalkyl, i.e., none of $R_7$, $R_8$ or $R_9$ is aryl. In another variation, A does not include a phenyl ring of formula (III) when X is a direct bond.

Other suitable "A" groups are 1-naphthyl groups as represented by formula (IV):

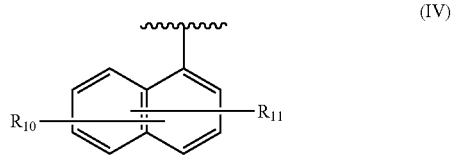

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$,$R_{16}$) where $R_{15}$ and $R_{16}$ are independently selected from hydrogen, acetyl, methanesulfonyl, and $C_1$-$C_6$alkyl.

Other suitable "A" groups are 2-naphthyl group as represented by formula (V):

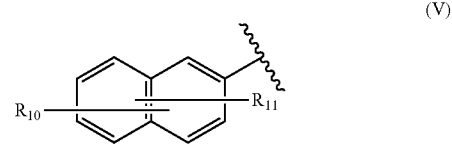

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$,$R_{16}$) where $R_{15}$ and $R_{16}$ are independently selected from hydrogen, acetyl, methanesulfonyl, and $C_1$-$C_6$alkyl, as defined above.

Other suitable "A" groups are aromatic groups represented by formula (VI):

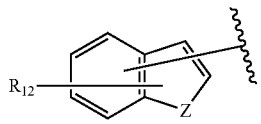

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl.

The aryl groups of formula (VI) are derivatives of indene, indole, benzofuran, and thianaphthene when Z is methylene, nitrogen, oxygen, and sulfur, respectively. Preferred heterocyclic groups of formula (VI) include indole where Z is NH, benzofuran where Z is O, and thianaphthene where Z is S. As described below, in a preferred embodiment, Z is O, S or N—$R_{17}$, and in a particularly preferred embodiment Z is O or S.

Another suitable "A" group is acenaphthyl groups as represented by formula (VII):

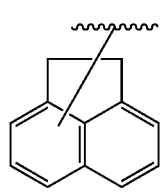

(VII)

Still another suitable "A" group is the fluorenyl group represented by formula (VIII):

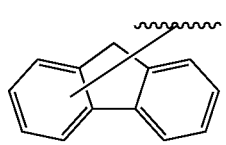

(VIII)

In some variations, ether side chain component A is an acenapthyl or fluorenyl group only when X is a direct bond or $CH_2$. In other variations, the acenaphthyl group is a 1-acenaphthyl group, and the fluorenyl group is a 9-fluorenyl group.

In a particular variation of formula (I), X is $(CH_2)$—Y. For these variations, Y is preferably a direct bond, an oxygen atom, or a sulfur atom. In a another variation, Y is a direct bond or an oxygen atom. In still another variation Y is a direct bond and X is $C(R_6,R_{14})$, where $R_6$ and $R_{14}$ are as defined above. In yet another variation, X is $C(R_{13})$=CH, and $R_{13}$ is a hydrogen atom. For these variations, $R_3$ and $R_4$ may be independently attached to the cyclohexane ring at the 4- or 5-positions.

In another version of the amino cyclohexyl ether ion channel modulating compounds, the ion channel modulating compound is a compound of the formula (I), wherein: independently at each occurrence, X is selected from a direct bond, —$C(R_6,R_{14})$—Y— and —$C(R_{13})$=CH—, with the proviso that when X is a direct bond and A is formula (III) then at least one of $R_7$, $R_8$ and $R_9$ is not hydrogen;

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (I), form a ring denoted by formula (II):

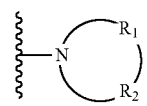

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$-carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

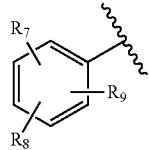
(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and $N(R_{15},R_{16})$ where $R_{15}$ and $R_{16}$ are independently selected from hydrogen, acetyl, methanesulfonyl and $C_1$-$C_6$alkyl;

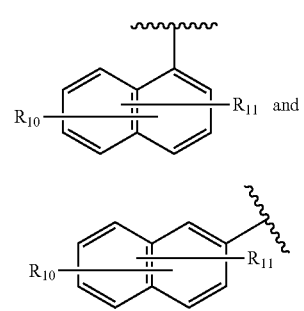
(IV) and (V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl;

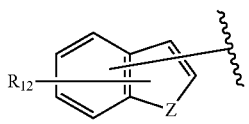
(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

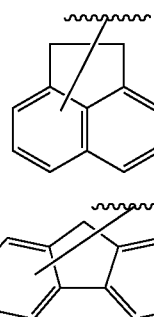
(VII)

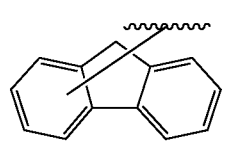
(VIII)

including isolated enantiomeric, diastereomeric and geometric isomers thereof and solvates and/or pharmaceutically acceptable salts of any of the foregoing.

In another version of the amino cyclohexyl ether ion channel modulating compounds, the ion channel modulating compound is a compound of the formula (IX), or a solvate or pharmaceutically acceptable salt thereof:

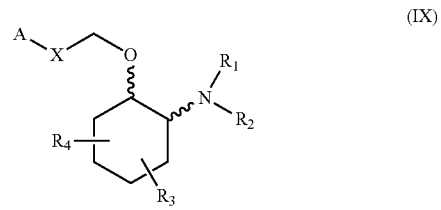
(IX)

wherein, independently at each occurrence,
X is selected from a direct bond, —CH=CH— and —C($R_6$,$R_{14}$)—Y—;
Y is selected from a direct bond, O and S; and
$R_1$, $R_2$, $R_3$, $R_4$, $R_6$, $R_7$, $R_8$, $R_9$, $R_{10}$, $R_{11}$, $R_{12}$, $R_{14}$, A and Z are defined as above for compounds of formula (I).

In another version of the amino cyclohexyl ether ion channel modulating compounds, the ion channel modulating compound is a compound of the formula (X), or a solvate or pharmaceutically acceptable salt thereof:

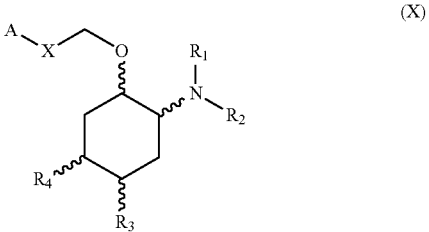
(X)

wherein, independently at each occurrence,
X is selected from a direct bond, —CH=CH— and —C($R_6$,$R_{14}$)—Y—;
Y is selected from a direct bond, O, and S;
$R_1$, $R_2$, $R_6$ and $R_{14}$ are defined as above for compounds of formula (I);
$R_3$ and $R_4$ are independently attached to the cyclohexane ring at the 4- or 5-positions, and are independently selected from hydrogen and $C_1$-$C_6$alkoxy; and
A is selected from $C_5$-$C_{12}$alkyl, $C_3$-$C_8$cycloalkyl, and any of formulae (III), (IV), (V), and (VI) as above for compounds of formula (I), wherein Z, $R_7$, $R_8$, $R_9$, $R_{10}$, $R_{11}$ and $R_{12}$ are defined as above for compounds of formula (I).

In another version of the amino cyclohexyl ether ion channel modulating compounds, the ion channel modulating compound is a compound of the formula (XI), or a solvate or pharmaceutically acceptable salt thereof:

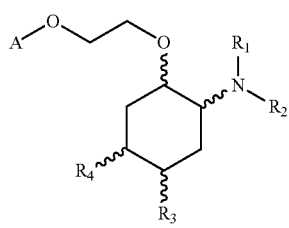

(XI)

wherein, independently at each occurrence, $R_1$ and $R_2$ are defined as above for compounds of formula (I);

$R_3$ and $R_4$ are independently attached to the cyclohexane ring at the 4- or 5-positions, and are independently selected from hydrogen and methoxy; and A is selected from $C_5$-$C_{12}$alkyl, $C_3$-$C_8$cycloalkyl, and any of formulae (III), (IV), (V), and (VI) as above for compounds of formula (I), wherein Z, $R_7$, $R_8$, $R_9$, $R_{10}$, $R_{11}$ and $R_{12}$ are defined as above for compounds of formula (I).

In another version of the amino cyclohexyl ether ion channel modulating compounds, the ion channel modulating compound is a compound of the formula (XII), or a solvate or pharmaceutically acceptable salt thereof:

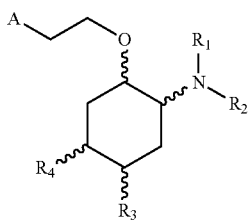

(XII)

wherein, independently at each occurrence, $R_1$ and $R_2$ are defined as above for compounds of formula (I);

$R_3$ and $R_4$ are independently attached to the cyclohexane ring at the 4- or 5-positions, and are independently selected from hydrogen and methoxy; and A is selected from $C_5$-$C_{12}$alkyl, $C_3$-$C_8$cycloalkyl, and any of formulae (III), (IV), (V), and (VI) as above for compounds of formula (I), wherein Z, $R_7$, $R_8$, $R_9$, $R_{10}$, $R_{11}$ and $R_{12}$ are defined as above for compounds of formula (I).

In another version of the amino cyclohexyl ether ion channel modulating compounds, the ion channel modulating compound is a compound of the formula (XIII), or a solvate or pharmaceutically acceptable salt thereof:

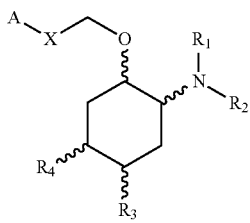

(XIII)

wherein, independently at each occurrence,

X is selected from —C($R_6$,$R_{14}$)—Y— and —CH=CH—;

Y, $R_1$, $R_2$, $R_6$ and $R_{14}$ are defined as above for compounds of formula (I);

$R_3$ and $R_4$ are independently attached to the cyclohexane ring at the 4- or 5-positions, and are independently selected from hydrogen and methoxy; and A is selected from $C_3$-$C_8$cycloalkyl and any of formulae (III), (IV), (V), (VI), (VII) and (VIII) as above for compounds of formula (I), where $R_8$ and $R_9$ are defined as above for compounds of formula (I); $R_7$, $R_{10}$, $R_{11}$ and $R_{12}$ are hydrogen, and Z is selected from O, S and N—$R_{17}$ where $R_{17}$ is selected from hydrogen and methyl.

In another version of the amino cyclohexyl ether ion channel modulating compounds, the ion channel modulating compound is a compound of the formula (XIV), or a solvate or pharmaceutically acceptable salt thereof:

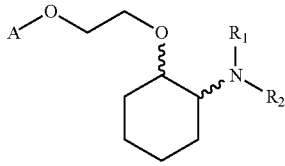

(XIV)

wherein, independently at each occurrence, $R_1$ and $R_2$ are defined as above for compounds of formula (I);

A is selected from any of formulae (III), (IV), (V) and (VI) as above for compounds of formula (I), wherein $R_7$, $R_{10}$, $R_{11}$, and $R_{12}$, are hydrogen, $R_8$ and $R_9$ are independently selected from hydrogen, hydroxy, fluorine, chlorine, bromine, methanesulfonamido, methanoyloxy, methoxycarbonyl, nitro, sulfamyl, thiomethyl, trifluoromethyl, methyl, ethyl, methoxy, ethoxy and $NH_2$, with the proviso that at least one of $R_8$ and $R_9$ is not hydrogen; and Z is selected from O and S.

In another version of the amino cyclohexyl ether ion channel modulating compounds, the ion channel modulating compound is a compound of the formula (XV), or a solvate or pharmaceutically acceptable salt thereof:

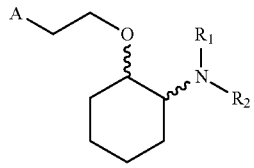

(XV)

wherein, independently at each occurrence,

R$_1$ and R$_2$ are defined as above for compounds of formula (I); and

A is selected from any of formulae (III), (IV), (V) and (VI) as defined above for compounds of formula (I), wherein R$_7$, R$_{10}$, R$_{11}$, and R$_{12}$, are hydrogen, R$_8$ and R$_9$ are independently selected from hydrogen, hydroxy, fluorine, chlorine, bromine, methanesulfonamido, methanoyloxy, methoxycarbonyl, nitro, sulfamyl, thiomethyl, trifluoromethyl, methyl, ethyl, methoxy, ethoxy and NH$_2$, with the proviso that at least one of R$_8$ and R$_9$ is not hydrogen; and Z is selected from O and S.

In another version of the amino cyclohexyl ether ion channel modulating compounds, the ion channel modulating compound is a compound of the formula (XVI), or a solvate or pharmaceutically acceptable salt thereof:

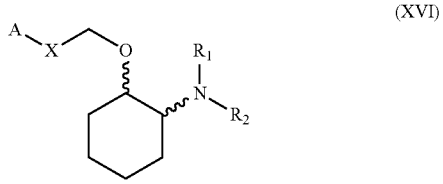

(XVI)

wherein, independently at each occurrence,

X is selected from a direct bond, trans-CH=CH—, —CH$_2$— and —CH$_2$—O—;

R$_1$ and R$_2$ are both methoxyethyl or, when taken together with the nitrogen atom to which they are attached, complete a ring selected from pyrrolidinyl, 2-ketopyrrolidinyl, 3-ketopyrrolidinyl, 2-acetoxypyrrolidinyl, 3-acetoxypyrrolidinyl, 2-hydroxypyrrolidinyl, 3-hydroxypyrrolidinyl, thiazolidinyl, piperidinyl, 2-ketopiperidinyl, 3-ketopiperidinyl, 4-ketopiperidinyl, acetylpiperazinyl, 1,4-dioxa-7-azaspiro[4.4]non-7-yl, hexahydroazepinyl, morpholinyl, N-methylpiperazinyl and 3-azabicyclo[3.2.2]nonanyl; and A is selected from cyclohexyl, monochlorophenyl, 2,6-dichlorophenyl, 3,4-dichlorophenyl, 2-bromophenyl, 2,4-dibromophenyl, 3-bromophenyl, 4-bromophenyl, 3,4-dimethoxyphenyl, 1-naphthyl, 2-naphthyl, 3-benzo[b]thiophenyl, 4-benzo[b]thiophenyl, (2-trifluoromethyl)phenyl, 2,4-di(trifluoromethyl)phenyl, and (4-trifluoromethyl)phenyl.

In another version of the amino cyclohexyl ether ion channel modulating compounds, the ion channel modulating compound is a compound of the formula (XVII), or a solvate or pharmaceutically acceptable salt thereof:

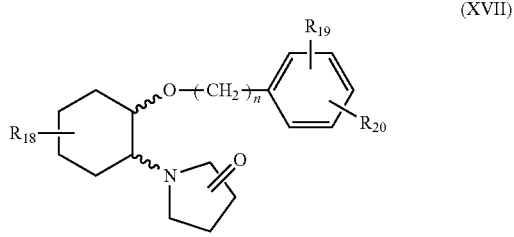

(XVII)

wherein, independently at each occurrence, n is selected from 1, 2 and 3;

R$_{18}$ is either hydrogen or methyl and is independently attached to the cyclohexane ring shown in formula (XVII) at one of the 3-, 4-, 5- or 6-positions;

R$_{19}$ is selected from a group consisting of bromine, chlorine, fluorine and hydrogen; and R$_{20}$ is selected from a group consisting of bromine, chlorine and fluorine;

including isolated enantiomeric, diastereomeric and geometric isomers thereof.

In another version of the amino cyclohexyl ether ion channel modulating compounds, the ion channel modulating compound is a compound that is a trans configuration of formula (XVII) as represented by formula (XVIII), or a solvate or pharmaceutically acceptable salt thereof:

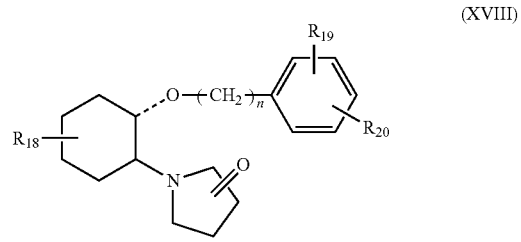

(XVIII)

wherein, independently at each occurrence, n is selected from 1, 2 and 3;

R$_{18}$ is either hydrogen or methyl and is independently attached to the cyclohexane ring shown in formula (XVII) at one of the 3-, 4-, 5- or 6-positions;

R$_{19}$ is selected from a group consisting of bromine, chlorine, fluorine and hydrogen; and R$_{20}$ is selected from a group consisting of bromine, chlorine and fluorine;

including isolated enantiomeric, diastereomeric and geometric isomers thereof.

In another version of the amino cyclohexyl ether ion channel modulating compounds, the ion channel modulating compound is a compound of the formula (IXX); or a solvate or pharmaceutically acceptable salt thereof:

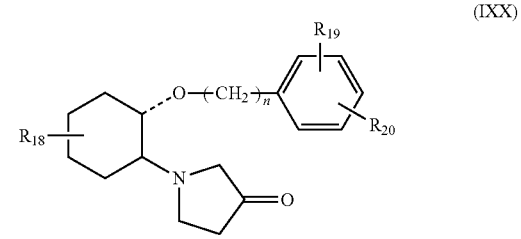

(IXX)

wherein, independently at each occurrence, n is selected from 1, 2 and 3;

R$_{18}$ is either hydrogen or methyl and is independently attached to the cyclohexane ring shown in formula (XVII) at one of the 3-, 4-, 5- or 6-positions;

R$_{19}$ is selected from a group consisting of bromine, chlorine, fluorine and hydrogen; and R$_{20}$ is selected from a group consisting of bromine, chlorine and fluorine;

including isolated enantiomeric, diastereomeric and geometric isomers thereof.

In another version of the aminocyclohexyl ether ion channel modulating compounds, the ion channel modulating compound is compound of formula (XX), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(XX)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof, with the proviso that $R_3$, $R_4$ and $R_5$ cannot all be hydrogen.

In another version of the aminocyclohexyl ether ion channel modulating compounds, the ion channel modulating compound is compound of formula (XX), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is compound of formula (XX), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XX), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In another version of the aminocyclohexyl ether ion channel modulating compounds, the ion channel modulating compound is compound of formula (XX), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XX), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XX), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$alkoxy.

In another version of the aminocyclohexyl ether ion channel modulating compounds, the ion channel modulating compound is compound of formula (XX), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$alkoxy.

In another version of the aminocyclohexyl ether ion channel modulating compounds, the ion channel modulating compound is compound of formula (XXI), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(XXI)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XXI), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is compound of formula (XXI), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XXI), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In another version of the aminocyclohexyl ether ion channel modulating compounds, the ion channel modulating compound is compound of formula (XXI), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XXI), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XXI), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$ alkoxy.

In another version of the aminocyclohexyl ether ion channel modulating compounds, the ion channel modulating compound is compound of formula (XXI), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$alkoxy.

In another version of the aminocyclohexyl ether ion channel modulating compounds, the ion channel modulating compound is compound of formula (XXII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(XXII)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XXII), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is compound of formula (XXII), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XXII), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In another version of the aminocyclohexyl ether ion channel modulating compounds, the ion channel modulating compound is compound of formula (XXII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XXII), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XXII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$alkoxy.

In another version of the aminocyclohexyl ether ion channel modulating compounds, the ion channel modulating compound is compound of formula (XXII), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$alkoxy.

In another version of the aminocyclohexyl ether ion channel modulating compounds, the ion channel modulating compound is compound of formula (XXIII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(XXIII)

wherein, $R_3$, $R_4$ and $R_5$ are independently selected from hydrogen, hydroxy and $C_1$-$C_6$alkoxy, including isolated enantiomeric, diastereomeric and geometric isomers thereof; and mixtures thereof.

In another version of the aminocyclohexyl ether ion channel modulating compounds, the ion channel modulating compound is compound of formula (XXIII), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is compound of formula (XXIII), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XXIII), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In another version of the aminocyclohexyl ether ion channel modulating compounds, the ion channel modulating compound is compound of formula (XXIII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XXIII), or a solvate, pharmaceutically acceptable salt thereof; including isolated enantiomeric, diastereomeric and geometric isomers thereof; and mixtures thereof; wherein, $R_3$ is hydrogen, $R_4$ and $R_5$ are independently selected from $C_1$-$C_6$alkoxy.

In another version of the aminocyclohexyl ether ion channel modulating compounds, the ion channel modulating compound is compound of formula (XXIII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$alkoxy.

In another version of the aminocyclohexyl ether ion channel modulating compounds, the ion channel modulating compound is compound of formula (XXIII), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$alkoxy.

In another version of the aminocyclohexyl ether ion channel modulating compounds, the ion channel modulating compound is compound of formula (XXIV), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

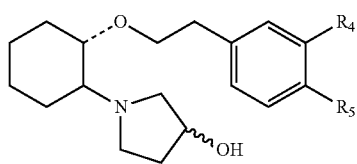

(XXIV)

wherein, $R_4$ and $R_5$ are independently selected from hydrogen, hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XXIV), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is compound of formula (XXIV), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is compound of formula (XXIV), or a solvate, pharmaceutically acceptable salt thereof, including isolated enantiomeric, diastereomeric and geometric isomers thereof, and mixtures thereof, wherein, $R_4$ and $R_5$ are independently selected from hydroxy and $C_1$-$C_3$alkoxy.

In another version of the aminocyclohexyl ether ion channel modulating compounds, the ion channel modulating compound is compound of formula (XXIV), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_4$ and $R_5$ are independently selected from $C_1$-$C_6$alkoxy.

In another version of the aminocyclohexyl ether ion channel modulating compounds, the ion channel modulating compound is compound of formula (XXIV), or a solvate, pharmaceutically acceptable salt thereof, including isolated enantiomeric, diastereomeric and geometric isomers thereof, and mixtures thereof, wherein, $R_4$ and $R_5$ are independently selected from $C_1$-$C_3$alkoxy.

In another version of the aminocyclohexyl ether ion channel modulating compounds, the ion channel modulating compound is compound of formula (XXIV), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_4$ and $R_5$ are $C_1$alkoxy.

In another version of the aminocyclohexyl ether ion channel modulating compounds, the ion channel modulating compound is compound of formula (XXIV), or a solvate, pharmaceutically acceptable salt thereof, including isolated enantiomeric, diastereomeric and geometric isomers thereof, and mixtures thereof, wherein, $R_4$ and $R_5$ are $C_1$alkoxy.

In another version of the amino cyclohexyl ether ion channel modulating compounds, the ion channel modulating compound is a compound of the formula (XXV),

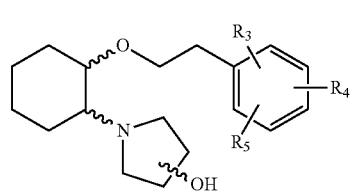

(XXV)

wherein:
$R_3$, $R_4$ and $R_5$ are independently selected from hydrogen, hydroxy and $C_1$-$C_6$alkoxy; or,
$R_3$, $R_4$ are independently selected from hydroxyl and $C_1$-$C_6$alkoxy and $R_5$ is hydrogen; or,
$R_3$, $R_4$ are both $C_1$-$C_6$alkoxy and $R_5$ is hydrogen; or
$R_3$, $R_4$ are both methoxy and $R_5$ is hydrogen; or
including isolated enantiomeric, diastereomeric and geometric isomers thereof, and mixtures thereof, with the proviso that $R_3$, $R_4$ and $R_5$ cannot all be hydrogen; and
〰 indicates a bond that provides a R stereoisomer or a S stereoisomer at the position to which the bond is attached.

In one variation, the hydroxyl substituent is positioned at the 3 position of the pyrrolidinyl ring in (XXV). In another variation, the stereochemistry at the position of the cycloalkyl ring of (XXV) containing the nitrogen group is racemic, which may be provided for any of the variations mentioned above.

In another version of the amino cyclohexyl ether ion channel modulating compounds, the ion channel modulating compound is a compound of the formula (XXVI):

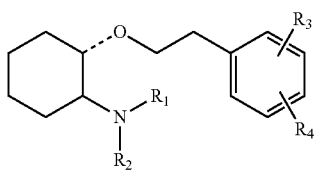

(XXVI)

wherein:

the ---- bond to the ether oxygen indicates that the ether and amine groups attached to the cyclohexyl group are in a trans configuration. and the C-1 and C-2 carbons of the cyclohexyl group may be either R,R configuration or S,S configuration; $R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$, are taken together with the nitrogen atom to which they are directly attached in formula (XXVI) to form a ring denoted by formula (IV):

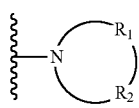

(IV)

wherein the ring of formula (IV) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six membered heterocyclic ring containing one or two heteroatoms selected from oxygen and sulfur; and any two adjacent additional carbon ring atoms may be fused to a $C_3$-$C_8$-carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together to form

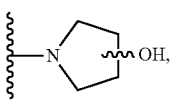

wherein the OH group may be at any position on the pyrrolidinyl ring, including the 3-position;

$R_1$ and $R_2$, when taken together with the nitrogen atom to which they are directly attached in formula (XXVI), may form a bicyclic ring system selected from 3 azabicyclo[3.2.2] nonan 3 yl, 2 azabicyclo[2.2.2]octan 2 yl, 3 azabicyclo[3.1.0] hexan 3 yl and 3 azabicyclo[3.2.0]heptan 3 yl;

$R_3$ and $R_4$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and $N(R_{15},R_{16})$ where $R_{15}$ and $R_{16}$ are independently selected from hydrogen, acetyl, methanesulfonyl and $C_1$-$C_6$alkyl; and In one version of formula (XXVI), $R_3$ and $R_4$ are independently selected from hydrogen, hydroxyl and $C_1$-$C_6$alkoxy. In another version of formula (XXVI), both $R_3$ and $R_4$ are $C_1$-$C_6$alkoxy. In another variation, both $R_3$ and $R_4$ are methoxy. In still another variation of formula (XXVI), $R_3$ and $R_4$ are positioned at the 3 and 4 positions of the aromatic ring, wherein the position on the aromatic ring containing the alkyl chain is designated the 1 position, this variation may be combined with any other variation mentioned above.

In another version of the amino cyclohexyl ether ion channel modulating compounds, the ion channel modulating compound is a compound of the formula (XXVII), or pharmaceutically acceptable salts or solvates thereof.

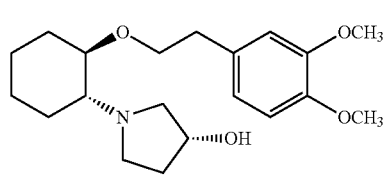

(XXVII)

(1R,2R)-2-[(3R)-hydroxypyrrolidinyl]-1-(3,4-dimethoxyphenethoxy)cyclohexane

In another version of the amino cyclohexyl ether ion channel modulating compounds, the ion channel modulating compound is a compound of the formula (XXVIII),

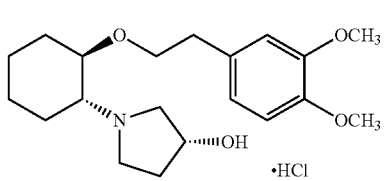

(XXVIII)

(1R,2R)-2-[(3R)-hydroxypyrrolidinyl]-1-(3,4-dimethoxyphenethoxy)cyclohexane monohydrochloride In another version of the aminocyclohexyl ether ion channel modulating compounds, the ion channel modulating compound is compound or any salt thereof, or any solvate thereof, or mixture comprising one or more said compounds or any salt thereof, or any solvate thereof, selected from the group consisting of:

| | |
|---|---|
| (1R,2R)-[2-(4-morpholinyl)-1-(2-naphthenethoxy)] cyclohexane or (1S,2S)-[2-(4-morpholinyl)-1-(2-naphthenethoxy)] cyclohexane or a mixture of (1R,2R)-[2-(4-morpholinyl)-1-(2-naphthenethoxy)]cyclohexane and (1S,2S)-[2-(4-morpholinyl)-1-(2-naphthenethoxy)]cyclohexane | 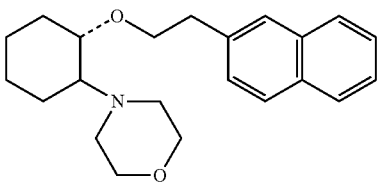 |
| (1R,2R)-[2-(4-morpholinyl)-1-(1-naphthenethoxy)] cyclohexane or (1S,2S)-[2-(4-morpholinyl)-1-(1-naphthenethoxy)] cyclohexane or a mixture of (1R,2R)-[2-(4-morpholinyl)-1-(1-naphthenethoxy)] cyclohexane and (1S,2S)-[2-(4-morpholinyl)-1-(1-naphthenethoxy)] | 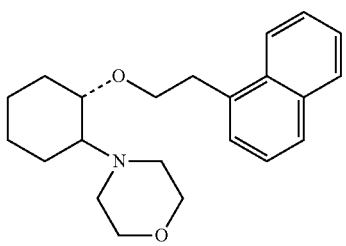 |
| (1R,2R)-[2-(4-morpholinyl)-1-(4-bromophenethoxy)] cyclohexane or (1S,2S)-[2-(4-morpholinyl)-1-(4-bromophenethoxy)] cyclohexane or a mixture of (1R,2R)-[2-(4-morpholinyl)-1-(4-bromophenethoxy)] cyclohexane and (1S,2S)-[2-(4-morpholinyl)-1-(4-bromophenethoxy)] cyclohexane | 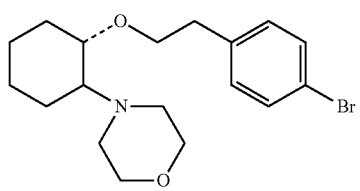 |
| (1R,2R)-[2-(4-morpholinyl)-1-[2-(2-naphthoxy) ethoxy]] cyclohexane or (1S,2S)-[2-(4-morpholinyl)-1-[2-(2-naphthoxy)ethoxy]] cyclohexane or a mixture of (1R,2R)-[2-(4-morpholinyl)-1-[2-(2-naphthoxy) ethoxy]] cyclohexane and (1S,2S)-[2-(4-morpholinyl)-1-[2-(2-naphthoxy)ethoxy]] cyclohexane | 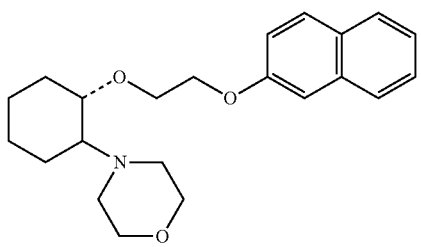 |
| (1R,2R)-[2-(4-morpholinyl)-1-[2-(4-bromophenoxy) ethoxy]] cyclohexane or (1S,2S)-[2-(4-morpholinyl)-1-[2-(4-bromophenoxy) ethoxy]] cyclohexane or a mixture of (1R,2R)-[2-(4-morpholinyl)-1-[2-(4-bromophenoxy) ethoxy]] cyclohexane and (1S,2S)-[2-(4-morpholinyl)-1-[2-(4-bromophenoxy) ethoxy]] cyclohexane | 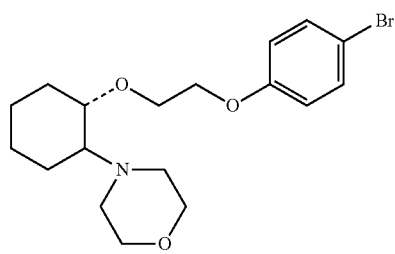 |
| (1R,2R)-[2-(4-morpholinyl)-1-(3,4-dimethoxyphen ethoxy)] cyclohexane or (1S,2S)-[2-(4-morpholinyl)-1-(3,4-dimethoxyphen ethoxy)] cyclohexane or a mixture of (1R,2R)-[2-(4-morpholinyl)-1-(3,4-dimethoxyphen ethoxy)] cyclohexane and (1S,2S)-[2-(4-morpholinyl)-1-(3,4-dimethoxyphen ethoxy)] cyclohexane | 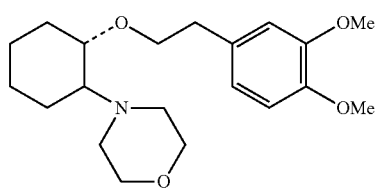 |
| (1R,2R)-[2-(1-pyrrolidinyl)-1-(1-naphthenethoxy)] cyclohexane or (1S,2S)-[2-(1-pyrrolidinyl)-1-(1-naphthenethoxy)] cyclohexane or a mixture of (1R,2R)-[2-(1-pyrrolidinyl)-1-(1-naphthenethoxy)] cyclohexane and (1S,2S)-[2-(1-pyrrolidinyl)-1-(1-naphthenethoxy)] cyclohexane | 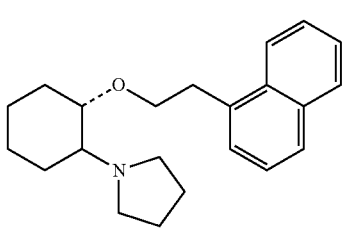 |

| | |
|---|---|
| (1R,2R)-[2-(4-morpholinyl)-1-(2-(benzo[b]thiophen-3-yl)] cyclohexane or (1S,2S)-[2-(4-morpholinyl)-1-(2-(benzo[b]thiophen-3-yl)] cyclohexane or a mixture of (1R,2R)-[2-(4-morpholinyl)-1-(2-(benzo[b]thiophen-3-yl)] cyclohexane and (1S,2S)-[2-(4-morpholinyl)-1-(2-(benzo[b]thiophen-3-yl)] cyclohexane | 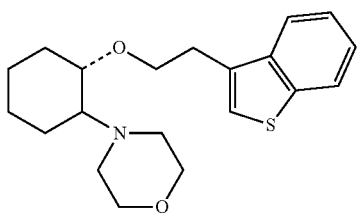 |
| (1R,2R)-[2-(4-morpholinyl)-1-(2-(benzo[b]thiophen-4-yl)] cyclohexane or (1S,2S)-[2-(4-morpholinyl)-1-(2-(benzo[b]thiophen-4-yl)]cyclohexane or a mixture of (1R,2R)-[2-(4-morpholinyl)-1-(2-(benzo[b]thiophen-4-yl)] cyclohexane and (1S,2S)-[2-(4-morpholinyl)-1-(2-(benzo[b]thiophen-4-yl)]cyclohexane | 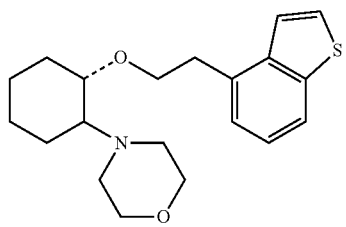 |
| (1R,2R)-[2-(4-morpholinyl)-1-(3-bromophenethoxy)] cyclohexane or (1S,2S)-[2-(4-morpholinyl)-1-(3-bromophenethoxy)] cyclohexane or a mixture of (1R,2R)-[2-(4-morpholinyl)-1-(3-bromophenethoxy)] cyclohexane and (1S,2S)-[2-(4-morpholinyl)-1-(3-bromophenethoxy)] cyclohexane | 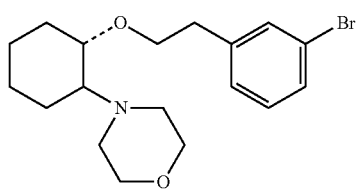 |
| (1R,2R)-[2-(4-morpholinyl)-1-(2-bromophenethoxy)] cyclohexane or (1S,2S)-[2-(4-morpholinyl)-1-(2-bromophenethoxy)] cyclohexane or (1R,2R)-[2-(4-morpholinyl)-1-(2-bromophenethoxy)] cyclohexane and (1S,2S)-[2-(4-morpholinyl)-1-(2-bromophenethoxy)] cyclohexane | 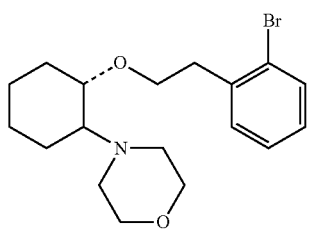 |
| (1R,2R)-[2-(4-morpholinyl)-1-(3-(3,4-dimethoxyphenyl) propoxy)] cyclohexane or (1S,2S)-[2-(4-morpholinyl)-1-(3-(3,4-dimethoxyphenyl) propoxy)] cyclohexane or a mixture of (1R,2R)-[2-(4-morpholinyl)-1-(3-(3,4-dimethoxyphenyl) propoxy)] cyclohexane and (1S,2S)-[2-(4-morpholinyl)-1-(3-(3,4-dimethoxyphenyl) propoxy)] cyclohexane | 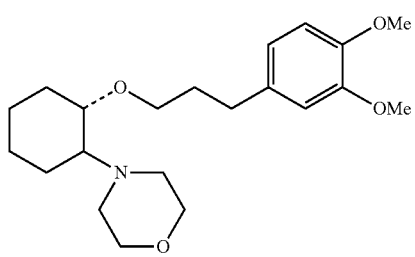 |
| (1R,2R)-[2-[bis(2-methoxyethyl)aminyl]-1-(2-naphthen ethoxy)] cyclohexane or (1S,2S)-[2-[bis(2-methoxyethyl)aminyl]-1-(2-naphthen ethoxy)] cyclohexane and a mixture of (1R,2R)-[2-[bis(2-methoxyethyl)aminyl]-1-(2-naphthen ethoxy)] cyclohexane and (1S,2S)-[2-[bis(2-methoxyethyl)aminyl]-1-(2-naphthen ethoxy)] cyclohexane | 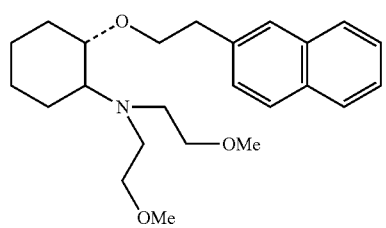 |
| (1R,2R)-2-(4-morpholinyl)-1-(3,4-dichlorophen ethoxy) cyclohexane or (1S,2S)-2-(4-morpholinyl)-1-(3,4-dichlorophen ethoxy) cyclohexane or a mixture of (1R,2R)-2-(4-morpholinyl)-1-(3,4-dichlorophen ethoxy) cyclohexane and (1S,2S)-2-(4-morpholinyl)-1-(3,4-dichlorophen ethoxy) cyclohexane | 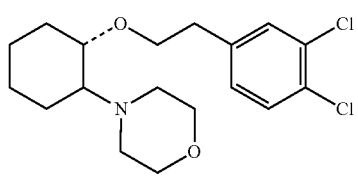 |

| | |
|---|---|
| (1R,2R)-2-(3-ketopyrrolidinyl)-1-(1-naphthenethoxy) cyclohexane or (1S,2S)-2-(3-ketopyrrolidinyl)-1-(1-naphthenethoxy) cyclohexane or a mixture of (1R,2R)-2-(3-ketopyrrolidinyl)-1-(1-naphthenethoxy) cyclohexane and (1S,2S)-2-(3-ketopyrrolidinyl)-1-(1-naphthenethoxy) cyclohexane | 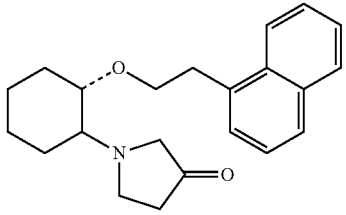 |
| (1R,2R)-2-(1-acetylpiperazinyl)-1-(2-naphthenethoxy) cyclohexane or (1S,2S)-2-(1-acetylpiperazinyl)-1-(2-naphthenethoxy) cyclohexane or a mixture of (1R,2R)-2-(1-acetylpiperazinyl)-1-(2-naphthenethoxy) cyclohexane and (1S,2S)-2-(1-acetylpiperazinyl)-1-(2-naphthenethoxy) cyclohexane | 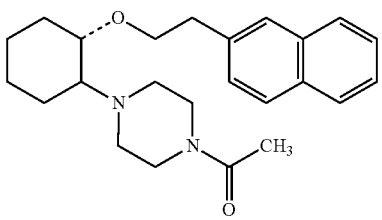 |
| (1R,2R)-2-(3-ketopyrrolidinyl)-1-(2,6-dichlorophenethoxy) cyclohexane or (1S,2S)-2-(3-ketopyrrolidinyl)-1-(2,6-dichlorophenethoxy) cyclohexane or a mixture of (1R,2R)-2-(3-ketopyrrolidinyl)-1-(2,6-dichlorophenethoxy) cyclohexane and (1S,2S)-2-(3-ketopyrrolidinyl)-1-(2,6-dichlorophenethoxy) cyclohexane | 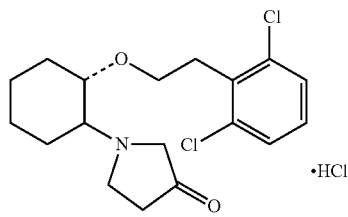 |
| (1R,2R)-2-[1,4-dioxa-7-azaspiro[4.4]non-7-yl]-1-(1-naphthen ethoxy) cyclohexane or (1S,2S)-2-[1,4-dioxa-7-azaspiro[4.4]non-7-yl]-1-(1-naphthen ethoxy) cyclohexane and a mixture of (1R,2R)-2-[1,4-dioxa-7-azaspiro[4.4]non-7-yl]-1-(1-naphthen ethoxy) cyclohexane and (1S,2S)-2-[1,4-dioxa-7-azaspiro[4.4]non-7-yl]-1-(1-naphthen ethoxy) cyclohexane | 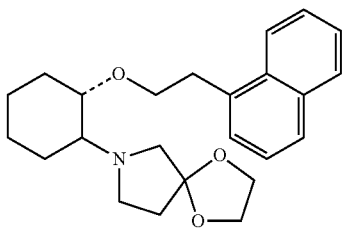 |
| (1R,2S)-2-(4-morpholinyl)-1-[(2-trifluoromethyl)phenethoxy] cyclohexane monohydrochloride or (1S,2R)-2-(4-morpholinyl)-1-[(2-trifluoromethyl)phenethoxy] cyclohexane monohydrochloride or a mixture of (1R,2S)-2-(4-morpholinyl)-1-[(2-trifluoromethyl)phenethoxy] cyclohexane monohydrochloride and (1S,2R)-2-(4-morpholinyl)-1-[(2-trifluoromethyl)phenethoxy] cyclohexane monohydrochloride | 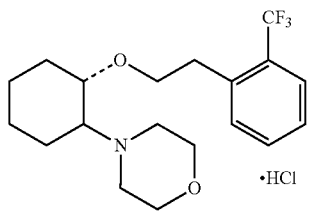 |
| (1R,2R)-2-(3-ketopyrrolidinyl)-1-[3-(cyclohexyl)propoxy] cyclohexane monohydrochloride or (1S,2S)-2-(3-ketopyrrolidinyl)-1-[3-(cyclohexyl)propoxy] cyclohexane monohydrochloride or a mixture of (1R,2R)-2-(3-ketopyrrolidinyl)-1-[3-(cyclohexyl)propoxy] cyclohexane monohydrochloride and (1S,2S)-2-(3-ketopyrrolidinyl)-1-[3-(cyclohexyl)propoxy] cyclohexane monohydrochloride | 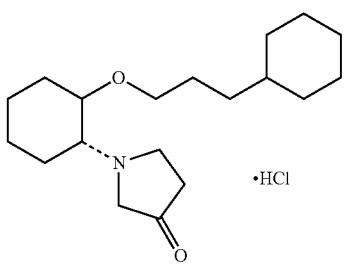 |

| | |
|---|---|
| (1R,2R)-2-(3-acetoxypyrrolidinyl)-1-(1-naphthenethoxy) cyclohexane monohydrochloride or (1S,2S)-2-(3-acetoxypyrrolidinyl)-1-(1-naphthenethoxy) cyclohexane monohydrochloride or a mixture of (1R,2R)-2-(3-acetoxypyrrolidinyl)-1-(1-naphthenethoxy) cyclohexane monohydrochloride and (1S,2S)-2-(3-acetoxypyrrolidinyl)-1-(1-naphthenethoxy) cyclohexane monohydrochloride | 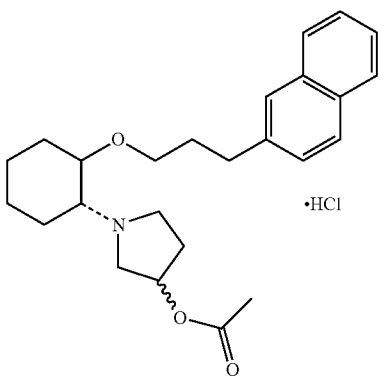 |
| (1R,2R)-2-(4-morpholinyl)-1-[(2,6-dichlorophenyl)methoxy] cyclohexane monohydrochloride or (1S,2S)-2-(4-morpholinyl)-1-[(2,6-dichlorophenyl)methoxy] cyclohexane monohydrochloride or a mixture of (1R,2R)-2-(4-morpholinyl)-1-[(2,6-dichlorophenyl)methoxy] cyclohexane monohydrochloride and (1S,2S)-2-(4-morpholinyl)-1-[(2,6-dichlorophenyl)methoxy] cyclohexane monohydrochloride | 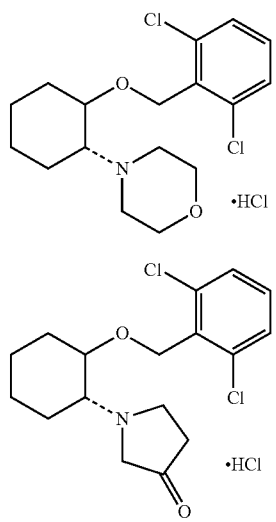 |
| (1R,2R)-2-(3-ketopyrrolidinyl)-1-[(2,6-dichlorophenyl)methoxy] cyclohexane monohydrochloride or (1S,2S)-2-(3-ketopyrrolidinyl)-1-[(2,6-dichlorophenyl)methoxy] cyclohexane monohydrochloride or a mixture of (1R,2R)-2-(3-ketopyrrolidinyl)-1-[(2,6-dichlorophenyl) methoxy] cyclohexane monohydrochloride and (1S,2S)-2-(3-ketopyrrolidinyl)-1-[(2,6-dichlorophenyl) methoxy] cyclohexane monohydrochloride | 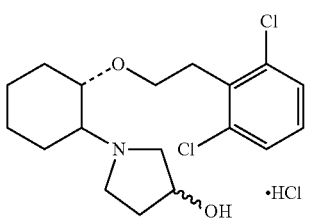 |
| (1R,2R)-2-(3-hydroxypyrrolidinyl)-1-(2,6-dichlorophen ethoxy) cyclohexane monohydrochloride or (1S,2S)-2-(3-hydroxypyrrolidinyl)-1-(2,6-dichlorophen ethoxy) cyclohexane monohydrochloride or a mixture of (1R,2R)-2-(3-hydroxypyrrolidinyl)-1-(2,6-dichlorophen ethoxy) cyclohexane monohydrochloride and (1S,2S)-2-(3-hydroxypyrrolidinyl)-1-(2,6-dichlorophen ethoxy) cyclohexane monohydrochloride | 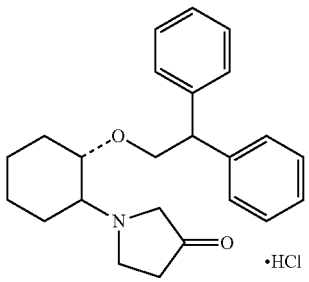 |
| (1R,2R)-2-(3-ketopyrrolidinyl)-1-(2,2-diphenylethoxy) cyclohexane monohydrochloride or (1S,2S)-2-(3-ketopyrrolidinyl)-1-(2,2-diphenylethoxy) cyclohexane monohydrochloride or a mixture of (1R,2R)-2-(3-ketopyrrolidinyl)-1-(2,2-diphenylethoxy) cyclohexane monohydrochloride and (1S,2S)-2-(3-ketopyrrolidinyl)-1-(2,2-diphenylethoxy) cyclohexane monohydrochloride | |
| (1R,2R)-2-(3-thiazolidinyl)-1-(2,6-dichlorophen ethoxy) cyclohexane monohydrochloride or (1S,2S)-2-(3-thiazolidinyl)-1-(2,6-dichlorophen ethoxy) cyclohexane monohydrochloride or a mixture of (1R,2R)-2-(3-thiazolidinyl)-1-(2,6-dichlorophen ethoxy) cyclohexane monohydrochloride and (1S,2S)-2-(3-thiazolidinyl)-1-(2,6-dichlorophenethoxy) cyclohexane monohydrochloride | 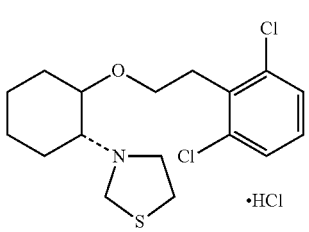 |

| | |
|---|---|
| (1R,2S)-2-(3-ketopyrrolidinyl)-1-(1-naphthenethoxy) cyclohexane monohydrochloride or (1S,2R)-2-(3-ketopyrrolidinyl)-1-(1-naphthenethoxy) cyclohexane monohydrochloride or a mixture of (1R,2S)-2-(3-ketopyrrolidinyl)-1-(1-naphthenethoxy) cyclohexane monohydrochloride and (1S,2R)-2-(3-ketopyrrolidinyl)-1-(1-naphthenethoxy) cyclohexane monohydrochloride | 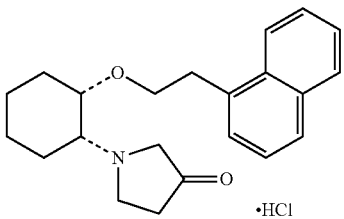 |
| (1R,2R)-2-(3-hydroxypyrrolidinyl)-1-(3,4-dimethoxyphenethoxy) cyclohexane monohydrochloride or (1S,2S)-2-(3-hydroxypyrrolidinyl)-1-(3,4-dimethoxyphenethoxy) cyclohexane monohydrochloride or a mixture of (1R,2R)-2-(3-hydroxypyrrolidinyl)-1-(3,4-dimethoxyphenethoxy) cyclohexane monohydrochloride and (1S,2S)-2-(3-hydroxypyrrolidinyl)-1-(3,4-dimethoxyphenethoxy) cyclohexane monohydrochloride | 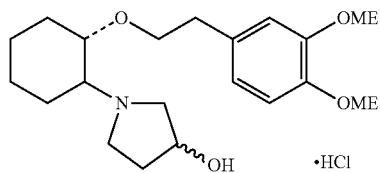 |

Also described here is a composition that includes one or more of the compounds or mixtures listed in the above table, or includes a solvate or a pharmaceutically acceptable salt of one or more of the compounds or mixtures listed in the above table. The composition may or may not include additional components. Additional components that may be used are described elsewhere in detail in this patent.

In another version of the aminocyclohexyl ether ion channel modulating compounds, the ion channel modulating compound is a compound or mixture comprising compounds, or any solvate thereof, selected from the group consisting of:

| Structure | Chemical name |
|---|---|
| ![structure] | (1R,2R)-2-[(3R)/(3S)-Hydroxypyrrolidinyl]-1-(3,4-dimethoxyphenethoxy)-cyclohexane or (1S,2S)-2-[(3R)/(3S)-Hydroxypyrrolidinyl]-1-(3,4-dimethoxyphenethoxy)-cyclohexane or a mixture of (1R,2R)-2-[(3R)/(3S)-Hydroxypyrrolidinyl]-1-(3,4-dimethoxyphenethoxy)-cyclohexane and (1S,2S)-2-[(3R)/(3S)-Hydroxypyrrolidinyl]-1-(3,4-dimethoxyphenethoxy)-cyclohexane |
| ![structure] | (1R,2R)-2-[(3R)-Hydroxypyrrolidinyl]-1-(3,4-dimethoxyphenethoxy)-cyclohexane or (1S,2S)-2-[(3R)-Hydroxypyrrolidinyl]-1-(3,4-dimethoxyphenethoxy)-cyclohexane and a mixture of (1R,2R)-2-[(3R)-Hydroxypyrrolidinyl]-1-(3,4-dimethoxyphenethoxy)-cyclohexane and (1S,2S)-2-[(3R)-Hydroxypyrrolidinyl]-1-(3,4-dimethoxyphenethoxy)-cyclohexane |
| ![structure] | (1R,2R)-2-[(3S)-Hydroxypyrrolidinyl]-1-(3,4-dimethoxyphenethoxy)-cyclohexane or (1S,2S)-2-[(3S)-Hydroxypyrrolidinyl]-1-(3,4-dimethoxyphenethoxy)-cyclohexane and a mixture of (1R,2R)-2-[(3S)-Hydroxypyrrolidinyl]-1-(3,4-dimethoxyphenethoxy)-cyclohexane and (1S,2S)-2-[(3S)-Hydroxypyrrolidinyl]-1-(3,4-dimethoxyphenethoxy)-cyclohexane |
| ![structure] | (1R,2R)-2-[(3R)-Hydroxypyrrolidinyl]-1-(3,4-dimethoxyphenethoxy)-cyclohexane |

-continued

| Structure | Chemical name |
|---|---|
| 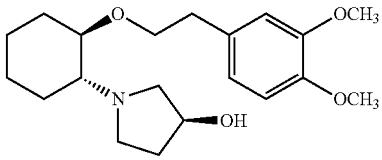 | (1R,2R)-2-[(3S)-Hydroxypyrrolidinyl]-1-(3,4-dimethoxyphenethoxy)-cyclohexane |
| 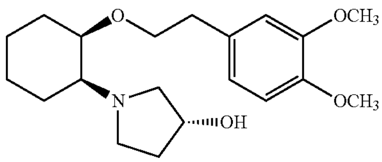 | (1R,2S)-2-[(3R)-Hydroxypyrrolidinyl]-1-(3,4-dimethoxyphenethoxy)-cyclohexane |
| 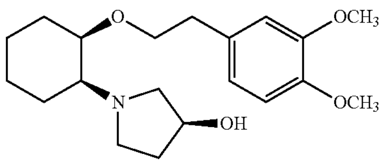 | (1R,2S)-2-[(3S)-Hydroxypyrrolidinyl]-1-(3,4-dimethoxyphenethoxy)-cyclohexane |
| 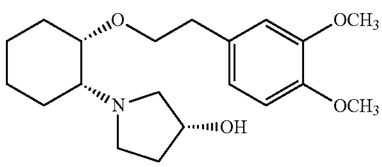 | (1S,2R)-2-[(3R)-Hydroxypyrrolidinyl]-1-(3,4-dimethoxyphenethoxy)-cyclohexane |
| 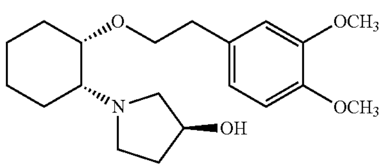 | (1S,2R)-2-[(3S)-Hydroxypyrrolidinyl]-1-(3,4-dimethoxyphenethoxy)-cyclohexane |
| 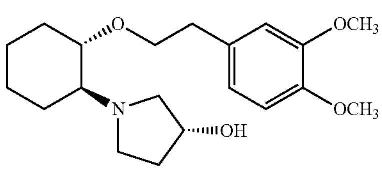 | (1S,2S)-2-[(3R)-Hydroxypyrrolidinyl]-1-(3,4-dimethoxyphenethoxy)-cyclohexane |
| 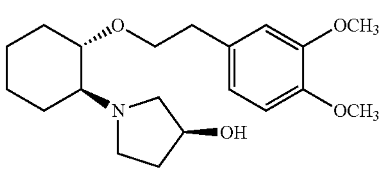 | (1S,2S)-2-[(3S)-Hydroxypyrrolidinyl]-1-(3,4-dimethoxyphenethoxy)-cyclohexane |
|  | (1R,2S)-2-[(3R)/(3S)-Hydroxypyrrolidinyl]-1-(3,4-dimethoxyphenethoxy)-cyclohexane or (1S,2R)-2-[(3R)/(3S)-Hydroxypyrrolidinyl]-1-(3,4-dimethoxyphenethoxy)-cyclohexane or a mixture of (1R,2S)-2-[(3R)/(3S)-Hydroxypyrrolidinyl]-1-(3,4-dimethoxyphenethoxy)-cyclohexane and (1S,2R)-2-[(3R)/(3S)-Hydroxypyrrolidinyl]-1-(3,4-dimethoxyphenethoxy)-cyclohexane |
| 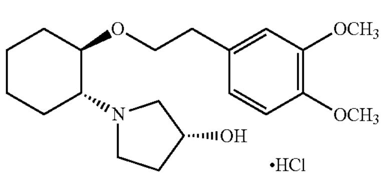 | (1R,2R)-2-[(3R)-Hydroxypyrrolidinyl]-1-(3,4-dimethoxyphenethoxy)-cyclohexane monohydrochloride |

-continued

| Structure | Chemical name |
|---|---|
| [structure] | (1S,2S)-2-[(3R)-Hydroxypyrrolidinyl]-1-(3,4-dimethoxyphenethoxy)-cyclohexane monohydrochloride |
| [structure] | (1R,2R)-2-[(3R)/(3S)-Hydroxypyrrolidinyl]-1-(3,4-dimethoxyphenethoxy)-cyclohexane monohydrochloride or (1S,2S)-2-[(3R)/(3S)-Hydroxypyrrolidinyl]-1-(3,4-dimethoxyphenethoxy)-cyclohexane monohydrochloride or a mixture of (1R,2R)-2-[(3R)/(3S)-Hydroxypyrrolidinyl]-1-(3,4-dimethoxyphenethoxy)-cyclohexane monohydrochloride and (1S,2S)-2-[(3R)/(3S)-Hydroxypyrrolidinyl]-1-(3,4-dimethoxyphenethoxy)-cyclohexane monohydrochloride |
| [structure] | (1R,2R)-2-[(3R)-Hydroxypyrrolidinyl]-1-(3,4-dimethoxyphenethoxy)-cyclohexane monohydrochloride or (1S,2S)-2-[(3R)-Hydroxypyrrolidinyl]-1-(3,4-dimethoxyphenethoxy)-cyclohexane monohydrochloride or a mixture of (1R,2R)-2-[(3R)-Hydroxypyrrolidinyl]-1-(3,4-dimethoxyphenethoxy)-cyclohexane monohydrochloride and (1S,2S)-2-[(3R)-Hydroxypyrrolidinyl]-1-(3,4-dimethoxyphenethoxy)-cyclohexane monohydrochloride |
| [structure] | (1R,2R)-2-[(3S)-Hydroxypyrrolidinyl]-1-(3,4-dimethoxyphenethoxy)-cyclohexane monohydrochloride or (1S,2S)-2-[(3S)-Hydroxypyrrolidinyl]-1-(3,4-dimethoxyphenethoxy)-cyclohexane monohydrochloride or a mixture of (1R,2R)-2-[(3S)-Hydroxypyrrolidinyl]-1-(3,4-dimethoxyphenethoxy)-cyclohexane monohydrochloride and (1S,2S)-2-[(3S)-Hydroxypyrrolidinyl]-1-(3,4-dimethoxyphenethoxy)-cyclohexane monohydrochloride |
| [structure] | (1R,2R)-2-[(3S)-Hydroxypyrrolidinyl]-1-(3,4-dimethoxyphenethoxy)-cyclohexane monohydrochloride |
| [structure] | (1S,2S)-2-[(3S)-Hydroxypyrrolidinyl]-1-(3,4-dimethoxyphenethoxy)-cyclohexane monohydrochloride |

Also described here is a composition that includes one or more of the compounds or mixtures listed in the above table, or includes a solvate or a pharmaceutically acceptable salt of one or more of the compounds or mixtures listed in the above table. The composition may or may not include additional components. Additional components that may be used are described elsewhere in detail in this patent.

In another version of the amino cyclohexyl ether ion channel modulating compounds, the ion channel modulating compound is one of the following compounds: (1R,2R)-2-[(3R)-Hydroxypyrrolidinyl]-1-(3,4-dimethoxyphenethoxy)-cyclohexane free base or any salt thereof, or any solvate thereof; (1R,2R)-2-[(3S)-Hydroxypyrrolidinyl]-1-(3,4-dimethoxyphenethoxy)-cyclohexane free base or any salt thereof, or any solvate thereof; (1S,2S)-2-[(3R)-Hydroxypyrrolidinyl]-1-(3,4-dimethoxyphenethoxy)-cyclohexane free base or any salt thereof, or any solvate thereof; (1S,2S)-2-[(3S)-Hydroxypyrrolidinyl]-1-(3,4-dimethoxyphenethoxy)-cyclohexane free base or any salt thereof, or any solvate thereof; (1R,2R)-2-[(3R)-Hydroxypyrrolidinyl]-1-(3,4-dimethoxyphenethoxy)-cyclohexane monohydrochloride, or any solvate thereof; (1R,2R)-2-[(3S)-Hydroxypyrrolidinyl]-1-(3,4-dimethoxyphenethoxy)-cyclohexane monohydrochloride, or any solvate thereof; (1S,2S)-2-[(3R)-Hydroxypyrrolidinyl]-1-(3,4-dimethoxyphenethoxy)-cyclohexane monohydrochloride, or any solvate thereof; or (1S,2S)-2-[(3S)-Hydroxypyrrolidinyl]-1-(3,4-dimethoxyphenethoxy)-cyclohexane monohydrochloride, or any solvate thereof.

In another version of the amino cyclohexyl ether ion channel modulating compounds, the ion channel modulating compound is a protonated version of any of the amino cyclohexyl ether compounds described in this patent. That is, for each amino cyclohexyl ether compound described in this patent, the quaternary protonated amine form of the compound may also be considered as an amino cyclohexyl ether ion channel modulating compounds. These quaternary protonated amine form of the compounds may be present in the solid phase, for example in crystalline or amorphous form, and may be present in solution. These quaternary protenated amine form of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Aminocycloalkyl Ether Ion Channel Modulating Compounds with 5, 7, and 8 Membered Cycloalkyl Rings One class of compounds that are ion channel modulating compound comprise an aminocycloalkyl ether core structure having an ether oxygen atom at position 1 of a cycloalkyl ring, and an amine nitrogen atom at position 2 of the cycloalkyl ring. In one version the cycloalkyl ring is a 5, 7, or 8 membered ring.

In one version of the amino cycloalkyl ether ion channel modulating compounds, the ion channel modulating compound is a compound having an ether oxygen atom (Q=O in formula (IXXX)) at position 1 of a cycloalkyl ring, and an amine nitrogen atom at position 2 of the cycloalkyl ring, where the cycloalkyl ring is either cyclopentyl, cycloheptyl or cyclooctyl, with other positions numbered in corresponding order as shown below in structure (A) for cyclopentane, structure (B) for cycloheptane, and structure (C) for cyclooctane:

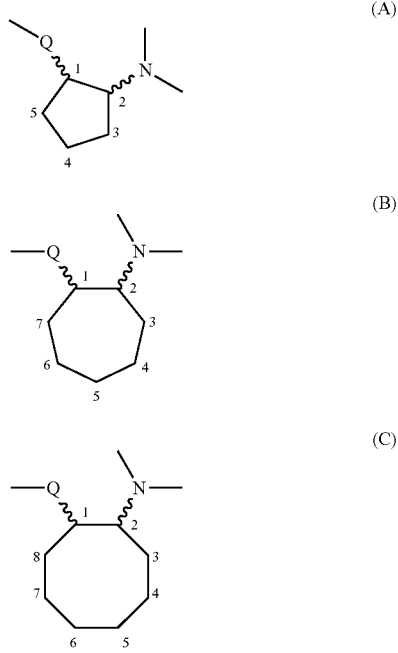

The bonds from the cycloalkyl ring to the 1-oxygen and 2-nitrogen atoms in the above formula may be relatively disposed in either a cis or trans relationship. In one version, the stereochemistry of the amine and ether substituents of the cycloalkyl ring is either (R,R)-trans or (S,S)-trans. In another version, the stereochemistry is either (R,S)-cis or (S,R)-cis.

In one version of the amino cycloalkyl ether ion channel modulating compounds, the ion channel modulating compound is a compound of formula (IXXX):

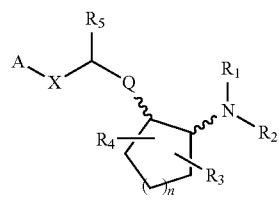

(IXXX)

wherein the substituents A, $R^1$, $R^2$, $R^3$, $R^4$, $R^5$ and X are as described above for formula (I) and wherein Q is an ether oxygen atom (Q=O in formula (IXXX)) and wherein n is 1, 3 or 4 such that a cyclopentyl, cycloheptyl or cyclooctyl ring is provided.

Compounds of formula (IXXX) are cycloalkylamines such as aminocycloalkyl ethers. More specifically, these aminocycloalkyl ethers are substituted at position 2 of a cycloalkyl ring with an amine group —$NR_1R_2$. The C-1 position is an ether (Q=O in formula (IXXX)). The cycloalkyl ring may also be substituted with additional substituents (designated as $R_3$ and $R_4$) as described in more detail below. In formula (IXXX), n is selected from 1, 3 and 4, and represents a number of carbon atoms such that when n equals 1, the ring shown in Formula (IXXX) is a substituted cyclopentane (i.e., a cyclopentyl group), when n equals 3, the ring shown in Formula (IXXX is a substituted cycloheptane (i.e., a cycloheptyl group), and when n equals 4, the ring shown in Formula (IXXX) is a substituted cyclooctane (i.e., a cyclooctyl group). Examples of specific compounds represented by formula (IXXX) are described below Depending upon the selection of substituents $R_1$ and $R_2$, the compounds of formula (IXXX) may be primary, secondary, or tertiary amines (i.e., both $R_1$ and $R_2$ are hydrogen, only one of $R_1$ and $R_2$ is hydrogen, or neither of $R_1$ and $R_2$ are hydrogen, respectively). Where the amine is tertiary, it may be a cyclic amine. Amine substituents $R_1$ and $R_2$ may be independently selected from substituents which include hydrogen, alkyl groups containing from one to eight carbon atoms (i.e., $C_1$-$C_8$alkyl), alkoxyalkyl groups containing from three to eight carbon atoms (i.e., $C_3$-$C_8$alkoxyalkyl), alkyl groups containing from one to eight carbon atoms where one of the carbon atoms is substituted with a hydroxyl group (i.e., $C_1$-$C_8$hydroxyalkyl), and aralkyl groups containing from seven to twelve carbon atoms (i.e., $C_7$-$C_{12}$aralkyl).

Alternatively, $R_1$ and $R_2$, when taken together with the nitrogen atom to which they are directly attached in formula (IXXX), may form a ring denoted by formula (II):

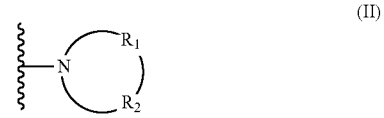

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur (e.g., an acetal, thioacetal, ketal, or thioketal group); and any two adjacent additional carbon ring atoms may be fused to a $C_3$-$C_8$-carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl. Examples of substituents containing a fused ring system include the perhydroindolyl and 1,2,3,4-tetrahydroisoquinolinyl groups.

In connection with the ring of formula (II), any two adjacent ring atoms may be joined together by single or double bonds. Thus, the ring of formula (II) may be saturated or unsaturated, and an unsaturated ring may contain one, or more than one, sites of unsaturation. In other words, the ring of formula (II) may contain one or more double bonds, it being understood, however, that the unsaturated ring of formula (II) is chemically stable.

Alternatively, $R_1$ and $R_2$, when taken together with the 2-amino nitrogen of formula (IXXX), may complete a bicyclic ring. Bicyclic rings include, for example, 3-azabicyclo[3.2.2]nonane, 2-azabicyclo[2.2.2]octane, 3-azabicyclo[3.1.0]hexane, and 3-azabicyclo[3.2.0]heptane. For these derivatives, the C-2 substituents of the cycloalkyl ethers of formula (I) are the following groups: 3-azabicyclo[3.2.2]nonan-3-yl, 2-azabicyclo-[2.2.2]octan-2-yl, 3-azabicyclo[3.1.0]hexan-3-yl, and 3-azabicyclo[3.2.0]heptan-3-yl.

Preferably for formula (II), $R_1$ and $R_2$, when taken together, contain only a single heteroatom. Preferred heteroatoms include nitrogen, oxygen and sulfur. An example of a ring in which $R_1$ and $R_2$ together include an oxygen heteroatom is the morpholinyl group. An example of a ring where $R_1$ and $R_2$ together include a second nitrogen heteroatom is the piperazinyl group.

Cycloalkyl substituents $R_3$ and $R_4$ may be independently attached to any of the ring positions except positions 1 and 2 (e.g., both $R_3$ and $R_4$ may be attached to the same ring position or each attached to different ring positions). $R_3$ and $R_4$ are independently selected from hydrogen, hydroxy, $C_1$-$C_6$alkyl, and $C_1$-$C_6$alkoxy, and, when both $R_3$ and $R_4$ are attached to the same cycloalkyl ring atom, may together form a spiro five- or six-membered heterocyclic ring containing one or two heteroatoms selected from oxygen and sulfur. Preferred heterocyclic substituents contain either a single oxygen or a single sulfur ring atom.

Depending upon the identity of X, the ether sidechain, —CH($R_5$)—X-A, in formula (IXXX) may take several forms. For example, a compound of formula (IXXX) may have X as a —C($R_6$,$R_{14}$)—Y— group, where Y may be any of a direct bond, an oxygen atom (O), a sulfur atom (S) or a $C_1$-$C_4$alkylene group. $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl. Thus, compounds of the invention include compounds of formula (IXXX) where $R_6$ and $R_{14}$ are hydrogen and Y is a direct bond, such that X may be $CH_2$.

Alternatively, X may be an alkenylene moiety, e.g., a cis- or trans-alkenylene moiety, C($R_{13}$)=CH, where $R_{13}$ may be any of hydrogen, $C_1$-$C_6$alkyl, $C_3$-$C_8$cycloalkyl, aryl or benzyl. For compounds of formula (IXXX) where X is an alkenylene moiety, X is preferably a trans-alkenylene moiety.

Alternatively, X may be a direct bond. Independent of the selections for A, X and other variables, $R_5$ is selected from hydrogen, $C_1$-$C_6$alkyl, aryl and benzyl.

Ether sidechain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_5$-$C_{12}$alkyl and $C_3$-$C_{13}$-carbocyclic rings. Particularly preferred cyclic hydrocarbons include selected aromatic groups such as phenyl, 1-naphthyl, 2-naphthyl, indenyl, acenaphthyl, and fluorenyl and are represented by formulae (III), (IV), (V), (VI), (VII), or (VIII) respectively.

A suitable "A" group within the compounds of the present invention is a phenyl ring represented by formula (III):

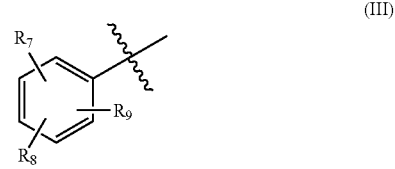

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, aryl and N($R_{15}$,$R_{16}$) where $R_{15}$ and $R_{16}$ are independently selected from hydrogen, acetyl, methanesulfonyl, and $C_1$-$C_6$alkyl.

For compounds of formula (IXXX) where X is a direct bond or $CH_2$, at least one of $R_7$, $R_8$ and $R_9$ is preferably selected from amine (—NR$_{15}$R$_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$alkyl, $C_1$-$C_6$alkoxy, $C_2$-$C_7$alkylcarbonyl, $C_1$-$C_6$thioalkyl or aryl groups. For compounds of formula (I) when X is CH=CH, and $R_3$ and $R_4$ are hydrogen, at least one of $R_7$, $R_8$ and $R_9$ is preferably a substituent other than hydrogen.

Other suitable "A" groups in compounds of the present invention are 1-naphthyl groups as represented by formula (IV):

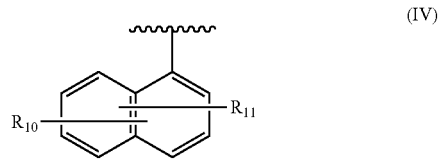

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$,$R_{16}$) where $R_{15}$ and $R_{16}$ are independently selected from hydrogen, acetyl, methanesulfonyl, and $C_1$-$C_6$alkyl.

Other suitable "A" groups in compounds of the present invention are 2-naphthyl group as represented by formula (V):

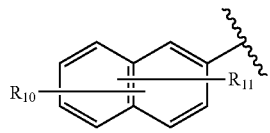

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl, as defined above.

Other suitable "A" groups in compounds of the present invention are aromatic groups represented by formula (VI):

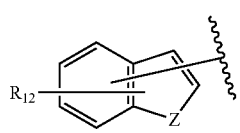

(IV)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl.

The aryl groups of formula (VI) are derivatives of indene, indole, benzofuran, and thianaphthene when Z is methylene, nitrogen, oxygen, and sulfur, respectively. Preferred heterocyclic groups of formula (VI) include indole where Z is NH, benzofuran where Z is O, and thianaphthene where Z is S. As described below, in a preferred embodiment, Z is O, S or N—$R_{17}$, and in a particularly preferred embodiment Z is O or S.

Another suitable "A" group in compounds of the present invention are acenaphthyl groups as represented by formula (VII):

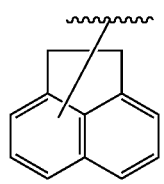

(VII)

Still another suitable "A" group in compounds of the present invention is the fluorenyl group represented by formula (VIII):

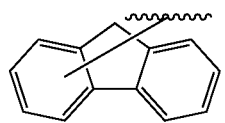

(VIII)

Preferably, ether sidechain component A is an acenapthyl or fluorenyl group only when X is a direct bond or $CH_2$. In other variations, the acenaphthyl group is a 1-acenaphthyl group, and the fluorenyl group is a 9-fluorenyl group.

In another variation of (IXXX), X is $(CH_2)$—Y. For these variations, Y is a direct bond, an oxygen atom, or a sulfur atom. In a particular variation, Y is a direct bond or an oxygen atom. In another variation, Y is a direct bond and X is $C(R_6, R_{14})$, where $R_6$ and $R_{14}$ are as defined above. In another variation, X is $C(R_{13})$=CH, and $R_{13}$ is a hydrogen atom. For these variations, $R_3$ and $R_4$ are preferably independently attached to the cycloalkyl ring at the 4- or 5-positions.

Ion channel modulating compounds of formula (IXXX) may be provided, wherein: independently at each occurrence,
  n is selected from 1, 3 and 4;
  Q is either O (oxygen) or —O—C(O);
  X is selected from a direct bond, —C($R_6,R_{14}$)—Y— and —C($R_{13}$)=CH—;
  Y is selected from a direct bond, O, S and $C_1$-$C_4$alkylene;
  $R_{13}$ is selected from hydrogen, $C_1$-$C_6$alkyl, $C_3$-$C_8$cycloalkyl, aryl and benzyl;
  $R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or
  $R_1$ and $R_2$ are independently selected from $C_3$-$C_8$alkoxyalkyl, $C_1$-$C_8$hydroxyalkyl, and $C_7$-$C_{12}$aralkyl; or
  $R_1$ and $R_2$ are taken together with the nitrogen atom to which they are directly attached in formula (IXXX) to form a ring denoted by formula (II):

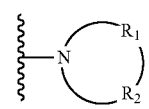

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may bear one or two substituents selected from hydrogen, hydroxyl, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may form a spiro five- or six-membered heterocyclic ring containing one or two heteroatoms selected from oxygen and sulfur; and any two adjacent additional carbon ring atoms may be fused to a $C_3$-$C_8$-carbocyclic ring, and any one or more of the additional nitrogen ring atoms may bear substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together with the nitrogen atom to which they are directly attached in formula (IXXX) to form a bicyclic ring system selected from 3-azabicyclo

[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cycloalkyl ring shown in formula (IXXX) at other than the 1 and 2 positions and are independently selected from hydrogen, hydroxyl, $C_1$-$C_6$alkyl and $C_1$-$C_6$alkoxy, and, when both $R_3$ and $R_4$ are attached to the same cycloalkyl ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$-carbocyclic ring, and ring systems selected from formulae (III), (IV), (V), (VI), (VII) and (VIII):

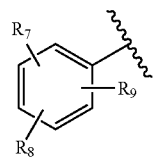
(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, aryl and $N(R_{15},R_{16})$ where $R_{15}$ and $R_{16}$ are independently selected from hydrogen, acetyl, methanesulfonyl and $C_1$-$C_6$alkyl;

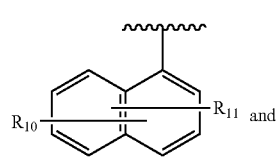
(IV)

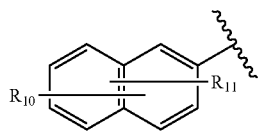
(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl;

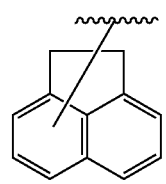
(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (IXXX) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

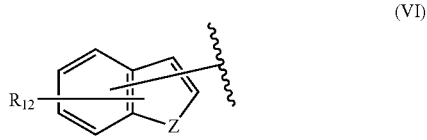
(VII)

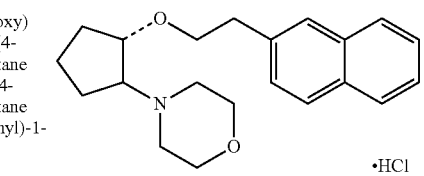
(VIII)

including isolated enantiomeric, diastereomeric and geometric isomers thereof;

In another version of the amino cycloalkyl ether ion channel modulating compounds, the ion channel modulating compound is one of the following compounds or mixtures of compounds.

(1R,2R)-2-(4-Morpholinyl)-1-(2-naphthalenethoxy) cyclopentane monohydrochloride or (1S,2S)-2-(4-Morpholinyl)-1-(2-naphthalenethoxy) cyclopentane monohydrochloride or a mixture of (1R,2R)-2-(4-Morpholinyl)-1-(2-naphthalenethoxy) cyclopentane monohydrochloride and (1S,2S)-2-(4-Morpholinyl)-1-(2-naphthalenethoxy) cyclopentane monohydrochloride

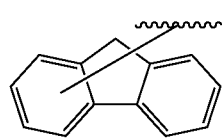
·HCl

| | |
|---|---|
| (1R,2R)-2-(3-Ketopyrrolidinyl)-1-(2,6-dichlorophenethoxy) cyclopentane monohydrochloride or (1S,2S)-2-(3-Ketopyrrolidinyl)-1-(2,6-dichlorophen ethoxy) cyclopentane monohydrochloride or a mixture of (1R,2R)-2-(3-Ketopyrrolidinyl)-1-(2,6-dichlorophenethoxy) cyclopentane monohydrochloride and (1S,2S)-2-(3-Ketopyrrolidinyl)-1-(2,6-dichlorophen ethoxy) cyclopentane monohydrochloride | 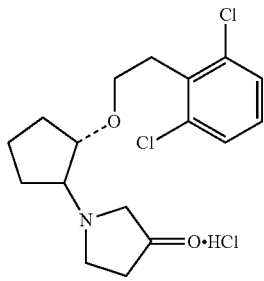 |

In another version of the amino cycloalkyl ether ion channel modulating compounds, the ion channel modulating compound is a protonated version of any of the amino cycloalkyl ether compounds described in this patent. That is, for each amino cycloalkyl ether compound described in this patent, the quaternary protonated amine form of the compound may also be considered as an amino cycloalkyl ether ion channel modulating compounds. These quaternary protenated amine form of the compounds may be present in the solid phase, for example in crystalline or amorphous form, and may be present in solution. These quaternary protenated amine form of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

General Description of Ion Channel Modulating Compounds

Generally, any compound that modulates ion channel activity may by an ion channel modulating compound. A compound that modulates ion channel activity may be a compound that increases or decreases ion channel activity. An ion channel modulating compound that decreases ion channel activity may be a compound that blocks ion channel activity completely or partially.

In another version, any compound that either singly or together with one or more additional compounds selectively inhibit certain combination of cardiac ionic currents is an ion channel modulating compound. The cardiac currents may be the sodium currents and early repolarizing currents. Ion channel modulating compounds may block cardiac currents from extracellular loci. Such compounds act on an external locus of the ion channel that is accessible from the extracellular surface. This facilitates access to the ion channel and provides rapid onset kinetics and exhibits frequency dependent blockade of currents. Such properties are all beneficial for compounds used to treat arrhythmias. An ion channel modulating compound may selectively inhibit cardiac early repolarizing currents and cardiac sodium currents. Ion channel modulating compounds may be used to selectively inhibit cardiac early repolarizing currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation. An ion channel modulating compound may be an atrial selective agent. An ion channel modulating compound may treat or prevent ventricular arrhythmia. An ion channel modulating compound block cardiac sodium currents or cardiac early repolarizing currents. An ion channel modulating compound may inhibit multiple cardiac ionic currents. An ion channel modulating compound may be used to treat or prevent arrhythmic, including ventricular or atrial arrhythmia, particularly atrial fibrillation.

The ion channel modulating compounds may block the cardiac ion channels responsible for early repolarizing currents and sodium currents; and/or block cardiac early repolarizing currents and cardiac sodium currents under conditions where an arrhythmogenic substrate is present in the heart; and/or block the cardiac ion channels responsible for early repolarizing currents and sodium currents under conditions where an arrhythmogenic substrate is present in the heart; and/or block cardiac early repolarizing currents and cardiac sodium currents from extracellular loci in cardiac cells.

In one variation, the cardiac early repolarizing currents referred to above comprise ionic currents which activate rapidly after depolarization of membrane voltage and which effect repolarization of the cell. The early repolarizing currents may comprise the cardiac transient outward potassium current ($I_{to}$) and/or the ultrarapid delay rectifier current ($I_{Kur}$). The cardiac transient outward potassium current ($I_{to}$) and/or the ultrarapid delay rectifier current ($I_{Kur}$) may comprise at least one of the Kv4.2, Kv4.3, Kv2.1, Kv1.4 and Kv1.5 currents.

Ion channel modulating compounds may generally have any pKa, however ion channel modulating compounds typically have pKa values of between 4-9, and may have pKa values that are less than 8, including pKa values between 5-7.5. Methods to determine pKa values are well known in the art (see, e.g., Perrin, "Dissociation Constants of Organic Bases in Aqueous Solution", Butterworth, London, 1972). For ion channel modulating compounds with the specific ranges of pKa described above, the fraction of the charged (protonated) species will be increased under the pathological conditions such as cardiac arrhythmias and the presence of an arrhythmogenic substrate in the heart as described above due to the increase in cardiac milieu acidity. Where the charged form of a compound is active, its potency increases under conditions associated with an increases in cardiac milieu acidity.

Particular ion channel modulating compounds have structural characteristics that may be determined by various physical methods, such as single crystal X-ray crystallography. For instance, some ion channel modulating compounds comprise a cycloalkane ring and substituents J and K as shown below in structure T, wherein the relative positions of J and K provide a "C" shaped angle and wherein n=1, 2, 3 or 4.

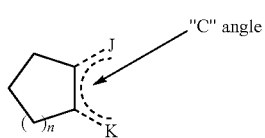

(T)

Typically, one of J and K comprises a hydrophobic moiety, such as but not limited to a moiety comprising alkyl and/or aryl moieties. In one variation, one of J and K comprises a hydrophobic aromatic moiety, which may be attached to the cycloalkane ring of structure T via an ether bond. Typically, one of J and K comprises a hydrophilic moiety, such as a heteroatom containing moiety, including but not limited to a nitrogen containing moiety that is available to form a quaternary salt and/or a hydroxyl moiety. In one variation, one of J and K comprises a nitrogen containing moiety substituted with a hydroxyl moiety or the like, such as a pyrrolidinyl moiety. In a particular variation of structure T, n=2, J comprises a aromatic moiety and K comprises a nitrogen containing moiety substituted with a hydroxyl moiety or the like. The cycloalkane ring may be optionally substituted. In one version, the cycloalkane ring may be replaced by a structural moiety imparting rigidity to the relative positions of the J and K groups. For example if the J and K groups are attached to atoms L and M that are directly bonded to each other, any group that does not allow substantial rotation about the bond between atoms L and M can impart rigidity to the relative positions of the J and K groups. For example, the ion channel modulating compound may be a compound of formula

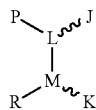

where J and K are as described above and groups P and R are moieties such that there is not substantial rotation about the L-M bond. In one example P and Q taken together form a cyclic moiety that prevents substantial rotation about the L-M bond.

In one version, the ion channel modulating compound comprises an amino substituted 5, 6, 7 or 8-membered ring, which may be a 5, 6, 7, or 8-membered substituted or unsubstituted cycloalkyl ring. The amino substituted cycloalkane ring may be an aminocyclohexyl ring and may be further substituted with one or more additional moieties. In one version, the amino substituted cycloalkane ring is further substituted with an ether moiety. In some instances, the ion channel modulating compound comprises an aminocyclohexyl ring that is further substituted with an ether moiety.

In another, the ion channel modulating compound is a protenated version of any of the ion channel modulating compounds described in this patent. That is, for each ion channel modulating compound described in this patent, the quaternary protenated amine form of the compound may also be considered as an amino ion channel modulating compound. These quaternary protenated amine form of the compounds may be present in the solid phase, for example in crystalline or amorphous form, and may be present in solution. These quaternary protenated amine form of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002

Methods of Making Antiarrhythmic Compounds

Methods that may be used to synthesize the ion channel modulating compounds described in this section are described in PCT/US03/34655 (filed Oct. 31, 2003), U.S. 60/516,248 (filed Oct. 31, 2003), WO 99/50225, and WO 00/47547 each of which is incorporated herein by reference in its entirety.

In one method, illustrated in FIG. 1, compounds are prepared by a Williamson ether synthesis (Feuer, H.; Hooz, J. Methods of Formation of the Ether Linkage. In Patai, Wiley: New York, 1967; pp 445-492) between an activated form of aminoalcohol 4R with the alkoxide of 3,4-dimethoxyphenethyl alcohol in a polar solvent such as dimethoxyethane (ethylene glycol dimethyl ether) (DME) (FIG. 1) that provided the corresponding aminoether 5R in high yield. Subsequent resolution of the diastereomers such as by chromatographic separation (e.g. HPLC) to afford 5RRR and 5SSR followed by hydrogenolysis provided compound 1 and compound 2 respectively.

(1R,2R)-2-[(3S)-Hydroxypyrrolidinyl]-1-(3,4-dimethoxyphenethoxy)cyclohexane free base and the corresponding monohydrochloride (compound 6) and (1S,2S)-2-[(3S)-hydroxy-pyrrolidinyl]-1-(3,4-dimethoxyphenethoxy)cyclohexane free base and the corresponding monohydrochloride (compound 7) are obtained using a similar synthetic sequence but starting with 3-(S)-hydroxypyrrolidine.

Hydrogenolysis of (1R,2R)/(1S,2S)-2-[(3R)-benzyloxypyrrolidinyl]-1-(3,4-dimethoxyphenethoxy)cyclohexane (5R) provided (1R,2R)/(1S,2S)-2-[(3R)-hydroxypyrrolidinyl]-1-(3,4-dimethoxyphenethoxy)cyclohexane free base and the corresponding monohydrochloride (compound 4). Similarly, starting with 3-(S)-hydroxypyrrolidine instead of 3-(R)-hydroxypyrrolidine and following the same synthetic sequence will afford (1R,2R)/(1S,2S)-2-[(3S)-benzyloxypyrrolidinyl]-1-(3,4-dimethoxyphenethoxy)cyclohexane. The latter on hydrogenolysis will provide (1R,2R)/(1S,2S)-2-[(3S)-hydroxypyrrolidinyl]-1-(3,4-dimethoxyphenethoxy) cyclohexane free base and the corresponding monohydrochloride (compound 5). (1R,2R)/(1S,2S)-2-[(3R)/(3S)-Hydroxypyrrolidinyl]-1-(3,4-dimethoxyphenethoxy)-cyclohexane free base and the corresponding monohydrochloride (compound 3) can also be synthesized by similar process by starting with racemic 3-hydroxypyrrolidine.

Formulations, Routes of Administration and Dosage Forms

In this section are described general formulations, routes of administration, and dosage forms that may be used in the methods described in this patent. Specific formulations, routes of administration, and dosage forms that may be used for treating, preventing, and postponing onset of arrhythmia are described in more detail in the Method of Treating Arrhythmia and Method of Preventing or Postponing Onset of Arrhythmia sections.

Formulation and Routes of Administration

The ion channel modulating compounds and formulations described herein may be formulated in a dosage form suitable for oral, parenteral, mucosal, nasal, sublingual, transdermal, buccal, topical, vaginal, rectal, ocular or other administration. An ion channel modulating compounds as described herein may be in the form of an immediate and/or modified release formulation or it may be designed to release the ion channel modulating compound in a relatively fast manner in order to enable a relatively fast onset of the therapeutic effect. As used herein "compounds" and "compositions" of ion channel modulating compounds includes the ion channel modulating compounds as described herein alone or in combination with other materials, as described below.

Dosage Forms and Dosage Amounts and Dosage Frequency

In general, the amount of the ion channel modulating compound present in a composition depends inter alia on the specific ion channel modulating compound and formulation, the age and condition of the subject, and the disease or conditions to be treated and/or prevented, the route of administration, and the dosage frequency.

The dosage frequency also depends on the disease or condition to be treated and/or prevented, amount or concentration of the ion channel modulating compound, the specific composition used, the route of administration, and may incorporate subject-specific variation including, but not limited to age, weight, gender, genetic background, and overall health. For example, a nasal formulation may be administered once daily e.g. in order to achieve a relatively fast onset of the therapeutic effect, or it may be administered more often. The same criteria for selecting dosage frequency applies to other dosage forms including but not limited to a plain tablet composition, a buccal composition, a rectal composition, an oral composition, a topical composition, an ocular composition, or other compositions.

Formulations of the ion channel modulating compound can be used to provide controlled release ("controlled release formulations") in which the release of the ion channel modulating compound is controlled and regulated to allow less frequency of dosing or to improve the pharmacokinetic or toxicity profile of a given active ingredient.

A controlled release formulation as described herein may allow dosage once, twice, or three or more times daily in order to obtain a suitable therapeutic effect. Controlled release may also include continuous and/or sustained release, for example, as from an implantable device. Pulsatile release may also be desirable. Administration may comprise co-administration of more than one dosage unit, such as, e.g. 2-4 dosage units.

Typically, the ion channel modulating compounds described herein are formulated for use in humans. Ion channel modulating compounds can also include veterinary formulations, e.g., pharmaceutical preparations suitable for veterinary uses, e.g., for the treatment of livestock or domestic animals, e.g., dogs, cats, racehorses, etc.

Actual dosage levels of the ion channel modulating compound in the formulations of the ion channel modulating compounds described herein may be varied so as to obtain an amount of the ion channel modulating compound which is effective to achieve the desired therapeutic effect for a particular subject, ion channel modulating compound, and mode of administration, without being toxic to the subject.

The selected dosage level will depend upon a variety of factors including but not limited to the activity of the ion channel modulating compound (or the ester, salt, amide or formulation thereof); the route of administration; the time of administration; the rate of excretion of the particular ion channel modulating compound being employed; the duration of the treatment; other drugs, compounds and/or materials used in combination with the ion channel modulating compound described herein; the age, sex, weight, condition, general health and prior medical history of the subject being treated; and like factors well known in the medical arts.

A physician or veterinarian having ordinary skill in the art can readily determine and prescribe the effective amount of the pharmaceutical composition required. For example, the physician or veterinarian could start doses of the ion channel modulating compound at levels lower than that required in order to achieve the desired therapeutic effect and gradually increase the dosage until the desired therapeutic effect is achieved.

In general, a suitable dose of an ion channel modulating compound will be the lowest dose effective to produce a therapeutic effect. Such an effective dose will generally depend upon the factors described above. Preferred formulations include oral (immediate or quick release forms) and intravenous forms (IV), nasal forms, sublingual and metered dose inhaler forms. Generally, intravenous and oral forms of the ion channel modulating compound for a subject will range from about 0.1 to about 50 mg per kilogram of body weight per day. For ion channel modulating compound such as the aminocyclohexyl ether compound (1R,2R)-2-[(3R)-hydroxypyrrolidinyl]-1-(3,4-dimethoxyphenethoxy)cyclohexane monohydrochloride, a therapeutic dosage for the intravenous form may be from about 0.1 to about 10 mg per kilogram. Another suitable dosage of (1R,2R)-2-[(3R)-hydroxypyrrolidinyl]-1-(3,4-dimethoxyphenethoxy)cyclohexane monohydrochloride for the intravenous form may be from about 2 to about 5 mg per kilogram. For ion channel modulating compound such as the aminocyclohexyl ether compound (1R,2R)-2-[(3R)-hydroxypyrrolidinyl]-1-(3,4-dimethoxyphenethoxy)cyclohexane monohydrochloride, a therapeutic dosage for oral administration may be from about 30 to about 1800 mg tablets or capsules b.i.d. Another suitable dosage of (1R,2R)-2-[(3R)-hydroxypyrrolidinyl]-1-(3,4-dimethoxyphenethoxy)cyclohexane monohydrochloride for oral administration may be from about 300 to about 900 mg tablets or capsules b.i.d.

Intranasal formulations and patch formulations are also preferred forms. Generally, intranasal formulations and patch formulations of the ion channel modulating compound for a subject will range from about 0.1 to about 100 mg per kilogram of body weight per day, preferably from about 0.1 to about 10 mg per kilogram, even more preferably from about 1 to about 10 mg per kilogram.

The effective dose of the ion channel modulating compound may be administered as two, three, four, five, six or more sub-doses administered separately at appropriate intervals throughout the day, optionally, in unit dosage forms.

The subject receiving this treatment is any animal in need, including primates, in particular humans, and other mammals such as equines, cattle, swine and sheep; and poultry and pets such as dogs and cats among others in general.

Routes of Administration

The ion channel modulating compound described herein may be administered to a subject by any route capable of delivering a therapeutically effective amount of the compound including but not limited to administration by oral, parenteral, intracranial, intraorbital, intracapsular, intraspinal, intracisternal, intrapulmonary, intravenous, intramuscular, intra-arterial, intramedullary, intrathecal, intraventricular, transdermal, subcutaneous, intraperitoneal, intranasal, enteral, topical, sublingual, buccal, gingival, palatal or rectal means.

Typically, the ion channel modulating compound is given in forms suitable for each administration route. For example, the ion channel modulating compound may be administered parenterally by injection, infusion or inhalation; administered topically by lotion or ointment; or administered rectally by suppositories. Typical forms of administration described herein are not intended to be either limiting or exhaustive, but merely illustrative.

The phrases "parenteral administration" and "administered parenterally" as used herein mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration," or "administered systemically," as used herein mean the administration of a compound, drug or other material such as the ion modulating compound so that it enters the subject's system by a direct route or parenteral route and thus is subject to metabolism and other like processes (for example, by subcutaneous administration). The phrases "peripheral administration" and "administered peripherally" as used herein mean the administration of a compound, drug or other material such as the ion modulating compound so that it enters the subject's system by an indirect or localized route and thus is subject to metabolism and other like processes (for example, by topical administration).

Regardless of the route of administration, the ion channel modulating compounds described herein can be formulated into pharmaceutically acceptable dosage forms such as described, or other dosage forms known to those of skill in the art.

The phrase "pharmaceutically acceptable" as used herein can refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The ion channel modulating compounds can be administered alone or in admixtures with pharmaceutically acceptable and/or sterile carriers and can also be administered in conjunction with other drugs (e.g. other cardiovascular agents, antimicrobial agents, etc.). Multiple routes of simultaneous or sequential administration (e.g. oral and transdermal) are also contemplated.

Formulations

Formulations of ion channel modulating compounds can be formulated in any manner suitable for a desired delivery route. Typically, formulations include all physiologically acceptable compositions. Such formulations may include one or more ion channel modulating compounds by itself or in combination with any physiologically acceptable carrier or carriers. The formulation may also enhance, alter, or modify the effect or the ion channel modulating compound and/or physiological milieu of the ion channel modulating compound.

While it is possible for an ion channel modulating compound to be administered alone, it is preferable to administer the ion channel modulating compounds as a pharmaceutical formulation including other materials. The ion channel modulating compounds may be formulated for administration in any way for use in human or veterinary medicine. The ion channel modulating compound may be active itself, or may be a prodrug, e.g., capable of being converted to an active compound in a physiological setting.

The ion channel modulating compounds described herein may provide pharmaceutically acceptable formulations with therapeutically effective amounts of one or more of ion channel modulating compounds, formulated with one or more pharmaceutically acceptable carriers (additives), other active agents, and/or diluents. Formulations of ion channel modulating compounds may be for administration in solid, liquid, vapor, or suspension form, including those adapted for oral administration, for example, drenches (aqueous or non-aqueous solutions or suspensions), tablets, boluses, powders, granules, polymer release formulations, pastes for application to the tongue; parenteral administration, for example, by subcutaneous, intramuscular or intravenous injection as, for example, a sterile solution or suspension; topical application, for example, as a cream, ointment or spray applied to the skin; or intravaginally or intrarectally, for example, as a pessary, suppository, cream or foam. However, in certain embodiments the subject compounds may be simply dissolved or suspended in sterile water.

Ion channel modulating compounds as described herein may be formulated for administration with any biologically acceptable medium, including but not limited to water, buffered saline, polyol (for example, glycerol, propylene glycol, liquid polyethylene glycol and the like) or suitable mixtures thereof. The optimum concentration of the ion channel modulating compound in the chosen medium can be determined empirically, according to procedures well known in the art. As used herein, "biologically acceptable medium" includes any and all solvents, dispersion media, and the like which may be appropriate for the desired route of administration of the pharmaceutical preparation. The use of a biologically acceptable medium for pharmaceutically active substances is known in the art. Suitable biologically acceptable media and their formulation are described, for example, in the most recent version of Remington's Pharmaceutical Sciences (Remington's Pharmaceutical Sciences. Mack Publishing Company, Easton, Pa., USA 1985).

Formulations may contain suitable physiologically acceptable carriers comprising excipients and/or auxiliaries which facilitate processing of the ion channel modulating compounds into preparations which can be used pharmaceutically. Formulations of the ion channel modulating compounds may also include agents which increase or otherwise affect the bioavailability of the drug. As used herein, "bioavailability" refers to the effect, availability and persistence of the ion channel modulating compound after being administered to a subject.

Pharmaceutically acceptable carriers can be any pharmaceutically acceptable material, composition, or vehicle, including but not limited to a liquid or solid filler, diluent, excipient, solvent or encapsulating material, involved in carrying or transporting the subject agonists to an organ, or portion of the body. Each carrier must be compatible with the other ingredients of the formulation and not injurious to the subject. Some examples of materials which can serve as pharmaceutically acceptable carriers include but are not limited to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

The ion channel modulating compound may be capable of forming pharmaceutically acceptable salts such as inorganic and organic acid or base addition salts of the ion channel modulating compounds described herein. (See, for example, Berge et al. (1977) "Pharmaceutical Salts", J. Pharm. Sci. 66:1-19). In particular, HCl salts of the ion channel modulating compounds may be used. Other salt forms include hydrochloride, hydrobromide, hydroiodide, bisulphate, acid citrate, bitartrate, ethansulphonate, sulphate, phosphate or acid phosphate, acetate, maleate, fumarate, lactate, tartrate, L-tartrate, citrate, gluconate, benzenesulphonate (besylate), p-toluenesulphonate (tosylate), methanesulphonate (mesylate), esylate, succinate, salicylate, nitrate, sulfate, etc.

Formulations of the ion channel modulating compounds can also include wetting agents; emulsifiers and lubricants such as sodium lauryl sulfate and magnesium stearate; coloring agents; release agents; coating agents; sweetening, flavoring, and/or perfuming agents; preservatives; and antioxidants.

Examples of pharmaceutically acceptable antioxidants include but are not limited to water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of ion channel modulating compounds may also incorporate buffering agents and/or salts to aid absorption or stabilize the ion channel modulating compound. Other additives, such as chelating agents, enzymatic inhibitors, and the like, which would facilitate the biological activity of the pharmaceutical composition may also be incorporated in the formulation. Formulations of ion channel modulating compounds may also contain opacifying agents.

The formulations of ion channel modulating compounds may be presented in unit dosage form and may be prepared by any methods known in the art. The amount of ion channel modulating compound that can be combined with a carrier material to produce a single dosage form may vary. For example, the amount of ion channel modulating compound in a given formulation may depend upon the host being treated and/or the particular mode of administration. The amount of ion channel modulating compound which can be combined with a carrier to produce a single dosage form will generally be that amount of the ion channel modulating compound which produces a therapeutic effect.

Methods of preparing these formulations include the step of bringing into association an ion channel modulating compound with the carrier and/or one or more accessory ingredients. Some formulations may be prepared by bringing an ion channel modulating compound in association with liquid carriers, finely divided solid carriers, or both, and then shaping the product.

Formulations of the ion channel modulating compound suitable for oral administration may be in the form of a solid (capsules, cachets, pills, tablets, lozenges, powders, dragees, granules); or as a solution or a suspension in an aqueous or non-aqueous liquid; or as an oil-in-water or water-in-oil liquid emulsion; or as an elixir or syrup; or as pastilles (using an inert base, such as gelatin and glycerin, or sucrose and acacia); and/or as mouth rinses or washes and the like; or as a bolus, electuary or paste.

Solid formulations of ion channel modifying compounds may have pharmaceutically acceptable carriers and extenders including but not limited to sodium citrate or dicalcium phosphate; starches; lactose; sucrose; glucose; mannitol; and/or silicic acid. Solid formulations of the ion channel modulating compound can include additional components including but not limited to binders such as carboxymethylcellulose, alginates, gelatin, polyvinyl pyrrolidone, sucrose and/or acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as cetyl alcohol and glycerol monostearate; absorbents such as kaolin and bentonite clay; lubricants such a talc, calcium stearate, magnesium stearate, solid polyethylene glycols, sodium lauryl sulfate, and mixtures thereof; and coloring agents. The formulation may also include buffering agents, particularly when the ion channel modulating compound is in the form of a capsule, tablet or pill.

Solid formulations may also include fillers for soft and hard-filled gelatin capsules using excipients such as lactose or milk sugars, as well as high molecular weight polyethylene glycols and the like.

Solid formulations such as pills and tablets may be formed by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of powdered ion channel modulating compound moistened with an inert liquid diluent.

Solid formulations of ion channel modulating compounds described herein, such as dragees, capsules, pills and granules, may optionally be scored or prepared with coatings and shells, such as enteric coatings and other coatings. Solid dosage forms may also be formulated so as to provide slow or controlled release of the ion channel modulating compound. Thus, solid formulations could include any material that could provide a desired release profile of the ion channel modulating compound, including but not limited to hydroxypropylmethyl cellulose in varying proportions, or other polymer matrices, liposomes and/or microspheres.

Formulations of ion channel modulating compounds may also be formulated to release the ion channel modulating compound only, or preferentially, in a certain portion of the gastrointestinal tract, for example, by including an embedding agent. Examples of embedding agents which can be used include but are not limited to polymeric substances and waxes. The ion channel modulating compound may also be in microencapsulated form, if appropriate, with one or more of the above-described excipients.

Coated or encapsulating formulations of ion channel modulating compounds may also be formulated to deliver pulsatile, sustained, or extended release. For example one method of pulsatile release could be achieved by layering multiple coatings of ion channel modulating compound, or by incorporating the ion channel modulating compound within different regions of the formulation having different release times.

Other example of methods and materials for pulsatile delivery include, but are not limited to those described in the patent documents listed below and the patents and publications referenced therein, all of which are incorporated by reference herein.

| U.S. Pat. No. | |
|---|---|
| 6,645,524 | Oral pharmaceutical dosage forms for pulsatile delivery of an antiarrhythmic agent |
| 6,635,277 | Composition for pulsatile delivery of diltiazem and process of manufacture |
| 6,627,223 | Timed pulsatile drug delivery systems |
| 6,607,751 | Controlled release delivery device for pharmaceutical agents incorporating microbial polysaccharide gum |
| 6,596,314 | Controlled release liquid active agent formulation dosage forms |
| 6,555,136 | Pharmaceutical dosage form for pulsatile delivery of methylphenidate |
| 6,500,457 | Oral pharmaceutical dosage forms for pulsatile delivery of an antiarrhythmic agent |
| 6,461,331 | Device and method for infusion of small molecule insulin mimetic materials |
| 6,387,037 | Implantable heart assist system and method of applying same |
| 6,372,254 | Press coated, pulsatile drug delivery system suitable for oral administration |
| 6,342,249 | Controlled release liquid active agent formulation dosage forms |
| 6,340,476 | Pharmaceutical dosage form for pulsatile delivery of methylphenidate |
| 6,312,409 | Device for generating a pulsatile fluid drug flow |
| 6,217,904 | Pharmaceutical dosage form for pulsatile delivery of d-threo-methylphenidate and a second CNS stimulant |
| 6,214,377 | Melatonin for the production of a peroral pulsatile form of medication |
| 6,117,450 | Method of making a perorally administered solid drug with controlled effective ingredient delivery |
| 6,080,721 | Pulmonary delivery of active fragments of parathyroid hormone |
| 5,965,521 | Pulsatile delivery of leptin receptor ligands |
| 5,840,329 | Pulsatile drug delivery system |
| 5,814,607 | Pulmonary delivery of active fragments of parathyroid hormone |
| 5,716,318 | Method of treating cardiac arrest and apparatus for same |
| 5,607,915 | Pulmonary delivery of active fragments of parathyroid hormone |
| 5,456,679 | Delivery devices with pulsatile effect |
| 5,318,558 | Osmotically driven delivery device with expandable orifice for pulsatile delivery effect |
| 4,698,062 | Medical device for pulsatile transdermal delivery of biologically active agents |
| 4,687,423 | Electrochemically-driven pulsatile drug dispenser |
| 4,525,165 | Fluid handling system for medication infusion system |
| U.S. patent application Ser. No. | |
| 20030203029 | Controlled release liquid active agent formulation dosage forms |
| 20030194439 | Pharmaceutical dosage form for pulsatile delivery of methylphenidate |
| 20030171282 | Pulmonary delivery of active fragments of parathyroid hormone |
| 20030170181 | Method for preventing abuse of methylphenidate |
| 20030003149 | Composition for pulsatile delivery of diltiazem and process of manufacture |
| 20020098232 | Oral pharmaceutical dosage forms for pulsatile delivery of an antiarrhythmic agent |
| 20020086055 | Controlled release liquid active agent formulation dosage forms |
| 20020082680 | Expandable medical device for delivery of beneficial agent |
| 20020058061 | Pharmaceutical dosage form for pulsatile delivery of methylphenidate |
| 20020007139 | Medical infusion and aspiration system |
| 20010046964 | Timed pulsatile drug delivery systems |

Liquid dosage formulations for oral administration of the ion channel modulating compounds may include pharmaceutically acceptable emulsions, microemulsions, solutions, suspensions, syrups and elixirs. In addition to the ion channel modulating compound, the liquid dosage formulations may contain inert diluents commonly used in the art, including but not limited to water or other solvents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol; oils (in particular, cottonseed, groundnut, corn, germ, olive, castor and sesame oils); glycerol; tetrahydrofuryl alcohol; polyethylene glycols; and fatty acid esters of sorbitan, and mixtures thereof.

The ion channel modulating compound may also be formulated as a suspension. Suspensions of the ion channel modulating compound may include suspending agents. Examples of suspending agents include but are not limited to ethoxylated isostearyl alcohols; polyoxyethylene sorbitol and sorbitan esters; microcrystalline cellulose; aluminum metahydroxide; bentonite; agar-agar; tragacanth; and mixtures thereof.

Formulations of the ion channel modulating compound for rectal or vaginal administration may be presented as a suppository. Suppository formulations may be prepared by mixing one or more ion channel modulating compounds with one or more suitable nonirritating excipients or carriers. Suitable carriers include any compound which is solid at room temperature but liquid at body temperature, and therefore will melt in the rectum or vaginal cavity and release the ion channel modulating compound. Examples of such carriers include but are not limited to cocoa butter; polyethylene glycol; a suppository wax or a salicylate.

Formulations of the ion channel modulating compound suitable for vaginal administration also include pessaries, tampons, creams, gels, pastes, foams or spray formulations containing such carriers as are known in the art.

Formulations of the ion channel modulating compound suitable for the topical or transdermal administration include powders, sprays, ointments, pastes, creams, lotions, gels, solutions, patches and inhalants. The ion channel modulating compound may be mixed under sterile conditions with a pharmaceutically acceptable carrier, and with any preservatives, buffers, or propellants which may be required.

Powders and sprays may contain, in addition to an ion channel modulating compound, excipients such as lactose, talc, silicic acid, aluminum hydroxide, calcium silicates and polyamide powder, or mixtures of these substances. Sprays may contain customary propellants, such as chlorofluorohydrocarbons and volatile unsubstituted hydrocarbons, such as butane and propane.

The ion channel modulating compound may also be formulated as a transdermal patch. Transdermal patches have the added advantage of providing controlled delivery of the ion channel modulating compound into the body. Such formulations may be made by dissolving or dispersing the ion channel modulating compound in the proper medium. Absorption enhancers may also be used to increase the flux of the compound across the skin. The rate of flux may be controlled. Examples of ways of controlling the rate of flux include but are not limited to rate controlling membranes or dispersing the compound in a polymer matrix or gel.

Ophthalmic formulations of the ion channel modulating compound include, but are not limited to, eye ointments, powders, solutions and the like.

Formulations of ion channel modulating compounds for parenteral administration may have one or more ion channel modulating compound in combination with one or more pharmaceutically acceptable isotonic aqueous or nonaqueous solutions, dispersions, suspensions or emulsions, or powders which may be reconstituted into sterile injectable solutions or dispersions just prior to use. Parenteral formulations may contain antioxidants; buffers or solutes which render the formulation isotonic with the blood of the intended subject; bacteriostats; suspending; or thickening agents.

Injectable depot formulations of the ion channel modulating compound can be made by forming microencapsulated matrices of the ion channel modulating compounds in biodegradable polymers. Examples of biodegradable polymers include, but are not limited to polylactide-polyglycolide, poly(orthoesters) and poly(anhydrides). The ratio of ion channel modulating compound to polymer and the nature of the particular polymer employed can affect the rate of ion channel modulating compound released. Depot injectable formulations can also be prepared by entrapping the drug in liposomes or microemulsions.

Proper fluidity of liquid, suspension and other formulations of the ion channel modulating compounds can be maintained by the use of coating materials such as lecithin; by the maintenance of the required particle size in the case of dispersions; or by the use of surfactants.

Formulations of the ion channel modulating compounds may also include anti-contamination agents for the prevention of microorganism contamination. Anti-contamination agents may include but are not limited to antibacterial and antifungal agents, for example, paraben, chlorobutanol, phenol sorbic acid, and the like.

Formulations of the ion channel modulating compound may also be sterilized by, for example, by filtration through a bacteria-retaining filter, or by incorporating sterilizing agents in the form of sterile solid formulations which can be dissolved in sterile water, or some other sterile medium immediately before use or formulation.

Formulations of the ion channel modulating compounds may also include isotonic agents such as sugars, sodium chloride, and the like.

In some cases it is desirable to prolong the effect of the ion channel modulating compound. This may be accomplished in formulations of the ion channel modulating compound that slow the absorption of the ion channel modulating compound from subcutaneous or intramuscular injection. This may be accomplished by the use of a liquid suspension of crystalline or amorphous material having poor water solubility. The rate of absorption of the ion channel modulating compound then depends upon its rate of dissolution which, in turn, may depend upon crystal size and crystalline form. Alternatively, delayed absorption of a parenterally administered drug form can be accomplished by dissolving or suspending the drug in an oil vehicle. Prolonged absorption formulations for injection can include agents which delay absorption including but not limited to aluminum monostearate and gelatin.

Ion channel modulating compounds can be given per se or as formulations containing, for example, 0.1 to 99.5% (more preferably, 0.5 to 90%) of ion channel modulating compound.

Immediate Release and Controlled Release Formulations

The ion channel modulating compounds described herein may be formulated as immediate release (IR) or controlled release (CR) tablets.

In one version, the ion channel modulating compound formulation contains (1R,2R)-2-[(3R)-Hydroxypyrrolidinyl]-1-(3,4-dimethoxyphenethoxy)cyclohexane monohydrochloride ($C_{20}H_{31}NO_4 \cdot HCl$). This compound is orally bioavailable in humans and animals (dog, rat and monkey). The drug is rapidly absorbed, and has a linear PK in humans following a 10-minute infusion. The half-life of the drug in healthy volunteers has been shown to be approximately 2 hours compared to 3-4 hours in patients with recent onset AF.

The drug is highly soluble in citrate solution (143 mg/mL), and has a pH of 3.2 in water, and a pKa of 8.32. It is anhydrous, and is stable under long term and accelerated conditions (ICH). Both IR and CR forms of the drug may be formulated so that a final dosage form exhibits many desirable properties including, but not limited to: good tabletting characteristics (e.g., good flow, compression, appearance, weight variation, hardness, friability, content uniformity and dissolution rate properties), good bioavailability profiles (e.g., 12-hour in-vivo drug release profile for the CR tablet), excellent stress and long-term stability, satisfies USP and EU standards, small tablet size, simple but efficient and cost-effective processing, and CR and IR tablets may have approximately the same weight and appearance.

a. Continuous Release tablets of (1R,2R)-2-[(3R)-Hydroxy-pyrrolidinyl]-1-(3,4-Dimethoxyphenethoxy)cyclohexane monohydrochloride ($C_{20}H_{31}NO_4 \cdot HCl$)

CR tablets may be made by incorporating the drug within a matrix systems, including but not limited to: a hydrophilic matrix system, a hydrophobic (plastic matrix system), a hydrophilic/hydrophobic matrix system, a fat/wax system, and a film-coated particulate system.

Hydrophilic matrix systems show uniform and constant drug diffusion from a tablet prepared with a hydrophilic, gelling excipient after it is placed in an aqueous environment. Drug release is controlled by a gel diffusional barrier which is formed. The process is usually a combination of gel hydration, drug diffusion, and gel erosion.

Hydrophobic (plastic) matrix systems utilize inert, insoluble polymers and copolymers to form a porous skeletal structure in which the drug is embedded. Controlled drug release is effected by diffusion of drug through the capillary wetting channels and pores of the matrix, and by erosion of the matrix itself.

Hydrophilic/hydrophobic matrix systems utilize a combination of hydrophilic and hydrophobic polymers that forms a soluble/insoluble matrix in which the drug is embedded. Drug release is by pore and gel diffusion as well as tablet matrix erosion. The hydrophilic polymer is expected to delay the rate of gel diffusion.

In Fat-wax matrix systems, the drug is incorporated in a hot melt of a fat-wax matrix, solidified sized and compressed with appropriate tablet ingredients. Controlled release of the drug is effected by pore diffusion and erosion of the fat-wax matrix. The addition of a surfactant as a wicking agent helps water penetration of the matrix to cause erosion. Film-coated particulate systems include time-release granulations, prepared by extrusion-spheronization process or by conventional granulation process that have been film-coated to produce differing species of controlled release particles with specific drug release characteristics.

Controlled release particles may be compressed together with appropriate tabletting excipients to produce tablets with the desired controlled release profile. Drug release is by particle erosion in either acid (gastric) or alkaline (intestinal) pH.

Excipients that may be used for the above CR matrix systems are listed in tables 1 to 5 below. Outlined are the chemical and brand names, compendial status, function, and range of use levels.

TABLE 1

Excipients for Hydrophilic Matrix System

| Item # | Excipient | Compendial Status | Function | % Low | % High |
|---|---|---|---|---|---|
| 1. | Methocel K4M (CR Grade) | USP | Hydrophilic polymer | 10.0 | 40.0 |
| 2. | Hydroxypropyl Cellulose | USP/EP/JP | Hydrophilic polymer | 10.0 | 40.0 |

TABLE 1-continued

Excipients for Hydrophilic Matrix System

| Item # | Excipient | Compendial Status | Function | % Low | % High |
|---|---|---|---|---|---|
| 3. | Methocel E4M Premium (CR Grade) | USA | Hydrophobic polymer | 10.0 | 40.0 |
| 4. | Sodium carboxy-methyl cellulose | USP | Hydrophobic polymer | 10.0 | 40.0 |
| 5. | Hydroxyethyl Cellulose | USP/EP/JP | Hydrophilic polymer | 10.0 | 40.0 |
| 6. | Polyvinyl pyrrolidone | USP | Hydrophilic Polymer/Binder | 5.0 | 10.0 |
| 7. | Lactose (Fast Flo) | USP/EP/JP | Filler/Diluent | 20.0 | 60.0 |
| 8. | Microcrystalline Cellulose (Avicel) | USP/EP/JP | Filler/Diluent | 16.7 | 30.0 |
| 9. | Calcium Phosphate Dibasic (Emcompress) | USP-NF | Filler/Diluent | 16.7 | 33.3 |
| 10. | Colloidal Silicon Dioxide | USP/EP/JP | Glidant | 0.5 | 2.0 |
| 11. | Magnesium Stearate (Non-Bovine) | USP/EP/JP | Lubricant | 0.5 | 1.0 |
| 12. | Stearic Acid | USP/EP | Lubricant | 0.5 | 2.0 |

TABLE 2

Excipients for Hydrophobic Matrix System

| Item # | Excipient | Compendial Status | Function | % Low | % High |
|---|---|---|---|---|---|
| 1. | Ethyl Cellulose (Ethocel) | USP-NF | Hydrophobic polymer | 20.0 | 40.00 |
| 2. | Eudragit RSPO | USP-NF | Hydrophobic polymer | 20.0 | 40.00 |
| 3. | Eudragit S-100 | USP-NF | Hydrophobic polymer | 20.0 | 40.00 |
| 4. | Kollidon SR | USP-NF | Hydrophobic polymer | 20.0 | 40.00 |
| 5. | Lactose (Fast Flo) | USP/EP/JP | Filler/Diluent | 20.0 | 60.0 |
| 6. | Microcrystalline Cellulose (Avicel) | USN/EP/JP | Filler/Diluent | 16.7 | 30.0 |
| 7. | Calcium Phosphate Dibasic (Emcompress) | USP-NF | Filler/Diluent | 16.7 | 33.3 |
| 8. | Colloidal Silicon Dioxide | USP/EP/JP | Glidant | 0.5 | 2.0 |
| 9. | Magnesium Stearate (Non-Bovine) | USP/EP/JP | Lubricant | 0.5 | 1.0 |
| 10. | Stearic Acid | USP/EP | Lubricant | 0.5 | 2.0 |

TABLE 3

Excipients for Fax-Wax Matrix System

| Item # | Excipient | Compendial Status | Function | % Low | % High |
|---|---|---|---|---|---|
| 1. | Cetyl Alcohol | USP | Erodable Retardant | 15.0 | 25.0 |
| 2. | Cetearyl Alcohol | USN | Erodable Retardant | 15.0 | 25.0 |
| 3. | Lactose (Fast Flo) | USP/EP/JP | Filler/Diluent | 20.0 | 60.0 |
| 4. | Microcrystalline Cellulose (Avicel) | USP/EP/JP | Filler/Diluent | 16.7 | 30.0 |
| 5. | Calcium Phosphate Dibasic (Emcompress) | USP-NF | Filler/Diluent | 16.7 | 33.3 |
| 6. | Colloidal Silicon Dioxide | USP/EP/JP | Glidant | 0.5 | 2.0 |
| 7. | Magnesium Stearate (Non-Bovine) | USP/EP/JP | Lubricant | 0.5 | 1.0 |
| 8. | Stearic Acid | USP/EP | Lubricant | 0.5 | 2.0 |

TABLE 4

Excipients for Hydrophilic/Hydrophobic Matrix System

| Item # | Excipient | Compendial Status | Function | % Low | % High |
|---|---|---|---|---|---|
| 1. | Ethyl Cellulose (Ethocel) | USP-NF | Hydrophobic polymer | 20.0 | 40.00 |
| 2. | Eudragit RSPO | USP-NF | Hydrophobic polymer | 20.0 | 40.00 |
| 3. | Eudragit S-100 | USP-NF | Hydrophobic polymer | 20.0 | 40.00 |
| 4. | Kollidon SR | USP-NF | Hydrophobic polymer | 20.0 | 40.00 |
| 5. | Methocel E4M Premium (CR Grade) | USP | Hydrophobic polymer | 10.0 | 40.0 |
| 6. | Methocel K4M (CR Grade) | USP | Hydrophilic polymer | 10.0 | 40.0 |
| 7. | Polyvinyl pyrrolidone | USP | Hydrophilic Polymer/Binder | 5.0 | 10.0 |
| 8. | Lactose (Fast Flo) | USP/EP/JP | Filler/Diluent | 20.0 | 60.0 |
| 9. | Microcrystalline Cellulose (Avicel) | USP/EP/JP | Filler/Diluent | 16.7 | 30.0 |
| 10. | Calcium Phosphate Dibasic (Emcompress) | USP-NF | Filler/Diluent | 16.7 | 33.3 |
| 11. | Colloidal Silicon Dioxide | USP/EP/JP | Glidant | 0.5 | 2.0 |
| 12. | Magnesium Stearate (Non-Bovine) | USP/EP/JP | Lubricant | 0.5 | 1.0 |
| 13. | Stearic Acid | USP/EP | Lubricant | 0.5 | 2.0 |

TABLE 5

Excipients for Film-Coated Particulate System

| Item # | Excipient | Compendial Status | Function | % Low | % High |
|---|---|---|---|---|---|
| 1. | Lactose (Fast Flo) | USP/EP/JP | Filler/Diluent | 20.0 | 60.0 |
| 2. | Microcrystalline Cellulose (Avicel) | USP/EP/JP | Filler/Diluent | 16.7 | 30.0 |
| 3. | Calcium Phosphate Dibasic (Emcompress) | USP-NF | Filler/Diluent | 16.7 | 33.3 |
| 4. | Starch 1500 (Pre-gelatinized Starch) | USP-NF | Glidant/Disintegrant | 5.0 | 10.0 |
| 5. | Polyvinyl pyrrolidone K-29-32 | USP | Binder | 5.0 | 10.0 |
| 6. | Sodium Starch Glycolate (Explotab) | USP-NF | Disintegrant | 1.17 | 3.3 |
| 7. | SodiumCross-carmellose (Ac-Di-Sol) | USP-NF | Disintegrant | 1.7 | 5.0 |
| 8. | Colloidal Silicon Dioxide | USP/EP/JP | Glidant | 0.5 | 2.0 |
| 9. | Magnesium Stearate (Non-Bovine) | USP/EP/JP | Lubricant | 0.5 | 1.0 |
| 10. | Stearic Acid | USP/EP | Lubricant | 0.5 | 2.0 |
| 11. | Plasticized ethylcellulose dispersion | Vendor's specification | Coating system | TBD | TBD |
| 12. | Plasticized methacrylate dispersion | Vendor's specification | Coating system | TBD | TBD |
| 13. | Plasticized polyvinyl acetate phthalate dispersion | Vendor's specification | Coating system | TBD | TBD |

CR formulations of the drug may be processed by methods including but not limited to: direct compression (dry blend of drug with flowable excipients followed by compression), wet granulation (application of a binder solution to powder blend, followed by drying, sizing, blending and compression), dry granulation or compaction (densifying the drug or drug/powder blend through slugging or with a compactor to obtain flowable, compressible granules), fat-wax mot melt granulation (embedding of drug in molten fatty alcohols, followed by cooling, sizing, blending and compression), and film-coating of particulates (dry blend, wet granulation, kneading, extrusion, spheronization, drying, film-coating, followed by blending of differing; species of film-coated spheres, and compression).

In one version, a 100 mg CR formulation containing fillers, a glidant, lubricants and a hydrophilic polymer is made by direct compression. In this formulation, the drug is mixed with Starch 1500 in a small polyethylene (PE) bag then passed through a #30 mesh screen. The screened mix is then transferred to its original PE bag along with Prosolv SMCC90, Lactose Fast Flo and Methoeel K4M and mixed for 2 minutes. A portion (e.g. 1 g) of this blend is then mixed with Magnesium Stearate and Stearic Acid in a PE bag, transferred back to the bulk blend via a #30 mesh screen and blended for 1 minute. Tablets may be compressed with a suitable punch (e.g., a 9 mm punch) on a single punch press to obtain a tablet hardness of 7-12 KN. This formulation is described in the table below.

TABLE 6

100 mg CR Tablet Formulation

| | Ingredient | mg/tab | % w/w | Wt. (g) |
|---|---|---|---|---|
| 1. | Ion channel modulating compound | 100.00 | 33.33 | 5.00 |
| 2. | Starch 1500 | 15.00 | 5.00 | 0.75 |
| 3. | Prosolv SMCC90 | 45.70 | 15.23 | 2.29 |
| 4. | Lactose Fast Flo | 91.30 | 30.43 | 4.57 |
| 5. | Methocel K4M | 45.00 | 15.00 | 2.25 |
| 6. | Stearic Acid | 1.50 | 0.50 | 0.08 |
| 7. | Magnesium stearate | 1.50 | 0.50 | 0.08 |
| | Total Weight | 300.00 | 100.00 | 155.00 |

Compositions of alternative formulations of CR tablets such as the hydrophobic and hot melt (solid dispersion) formulations are shown in the table below. The hydrophilic composition is also shown for comparison.

TABLE 7

Proposed Initial Compositions for CR Matrix Tablets

| Item No. | Formula Ingredients | hydrophilic % w/w | hydrophobic % w/w | hot melt % w/w |
|---|---|---|---|---|
| 1. | Ion Channel Modulating Compound | 33.33 | 44.44 | 44.44 |
| 2. | Methocel K4MCR) | 15.00 | — | — |
| 3. | Cetyl Alcohol | — | — | 22.22 |
| 4. | Ethylcellulose | — | 8.80 | — |
| 5. | Kollidon SR | — | 31.11 | — |
| 6. | Starch 1500 | 5.00 | — | — |
| 7. | Prosolv SMCC90 | 15.23 | — | 15.56 |
| 8. | Lactose | 30.43 | 14.22 | 16.44 |
| 9. | Stearic Acid | 0.50 | 0.67 | 0.67 |
| 10. | Magnesium Stearate (Non-Bov) | 0.50 | 0.67 | 0.67 |
| | Total | 100.00 | 100.00 | 100.00 |

* Tablet weight: 300 mg
** Tablet weight: 225 mg b. IR tablets of (1R,2R)-2-[(3R)-Hydroxypyrrolidinyl]-1-(3,4-Dimethoxyphenethoxy)cyclohexane monohydrochloride ($C_{20}H_{31}NO_4 \cdot HCl$)

IR tablets of the drug may be formulated by compounding the drug with appropriate, fillers, binders, glidants, disintegrants and lubricants that give a satisfactory tabletting characteristics and subsequent rapid disintegration and dissolution of the tablets. Excipients useful for IR tabletting are listed in the following table. Outlined are the chemical and brand names, compendial status, function, and range of use levels:

TABLE 8

Excipients for IR Prototype Formulations

| Item # | Excipient | Compendial Status | Function | % Low | % High |
|---|---|---|---|---|---|
| 1. | Sodium Starch Glycolate | USP | Disintegrant | 1.0 | 3.0 |
| 2. | Pre-gelatinized Starch | USP | Glidant/Disintegrant | 5.0 | 10.0 |
| 3. | Silicified Microcrystalline Cellulose | USP | Filler/Diluent | 20.0 | 40.0 |
| 4. | Polyvinyl pyrrolidone | USP | Binder | 5.0 | 10.0 |
| 5. | Lactose (Fast Flo) | USP/EP/JP | Filler/Diluent | 20.0 | 60.0 |
| 6. | Microcrystalline Cellulose (Avicel) | USP/EP/JP | Filler/Diluent | 16.7 | 30.0 |
| 7. | Calcium Phosphate Dibasic (Emcompress) | USP-NF | Filler/Diluent | 16.7 | 33.3 |
| 8. | Colloidal Silicon Dioxide | USP/EP/JP | Glidant | 0.5 | 2.0 |
| 9. | Magnesium stearate (Non-Bovine) | USP/EP/JP | Lubricant | 0.5 | 1.0 |
| 10. | Stearic Acid | USP/EP | Lubricant | 0.5 | 2.0 |

IR tablets of the drug may be made by: direct compression (dry blend of drug with flowable excipients followed by compression), wet granulation (application of a binder solution to powder blend, followed by drying, sizing, blending and compression), dry granulation or compaction (densifying API of API/powder blend through slugging or with a compactor to obtain flowable, compressible granules), or a combination of these steps. Granules of the drug are sized, blended with the appropriate excipients and compressed in tablets.

In one version, a 100 mg IR formulation containing basic IR excipients, i.e., fillers, a glidant, a disintegrant and lubricants may be made by direct compression. This formulation is blended in small PE bags and subsequently compressed manually on a single punch bench tablet press with an appropriate tablet punch. The ion channel modulating drug is mixed with Starch 1500 in a small polyethylene (PE) bag then passed through a #30 mesh screen. The screened mix is then transferred to its original PE bag along with Prosolv SMCC90, Lactose Fast Flo and Explotab and mixed for 2 minutes. A portion (e.g. 1 g) of this blend is then mixed with Magnesium Stearate and Stearic Acid in a PE bag, transferred back to the bulk blend via a #30 mesh screen and blended for 1 minute. Tablets are compressed with a suitable punch (e.g., a 9 mart punch) on a single punch press to obtain a tablet hardness of 7-12 KN. The formulation is described in the table below.

TABLE 9

100 mg IR Tablet Formulation

| | Ingredient | mg/tab - | % w/w | Wt. (g) |
|---|---|---|---|---|
| 1. | Drug (C20H31NO4•HCl) | 100.00 | 33.33 | 5.00 |
| 2. | Starch 1500 | 15.00 | 5.00 | 0.75 |
| 3. | Prosolv SMCC90 | 60.00 | 20.00 | 3.00 |
| 4. | Lactose Fast Flo | 117.00 | 39.17 | 5.88 |
| 5. | Sodium Starch Glycolate (Explotab) | 3.00 | 1.00 | 0.15 |
| 6. | Stearic Acid | 3.00 | 1.00 | 0.15 |
| 7. | Magnesium Stearate | 1.50 | 0.50 | 0.08 |
| | Total Weight | 300.00 | 100.00 | 15.00 | c. In-Vitro Dissolution of IR and CR Tablets

The release profile of active agent (such as the ion channel modulating compound) and any additives may be empirically determined in vitro by examining the dissolution of the tablet over time. A USP approved method for dissolution or release test can be used to measure the rate of release in vitro (USP 24; NF 19 (2000) pp. 1941-1951). For example, a weighed tablet of the drug (e.g. (1R,2R)-2-[(3R)-Hydroxypyrrolidinyl]-1-(3,4-dimethoxyphenethoxy)cyclohexane monohydrochloride) is added to a measured volume of a solution containing 0.9% NaCl in water, where the solution volume will be such that the active agent concentration after release is less than 20% of saturation. The mixture is maintained at 37° C. and stirred or shaken slowly to maintain the tablet in suspension. The release of the dissolved drug as a function of time may then be followed by various methods known in the art, such as spectrophotometrically, HPLC, mass spectroscopy, and the like, until the solution concentration becomes constant or until greater than 90% of the active agent has been released.

Figure 2:
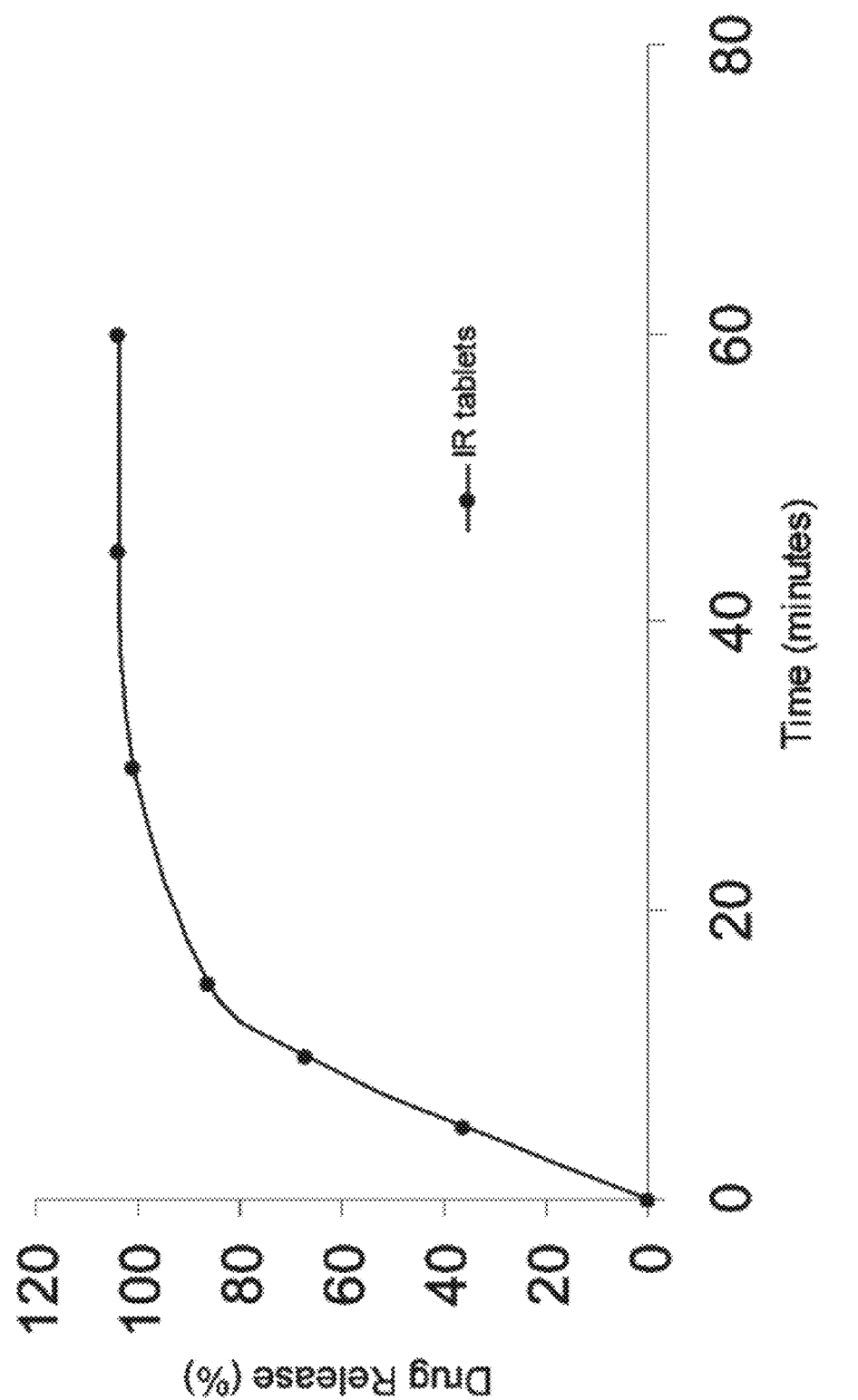
FIG. 2 shows the cumulative percentage of dissolution of an intermediate release form of the ion channel modulating compound (1R,2R)-2-[(3R)-hydroxypyrrolidinyl]-1-(3,4-dimethoxyphenethoxy)cyclohexane monohydrochloride over time.
Figure 3:
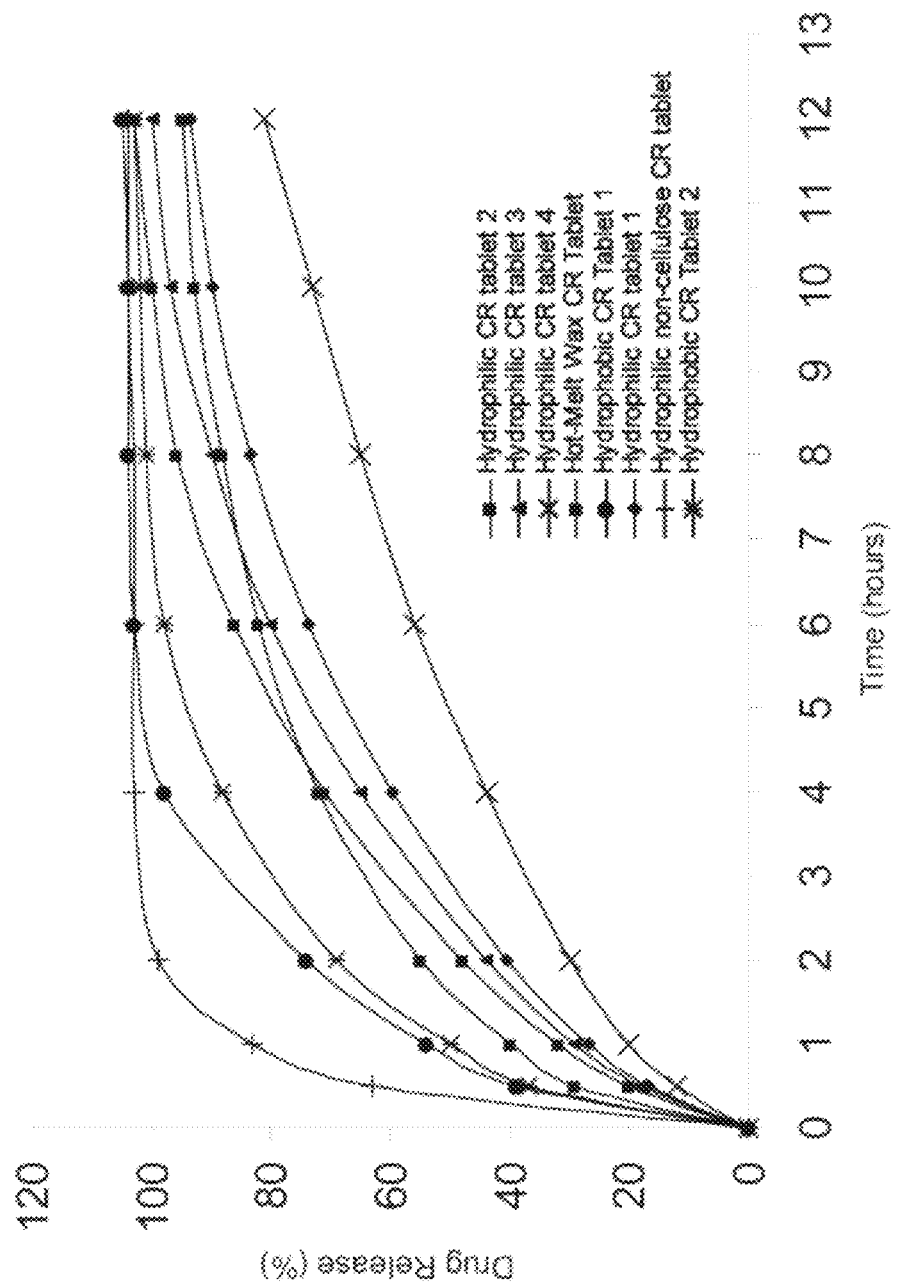
FIG. 3 shows a comparison of the cumulative percentage of dissolution of different controlled release formulations of the ion channel modulating compound (1R,2R)-2-[(3R)-hydroxypyrrolidinyl]-1-(3,4-dimethoxyphenethoxy)cyclohexane monohydrochloride over time.

In one variation, various IR and CR tabletted formulations of (1R,2R)-2-[(3R)-Hydroxypyrrolidinyl]-1-(3,4-dimethoxyphenethoxy)cyclohexane monohydrochloride (described below) may have in vivo cumulative percentage release profiles the same as or substantially the same as shown in FIGS. 2 and 3. FIG. 2 shows that release profile (percent cumulative release over time) for the IR formulation of the ion channel modulating compound. This IR formulation is described in Table 10, Part I below. More than 80% of the drug in the IR form has dissolved by fifteen minutes.

Release profiles for different CR formulations show that the CR formulations dissolve in hours rather than minutes (FIG. 3). FIG. 3 shows a comparison of four different hydrophilic CR tablets, a hydrophilic non-cellulose tablet, a hot-melt wax tablet, and two hydrophobic tablets. The formulations of these CR forms are given in Table 10, Part I and Table 10, Part II.

TABLE 10 Part I

IR and Hydrophilic CR tablet formulations

| | Tablet Type: | | | | |
|---|---|---|---|---|---|
| | IR tablet formulation | Hydrophilic CR tablet 1 | Hydrophilic CR tablet 2 | Hydrophilic CR tablet 3 | Hydrophilic CR tablet 4 |
| Ingredient/tablet strength: mg/tablet-% | 100 mg | 100 mg | 100 mg | 100 mg | 300 mg |
| Ion Channel Modulating Drug (C20H31NO4•HCl) | 100.00 | 100.00 | 100.00 | 100.00 | 100.00 |
| Starch pregelatinized 1500 | 15.00 | 15.00 | 10.00 | 10.00 | 10.00 |
| Silicified Microcrystalline Cellulose -Prosolv SMCC90 | 60.00 | 45.70 | 32.00 | 32.00 | 32.00 |
| Lactose Fast Flo | 117.50 | 91.30 | 40.00 | 40.00 | 40.00 |
| Sodium Starch Glycolate -Explotab | 3.00 | | — | — | — |
| Hydroxypropyl Methylcellulose- Methocel K4M | | 45.00 | 40.00 | 40.00 | 40.00 |
| Cetostearyl Alcohol - Kalcol6850 | | | | | |
| Polyethylene Glycol 8000 | | | | | |
| Kollidon SR | | | | | |
| Ethyl Cellulose Standard 4 | | | | | |
| Eudragit RSPO | | | | | |
| Anhydrous Emcompress | | | | | |
| Stearic Acid | 3.00 | 1.50 | 1.50 | 1.50 | 1.50 |
| Magnesium Stearate-Non-Bovine | 1.50 | 1.50 | 1.50 | 1.50 | 1.50 |
| Total Weight: (mg) | 300.00 | 300.00 | 225.00 | 225.00 | 675.00 |

TABLE 10 Part II

| | CR Formulations | | | | |
|---|---|---|---|---|---|
| | Tablet Type: | | | | |
| | Hydrophilic CR non-cellulose tablet | Wax Matrix CR Tablet | Hot-Melt Wax CR Tablet | Hydrophobic CR Tablet 1 | Hydrophobic CR Tablet 2 |
| Ingredient/tablet strength: mg/tablet-% | 100 mg | 100 mg | 100 mg | 100 mg | 100 mg |
| Ion Channel Modulating Drug (C20H31NO4•HCl) | 100.00 | 100.00 | 100.00 | 100.00 | 100.00 |
| Starch pregelatinized 1500 | | | | | |
| Silicified Microcrystalline Cellulose -Prosolv SMCC90 | 33.75 | 50.00 | 35.00 | | |
| Lactose Fast Flo | | 37.00 | 37.00 | 32.00 | |
| Sodium Starch Glycolate -Explotab | | | | | |
| Hydroxypropyl Methylcellulose- Methocel K4M | | | | | |
| Cetostearyl Alcohol - Kalcol6850 | | 35.00 | 50.00 | | |
| Polyethylene Glycol 8000 | 45.00 | | | | |
| Kollidon SR | | | | 70.00 | 45.00 |
| Ethyl Cellulose Standard 4 | | | | 20.00 | |
| Eudragit RSPO | 15.75 | | | | 45.00 |
| Anhydrous Emcompress | 27.50 | | | | 32.00 |
| Stearic Acid | 1.50 | 1.50 | 1.50 | 1.50 | 1.50 |
| Magnesium Stearate-Non-Bovine | 1.50 | 1.50 | 1.50 | 1.50 | 1.50 |
| Total Weight: (mg) | 225.00 | 225.00 | 225.00 | 225.00 | 225.00 |

Combinations of Ion Channel Modulating Compounds and Biomedical Devices

The ion channel modulating compounds herein may also be used in conjunction or combination with biomedical devices, including but not limited to applying the ion channel modulating compound as a component of a biomedical device, such as coating the ion channel modulating compound on a device to achieve an extended, immediate, or controlled release; administering the ion channel modulating compound in coordination with a treatment such as administering pre- or post-operatively to a subject; or releasing the ion channel modulating compound from a biomedical device as needed, such as release from a "smart" pacemaker or cardiac sensor.

Rechargeable or biodegradable devices could deliver controlled release of the ion channel modulating compounds to a subject. Such devices include but are not limited to slow release polymeric devices for the controlled delivery of drugs, for example proteinaceous biopharmaceuticals; and osmotic pumps and osmotic tables. A variety of biocompatible polymers (including hydrogels), including both biodegradable and non-degradable polymers, could form an implant for the sustained release of the ion channel modulating compound at a particular site, including a target site. An implantable or external pump system could also be used to deliver ion channel modulating compounds. Ion channel modulating compounds could also be delivered via incorporation as a coating onto a biomedical device, such as an implantable device (e.g. a heart valve).

Implantable systems incorporating the ion channel modulating system could be implanted in a subject anywhere that would allow beneficial therapeutic effect, including but not limited to implantation in heart tissue or pericardial sacs.

Biomedical devices appropriate for use in conjunction with the ion channel modulating compounds described here could be used to treat or prevent cardiovascular disorders. For example, formulations of the ion channel modulating compounds could be used in combination or conjunction with angioplastic balloons, cardiac monitors, stents (including drug eluting stents), defibrillators, catheters and heart valves, vascular grafts, pacemaker leads, guide wires, and the like which are placed into the blood vessels or the heart or nearby tissue for purposes of monitoring or repair.

On-demand release forms incorporating an ion channel modulating compound can be used for controlled release. Hybrid devices delivering an ion channel modulating compound could incorporate release based on sensing concentration of drug, a biological marker (e.g. enzyme level), or physiological need. In one embodiment, sensing devices could be pacemakers and/or implantable defibrillators modified to release drug upon demand. Drug release could also be regulated and/or monitored by computer control.

EXAMPLES

The following examples demonstrate the methods described in this application. These examples are not intended to limit the scope of the described methods and formulations and are included for illustrative purposes.

Example 1

Termination of Atrial Fibrillation—Step Dosing Iv Study in Human Subjects

A prospective double-blind, placebo-controlled, randomized, dose-response trial was conducted. The compound used in these studies is (1R,2R)-2-[(3R)-hydroxypyrrolidinyl]-1-(3,4-dimethoxyphenethoxy)cyclohexane monohydrochloride, which has structural formula

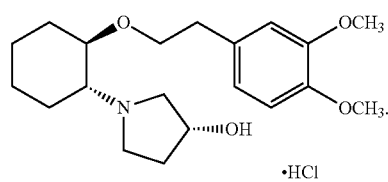

To be eligible, patients had to have a rhythm of sustained atrial fibrillation with a duration of 3-72 hours at the time of randomization. Patients were managed in accordance with ACC/AHA/ESC anticoagulation practice guidelines. Patients>21 years of age were eligible. All patients had to be hemodynamically stable (systolic blood pressure of 90-160 mm Hg with diastolic blood pressure<95 mm Hg).

Patients were excluded for the following reasons: female patients of child-bearing potential; weight>300 lb; history of long QT syndrome, torsade de pointes or an uncorrected QT interval of >450 ms; QRS>120 ms; myocardial infarction, symptoms of angina, congestive heart failure, or stroke within the previous 3 months; cardiac surgery in the previous 6 months; bradycardia (<50 bpm) or sick sinus syndrome unless controlled by a pacemaker; digoxin toxicity; or other reversible cause of atrial fibrillation (such as hyperthyroidism, pulmonary embolism, alcohol intoxication, acute pericarditis); Wolff-Parkinson-White syndrome; COPD requiring daily-bronchodilation therapy; cyanotic or other significant congenital heart disease; concurrent treatment with known QT prolonging drugs or class I or III anti-arrhythmic agents (unless the medication was discontinued more than five half-lives before enrollment); oral amiodarone in the prior 6 months or intravenous amiodarone in the prior month; or end stage diseases. No alcohol, caffeine, herbal remedies or smoking were permitted during the study. Pre-enrollment treatment with β-adrenergic blocking agents, calcium antagonists, and digoxin for control of ventricular rate were permitted.

Eligible patients were approached and provided informed written consent. To enter the trial, all patients had to demonstrate normal serum electrolytes (serum potassium not <3.5 mEq/L, magnesium not <1.5 mEq/L), serum creatinine of 1.8 mg/dL or greater, hemoglobin not <9 g/dL in women or <11 g/dL in men, and liver enzymes less than 1.5× maximal normal values.

Patients were randomized to one of three groups and in each group received up to two 10-minute intravenous infusions, separated by 30 minutes. Infusions were placebo followed by placebo, 0.5 mg/kg followed by 1.0 mg/kg of (1R, 2R)-2-[(3R)-hydroxypyrrolidinyl]-1-(3,4-dimethoxyphenethoxy)cyclohexane monohydrochloride, or 2.0 mg followed by 3.0 mg (1R,2R)-2-[(3R)-hydroxypyrrolidinyl]-1-(3,4-dimethoxyphenethoxy)cyclohexane monohydrochloride (follow-on dose, efficacy dependent). Doses for patients weighing >113 kg were capped as if the patient weight was 113 kg. If the arrhythmia did not terminate or persisted 30 minutes after the end of the first infusion, the second infusion was administered. Outcomes: Efficacy outcomes were adjudicated by the steering committee (DR, BHR, AME) prior to unblinding of treatment allocation; disagreements were resolved following second review and consensus. The primary efficacy end point of this study was the termination of atrial fibrillation. Success was defined as termination for any length of time during infusion or 30 minutes after initiation of infusion. Secondary endpoints included: number of patients in normal sinus rhythm (NSR) at 0.5, 1 and 24 hours after last infusion, as well as the time to conversion.

A Holter rhythm strip continuously monitored ECG, vital signs (blood pressure and heart rate) and $O_2$ saturation were recorded every 2 minutes from the start of infusion to 5 minutes after, as well as at 15, 30, 60, 120, 240, 360, and 480 minutes and at discharge and 1-week follow-up. 12-lead ECGs were obtained before dosing and every minute during infusion to 5 minutes after, as well as at 15, 30, 60, 120, 240, 360, and 480 minutes and at discharge, 24 hours and 1-week follow-up, and at the time of arrhythmia termination or significant rhythm changes. ECGs were interpreted by individual investigators and independently verified by a core lab cardiologist blinded to study treatment. Venous blood samples were drawn for (1R,2R)-2-[(3R)-hydroxypyrrolidinyl]-1-(3,4-dimethoxyphenethoxy)cyclohexane monohydrochloride plasma concentrations at 0, 15, 30, 120, 240, 480 minutes, discharge and at atrial fibrillation termination or significant adverse events. The infusion was discontinued if the arrhythmia terminated after 1 minute of verification, systolic blood pressure decreased to <85 mm Hg or increased >190 mm Hg, HR<50 bpm, intolerable side effects or any change in rhythm or atrioventricular conduction occurred that in the investigator's opinion was a threat to patient safety, a new bundle-branch block developed, QRS increased >50%, uncorrected QT increased to 550 ms or >25% of baseline or any polymorphic VT was noted. If atrial fibrillation persisted past 1 hour after the last infusion, pacing or electrical cardioversion was permitted. The use of other antiarrhythmic agents was discouraged until 12 hours after the (1R,2R)-2-[(3R)-hydroxypynolidinyl]-1-(3,4-dimethoxyphenethoxy)cyclohexane monohydrochloride infusion, unless the investigator considered it necessary to restore sinus rhythm earlier.

The sample size was based on estimates of a placebo conversion rate of 35%, (1R, 2R)-2-[(3R)-hydroxypyrrolidinyl]-1-(3,4-dimethoxyphenethoxy)cyclohexane monohydrochloride conversion rate of 60%, an alpha of 0.05 and a beta of 0.9. A priori, up to 20 patients were to be recruited in each group to detect this difference, with an anticipated need of at least 18 evaluable patients per group.

All patients who received study medication were included in the safety analysis, and 55 patients were evaluated for efficacy. Data are presented as mean±SD, median with interquartile range (IQR), all tests were performed as two sided and 95% CI were produced; p<0.05 was considered statistically significant unless stated otherwise. Analysis of the relationship between termination of atrial fibrillation and treatment was performed using a chi-square analysis. In cases of small cell frequencies, the Fisher's exact test was used. A Cochran-Armitage test statistic with table scores was used to test the ascending dose evaluation of efficacy.

Patients who were electrically cardioverted were not evaluated for secondary endpoints. The time to conversion from the start of the first infusion was analyzed by the Cox regression method of event time analysis and one-way ANOVA. Assessment of the significance of time point values and mean change from baseline to each follow-up reading of ECG intervals (QRS, QT, QTc), blood pressures, and heart rates were made within dose groups using paired t tests, and comparisons among dose groups were made using a one-way ANOVA.

Fifty-six patients with recent onset (new or recurrent) atrial fibrillation were administered blinded treatment of the 9 patients randomized but not treated, 6 spontaneously converted to NSR and did not receive drug, 1 patient converted to atrial flutter, 1 patient withdrew consent and 1 was a screening error. The treatment allocation was as follows: placebo/placebo, 20; 0.5 mg/kg+1.0 mg/kg (1R,2R)-2-[(3R)-hydroxypyrrolidinyl]-1-(3,4-dimethoxyphenethoxy)cyclohexane monohydrochloride, 18; and 2.0 mg/kg+3.0 mg (1R, 2R)-2-[(3R)-hydroxypyrrolidinyl]-1-(3,4-dimethoxyphenethoxy)cyclohexane monohydrochloride, 18.

The mean age of the patients was 61 years (range 24-88 years), 61% were male. The average duration of the arrhythmia was 17.8±13 hours in the placebo group, 23.6±22 hours and 24.7±20 hours in the RSD-1 and RSD-2 dosing groups, respectively. Overall, 62% of patients had at least one previous episode of atrial fibrillation. Baseline clinical characteristics were similar across groups except that patients in the placebo group tended to more frequently report atrial fibrillation in the past than in the (1R,2R)-2-[(3R)-hydroxypyrrolidinyl]-1-(3,4-dimethoxyphenethoxy)cyclohexane monohydrochloride dosed groups.

Adverse Events: A total of 39 patients experienced 122 adverse events (AEs) over the course of the study, with a similar incidence of AEs among the three treatment groups. The majority of AEs were of grade 1 (mild) or grade 2 (moderate) intensity. There were 4 AEs that occurred in 2 patients considered either definitely or probably related to study drug. Both patients were in the RSD-2 dose group: one patient reported paraesthesia, and one patient reported paraesthesia, nausea, and hypotension all of mild intensity.

The most common AEs experienced in this study were cardiac disorders, reported by 7 patients (35.0%) in the Placebo group, 4 patients (22.2%) in the RSD-1 group, and 3 patients (16.7%) in the RSD-2 group. In addition to the serious adverse events discussed below, the cardiac disorders in the placebo group included two patients with ventricular tachycardia and a patient with ventricular extrasystoles. Ventricular extrasystoles were also seen in two patients and sinus bradycardia in one patient of the low dose group. Ventricular extrasystoles were seen in two patients and sinus bradycardia in another patient in the RSD-2 group. Other common AEs occurring with a similar frequency among treatment groups were nervous system disorders, general disorders, investigations, and infections and infestations.

Serious AEs: Serious AEs were reported in 5 patients (4 patients of the Placebo group and 1 patient of the RSD-1 group). There were no SAEs that were considered related to study drug, and all SAEs resolved either during the course of the study or during the follow-up period. There were no instances of polymorphic ventricular tachycardia in the study.

A transient cerebral ischemic attack occurred 1 day after conversion in a placebo treated patient with a therapeutic INR at the time of conversion. The remaining serious AEs in the placebo group consisted of severe bradycardia and hypotension immediately following conversion in one patient, pulmonary edema in another patient and recurrent atrial fibrillation in the final patient with a serious AE. One patient in the RSD-1 group experienced VF induced by an asynchronous discharge during an electrical cardioversion attempt performed 1 hour after the second infusion.

Figure 4:
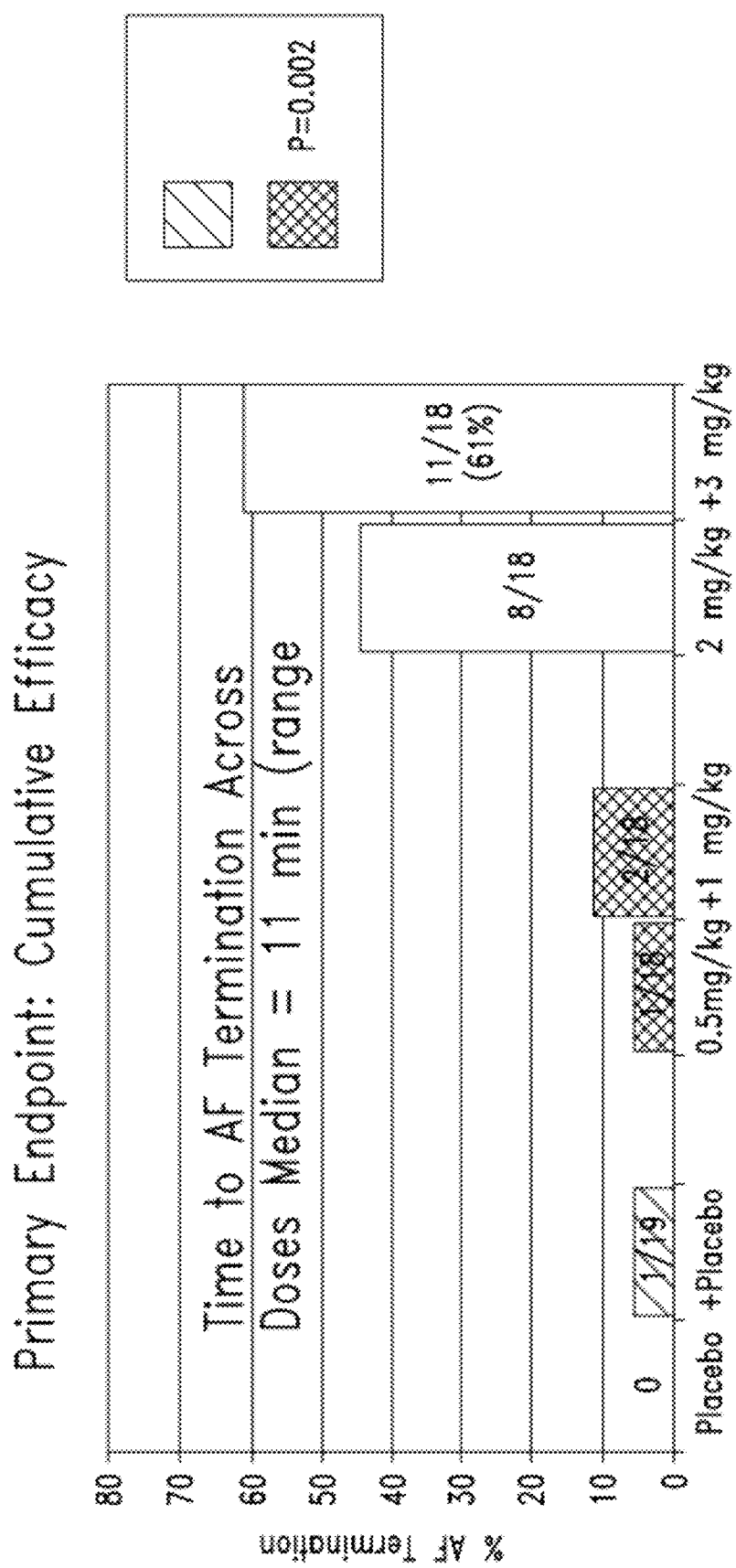
FIG. 4 shows the cumulative percentage of patients terminating atrial fibrillation (AF) after infusions of placebo, 0.5 and 1 mg/kg (1R,2R)-2-[(3R)-hydroxypyrrolidinyl]-1-(3,4-dimethoxyphenethoxy)cyclohexane monohydrochloride or 2.0 and 3.0 mg/kg (1R,2R)-2-[(3R)-hydroxypyrrolidinyl]-1-(3,4-dimethoxyphenethoxy)cyclohexane monohydrochloride, in patients with recent onset atrial fibrillation.

The cumulative atrial fibrillation termination within 30 minutes of infusion was 61.1% (11 of 18 patients) after 2+3 mg/kg (1R,2R)-2-[(3R)-hydroxypyrrolidinyl]-1-(3,4-dimethoxyphenethoxy)cyclohexane monohydrochloride infusion (the "RSO-2" group), 11.1% (2 of 18 patients) after 0.5+1 mg/kg (1R,2R)-2-[(3R)-hydroxypyrrolidinyl]-1-(3,4-dimethoxyphenethoxy)cyclohexane monohydrochloride (the "RSD-1 group") and 5.3% (1 of 19 patients) after placebo+placebo. Paired comparisons indicated a statistically significant difference (p=0.0003; FIG. 4) between placebo (5.3%) and the RSD-2 group (61.1%). There was no significant difference (p=0.51) in the success rates between the RSD-1 group and placebo. Of the 11 successful terminations in the RSD-2 group, 8 terminated on the first infusion (44.4% or 8/11=73%).

The number of patients in NSR at 30 minutes post infusion was 56% (10 of 18 patients, p=0.0008) in the RSD-2 group, compared to 11% (2 of 18 patients) in the RSD-1 group (p=0.51) and 5% (1 of 19 patients) in the placebo group. The number of efficacy evaluable patients in NSR at 1 hour post infusion was 53% (9 of 17 patients, p=0.0014) in the RSD-2 group, and 11% (2 of 18 patients, p=0.51) in the RSD-1 group, compared to 5% (1 of 19 patients) in the placebo group. Patients in NSR (excluding those electrically cardioverted) at 24 hours post infusion was 79% (11 of 14 patients, p=0.14) in the RSD-2 group, and 56% (5 of 9 patients, p=0.80) in the RSD-1 group compared to 50% (5 of 10 patients) in the placebo group.

The median time to conversion to NSR from the start of the first infusion in the 11 responders in the RSD-2 group was 14 minutes (range, 3 to 871 minutes; p=0.016) compared to the 5 spontaneous responders in the placebo group with a median time of 162 minutes (range, 58 to 1119 minutes). The median time to conversion to NSR from the start of the first infusion in the 5 eventual responders in the RSD-1 group was 166 minutes (range, 1 to 332 minutes; p=0.886 vs. placebo).

The median time to termination of atrial fibrillation was 11 minutes after start of the first infusion (range, 3 to 58 minutes) in the RSD-2 group. In fact, all the responders in this group reached primary end-point during drug infusion or within 10 minutes of the last infusion. One of the 11 responders in this group terminated AF, but went into atrial flutter and subsequently converted to NSR 14.5 hours later.

Within the study period (24 hours) electrical cardioversion was attempted in 9 of 19 (47%) placebo treated, 9 of 18 (50%) RSD-1 treated and 4 of 18 (22%) RSD-2 treated patients and was successful in 8 (89%), 9 (100%) and 4 (100%) patients, respectively.

Figure 5:
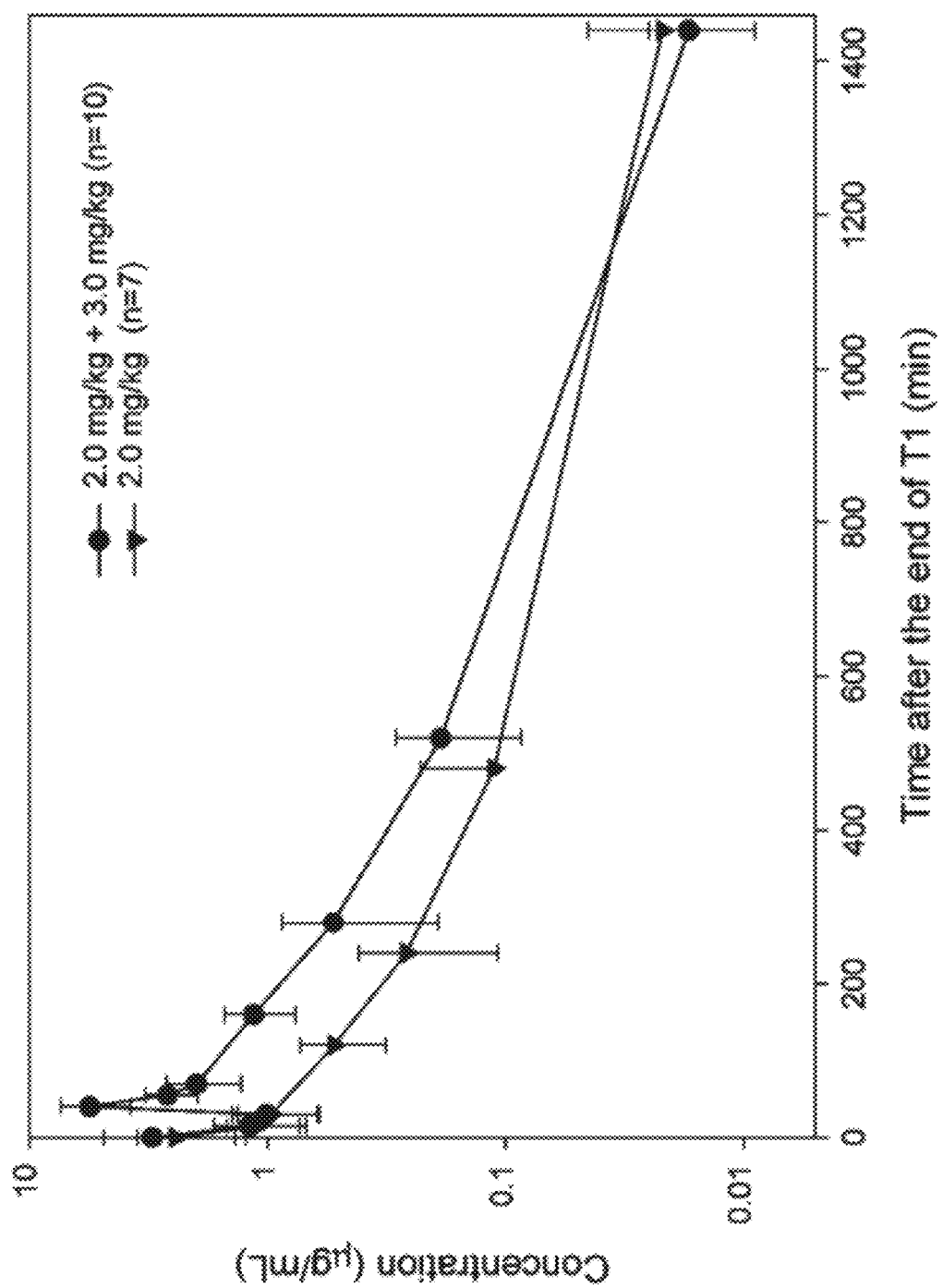
FIG. 5 shows the plasma concentrations of (1R,2R)-2-[(3R)-hydroxypyrrolidinyl]-1-(3,4-dimethoxyphenethoxy) cyclohexane monohydrochloride after infusion in patients dosed at 2 mg/kg i.v. (filled inverted triangles) and those additionally dosed at 3 mg/kg i.v. (filled circles).

Mean peak (1R,2R)-2-[(3R)-hydroxypyrrolidinyl]-1-(3,4-dimethoxyphenethoxy)cyclohexane monohydrochloride plasma levels were 5.8 µg/mL (range: 4.0 to 8.6 µg/mL) in the patients that received both the 2.0 and 3.0 mg/kg infusions of (1R, 2R)-2-[(3R)-hydroxypyrrolidinyl]-1-(3,4-dimethoxyphenethoxy)cyclohexane monohydrochloride and 1.9 µg/mL (range: 0.1 to 3.4 µg/mL) in those that received both 0.5 and 1.0 mg/kg (1R,2R)-2-[(3R)-hydroxypyrrolidinyl]-1-(3,4-dimethoxyphenethoxy)cyclohexane monohydrochloride. (FIG. 5) Maximum plasma levels were seen at the end of the second infusion. Plasma drug levels at 24 hours post infusion were below the limit of quantitation (5 ng/ml) in the majority of patients who received RSD-1. Similarly, negligible plasma levels were seen at 24 hours in the RSD-2 group; mean plasma levels were 0.017 µg/mL (range: <0.005 to 0.028 µg/mL).

In those patients that responded to (atrial fibrillation converted) and received only the 2 mg/kg infusion, mean peak plasma levels at the end of infusion were 2.6 µg/mL (range: 1.4 to 4.5 µg/mL). The median plasma level at the time of atrial fibrillation conversion in these patients was 1.3 µg/mL (range: 1.1 to 3.5 µg/mL). The mean terminal elimination half life in these patients was 3.1 hours (range: 1.7-5.4 hours).

This dose-finding study demonstrated that the upper dose of (1R,2R)-2-[(3R)-hydroxypyrrolidinyl]-1-(3,4-dimethoxyphenethoxy)cyclohexane monohydrochloride (2+3 mg/kg) rapidly and effectively terminated atrial fibrillation compared to lower dose (1R,2R)-2-[(3R)-hydroxypyrrolidinyl]-1-(3,4-dimethoxyphenethoxy)cyclohexane monohydrochloride and placebo. (1R,2R)-2-[(3R)-hydroxypyrrolidinyl]-1-(3,4-dimethoxyphenethoxy)cyclohexane monohydrochloride rapidly converted atrial fibrillation patients, often during the infusion phase. There were no serious adverse events associated with (1R,2R)-2-[(3R)-hydroxypyrrolidinyl]-1-(3,4-dimethoxyphenethoxy)cyclohexane monohydrochloride at plasma levels up to 8.6 µg/ml, and observed SAEs were more common in the placebo group. In contrast to other antiarrhythmic drugs used for conversion of acute atrial fibrillation, there were no instances of drug related pro-arrhythmia. While these initial findings will require confirmation in larger scale clinical trials, this safety profile coupled with an efficacious and rapid onset confirms that (1R,2R)-2-[(3R)-hydroxypyrrolidinyl]-1-(3,4-dimethoxyphenethoxy)cyclohexane monohydrochloride is a promising new agent for the medical conversion of acute atrial fibrillation.

Example 2

Pharmacokinetic Evaluation of Oral Dosing in Human Subjects

This prospective, randomized, placebo-controlled, double-blind, ascending dose study was conducted to assess safety and oral absorption of (1R,2R)-2-[(3R)-hydroxypyrrolidinyl]-1-(3,4-dimethoxyphenethoxy)cyclohexane monohydrochloride in healthy volunteers. Safety and tolerance were monitored through 12-lead ECG, Holter and telemetry recordings and monitoring of clinical observations, vital signs, clinical chemistries and hematology. The pharmacokinetics was assessed through measurement of (1R,2R)-2-[(3R)-hydroxypyrrolidinyl]-1-(3,4-dimethoxyphenethoxy)cyclohexane monohydrochloride levels in both urine and plasma.

The $C_{max}$ in fasted volunteers was 1.8±0.4 µg/ml after the 5 mg/kg p.o. dose and 1.9±0.5 µg/ml after the 7.5 mg/kg p.o. dose. In fed volunteers, the $C_{max}$ was 1.3±0.7 µg/ml after the 5 mg/kg p.o. dose. There were no statistically significant differences in $C_{max}$, time to maximum plasma levels ($T_{max}$), or bioavailability (F %) between the groups. The oral bioavailability in the three dosing groups were found to be 71±21% (mean±s.d.), 69±50% and 58±19%, for 5 mg/kg fasted, 5 m/kg fed and 7.5 mg/kg fasted respectively, indicating that (1R,2R)-2-[(3R)-hydroxypyrrolidinyl]-1-(3,4-dimethoxyphenethoxy)cyclohexane monohydrochloride is rapidly and extensively absorbed after oral administration. The plasma levels achieved were well within the therapeutic range (median plasma level at $ED_{50}$=1.3 µg/ml) as observed in the recently completed intravenous trial.

(1R,2R)-2-[(3R)-hydroxypyrrolidinyl]-1-(3,4-dimethoxyphenethoxy)cyclohexane monohydrochloride was found to be well-tolerated in oral doses of up to 7.5 mg/kg. Vital signs, BP and lab results remained normal in all subjects. There were no changes in QT or any ECG intervals observed in any of the dosing groups.

This study was a prospective, randomized, placebo-controlled, double-blind, ascending dose bioavailability study of an orally administered aqueous formulation of (1R, 2R)-2-[(3R)-hydroxypyrrolidinyl]-1-(3,4-dimethoxyphenethoxy)cyclohexane monohydrochloride in healthy volunteers. Pharmacokinetic assessment and safety monitoring endpoints were evaluated. All doses were administered as a single oral dosing solution.

This study was conducted to determine the oral absorption and bioavailability of (1R, 2R)-2-[(3R)-hydroxypyrrolidinyl]-1-(3,4-dimethoxyphenethoxy)cyclohexane monohydrochloride (relative to intravenous administration in a previous study, MDS Pharma Services, Project 26450, August 2001) in normal healthy human volunteers. The study was also conducted to determine the safety and tolerability of (1R,2R)-2-[(3R)-hydroxypyrrolidinyl]-1-(3,4-dimethoxyphenethoxy)cyclohexane monohydrochloride given as a single oral dose of 5.0 or 7.5 mg/kg in fasted and fed (5.0 mg/kg only) normal healthy human volunteers.

The study was a prospective, randomized, placebo-controlled, double-blind ascending single-dose dose assessment of the oral bioavailability of (1R,2R)-2-[(3R)-hydroxypyrrolidinyl]-1-(3,4-dimethoxyphenethoxy)cyclohexane monohydrochloride. Dose ranging covered two doses (5.0 and 7.5 mg/kg) and involved 24 volunteers. The study was conducted in 3 dosing blocks. After completion of each dosing block and assessment of clinically significant findings, the blind was broken and (1R,2R)-2-[(3R)-hydroxypyrrolidinyl]-1-(3,4-dimethoxyphenethoxy)cyclohexane monohydrochloride plasma levels were analyzed prior to continuation of the next dosing block. Interim safety review meetings were held to review all of the available data after dosing blocks 1 and 2.

All subjects were admitted to the study facility the evening before dosing and were monitored for 24-hours in the facility post-dose with a 1-week+/−3 days follow-up visit. Volunteers received a single dose (150 ml solution) of (1R,2R)-2-[(3R)-hydroxypyrrolidinyl]-1-(3,4-dimethoxyphenethoxy)cyclohexane monohydrochloride or placebo given on one occasion. The first 8 subjects were randomized to receive either placebo (n=2) or to receive a single oral administration of 5.0 mg/kg oral dose (n=6). The first 8 subjects were fasted from midnight prior to dosing until four hours post-dose. The second group of subjects were assessed at the same dose (5 mg/kg) with fed subjects (n=6) and placebo (n=2). A standard breakfast was administered concomitant with dosing. The third group of 8 subjects were randomized to receive either placebo (n=2) or to receive a single oral administration of 7.5 mg/kg (n=6). These subjects were fasted from midnight prior to dosing until four hours post-dose.

The subjects for this study were normal, healthy males and females as defined by the inclusion and exclusion criteria described below:

Inclusion Criteria
 a) Females and males aged 18 between 60 years. Females must be non-pregnant and surgically sterile or free of menses for more than two years. If free of menses females must be using an effective form of birth control during the study (from pre-screening) until three months after the follow-up visit. Methods of birth control considered to be effective would include hormonal contraception (the pill), an intrauterine device (IUD), condoms in combination with a spermicidal cream, total abstinence or sterilization. Males will be advised to refrain from unprotected sexual intercourse (i.e., without adequate contraceptive method) until three months after the follow-up screening).
 b) No clinically important abnormal physical findings at the screening examination.
 c) Normal ECG.
 d) Body weight between 45 to 95 kg and a body mass index of 18-27 $kg/m^2$.
 e) Able to communicate well with the investigator and to comply with the requirements of the entire study.
 f) Provision of written informed consent to participate as shown by a signature on the volunteer consent form.

Exclusion Criteria
 a) 90 mmHg>systolic blood pressure>160 mmHg, or, 65 mm Hg>diastolic pressure>95 mmHg. These will be measured 3 times after sitting for 3 minutes and averaged to determine a baseline BP.
 b) 50 bpm≧pulse rate≧90 bpm.
 c) PR>0.21 sec, QRS>0.11 sec, $QT_cB$>0.430 sec for men and $QT_cB$>0.450 sec for women.
 d) Participation in any other investigational drug study within 60 days preceding the start of the study, or participation in more than 3 other drug studies (for men)/more than 2 other drug studies (for women) in the past 10 months.
 e) Administration of prescription or over-the-counter medication during the period 0 to 5 days before entry to the study including aspirin. (Exceptions to this criterion include the use of hormone replacement therapy or oral contraceptives by female subjects.)

f) Administration of antacids, gastric reflux, anti-ulcer or gastrointestinal pro-kinetic medications in the period of 0 to 30 days before entry to the study unless agreed upon by Sponsor and Investigator.
g) Existence of any surgical or medical condition which, in the judgment of the clinical investigator, might interfere with the absorption, distribution, metabolism or excretion of the drug.
h) Donation of blood within 60 days preceding the start of the study, or, donation of more than 1.5 liters of blood (for men)/more than 1.0 liters of blood (for women) in the past 10 months. (The exception to this criterion is, blood sampling for screening, admission and baseline tests for this study is permitted.)
i) Loss of greater than 250 ml of blood within 60 days preceding the start of the study.
j) Known serious adverse reaction or hypersensitivity to any drug.
k) Inability to communicate or co-operate with the investigator because of a language problem, poor mental development or impaired cerebral function.
l) Positive drug screen, positive Ab to HIV, HCV, and positive Ag to HBV
m) History of drug or alcohol abuse.
n) Abnormal screening test results (clinical chemistry, hematology or urinalysis).
o) Family history of QT abnormalities or congenital QT syndrome.
p) Any herbal or alternate medicines during the period 0 to 5 days before entry to the study.
q) Frequent use of antacids
r) History of gastro-intestinal or cardiovascular problems.
s) Any other condition that, in the opinion of the clinical investigator, would make it unwise to enter the subject into the study.

No alcohol, caffeine or smoking were permitted from admission to the study facility to discharge. No herbal remedies, medicines or alternative medicines were permitted from admission to the study facility to discharge with the exception of aspirin/paracetamol which was permitted from 4 h post-dose onwards.

Dosing was to be terminated if any volunteer that exhibited any significant clinical signs (e.g. tremors) or if the following limits were reached: PR>0.24 s; QTcB>0.500s; Pulse Rate<40 bpm; Systolic BP<80 mm Hg (confirmed by three measurements over three minutes); Evidence of bundle branch block or other serious conduction disturbance.

The subject population included men (63%) and women in the age range of 18-60 years. Subject body weight ranged from 59.1 to 89.3 kg. Subjects meeting entry criteria and signing informed consent forms were enrolled in the study. Each subject was assessed clinically pre-dose and underwent clinical and pharmacokinetic evaluation during and after dosing. Each subject enrolled in the study was characterized for cytochrome P450 2D6 expression by genotyping using a blood sample.

The study drug was administered in a volume of 150 mL by oral administration. If drug/placebo was administered to fed subjects, then drug/placebo was administered to subjects with a standard breakfast. Subjects remained sitting during drug administration and it was encouraged that they remained sitting for approximately 4 hours post-dose. Telemetry monitoring was conducted from baseline until at least 4 hours post-dose. Vital signs measurements including pulse rate, respiration rate, blood pressure and oxygen saturation were taken at the following timepoints: screening; admission; pre-dose; immediately following dosing; 0.25, 0.5, 1, 2, 4, 6, 8, and 24 hours after drug/placebo administration; at follow-up visit; and in the event of an SAE (none occurred). 12-lead ECGs were recorded at the following timepoints: screening; admission; pre-dose; immediately following dosing; 0.25, 0.5, 1, 2, 4, 6, 8, and 24 hours after drug/placebo administration; at follow-up visit; and in the event of an SAE (none occurred). ECG's were interpreted by a board-certified cardiologist selected by the Sponsor. Baseline and screening 12-lead ECGs were recorded three times consecutively after subject had been sitting for 10 minutes. The ECG recording with the median of the three QTcB interval measurements was used as the ECG for that timepoint. Blood (5 mL) for pharmacokinetic analysis were drawn at the following timepoints via venipuncture or sampling cannula into lithium heparin tubes: pre-dose, 0.25, 0.5, 1, 2, 4, 6, 8 and 24 hours after drug/placebo administration and in the event of an SAE (none occurred). Pharmacokinetic (PK) parameters for each subject were calculated using WinNonlin (Pharsight Corp., Palo Alto, Calif., USA). A non-compartmental model was used to calculate parameter estimates. The oral bioavailability of (1R,2R)-2-[(3R)-hydroxypyrrolidinyl]-1-(3,4-dimethoxyphenethoxy)cyclohexane monohydrochloride was calculated using the area under the curves (AUCs) after oral administration compared to the AUCs obtained after iv administration in a previously completed study (Phase I trial report). Urine was collected each time the subject voided. After dosing specimens were collected over the periods; 0-4 hours, 4-8 hours and 8 hours-discharge. Clinical chemistry, hematology, and urinalysis at screening, admission, at 1 hour post-dose and at discharge. Holter monitoring continued for up to 24 hours post-dose. Holter monitors were read at a central reading centre. The nature of any adverse event, its time of onset, its duration and severity, action taken, if any, and the investigator's opinion as to whether it was related to the test drug was recorded on the AE Form. Duration of the follow up of an adverse event was until recovery from the event was evident, or until the event was judged medically stable or permanent. Subjects were monitored in the study facility until all adverse events resolved.

Figure 6:
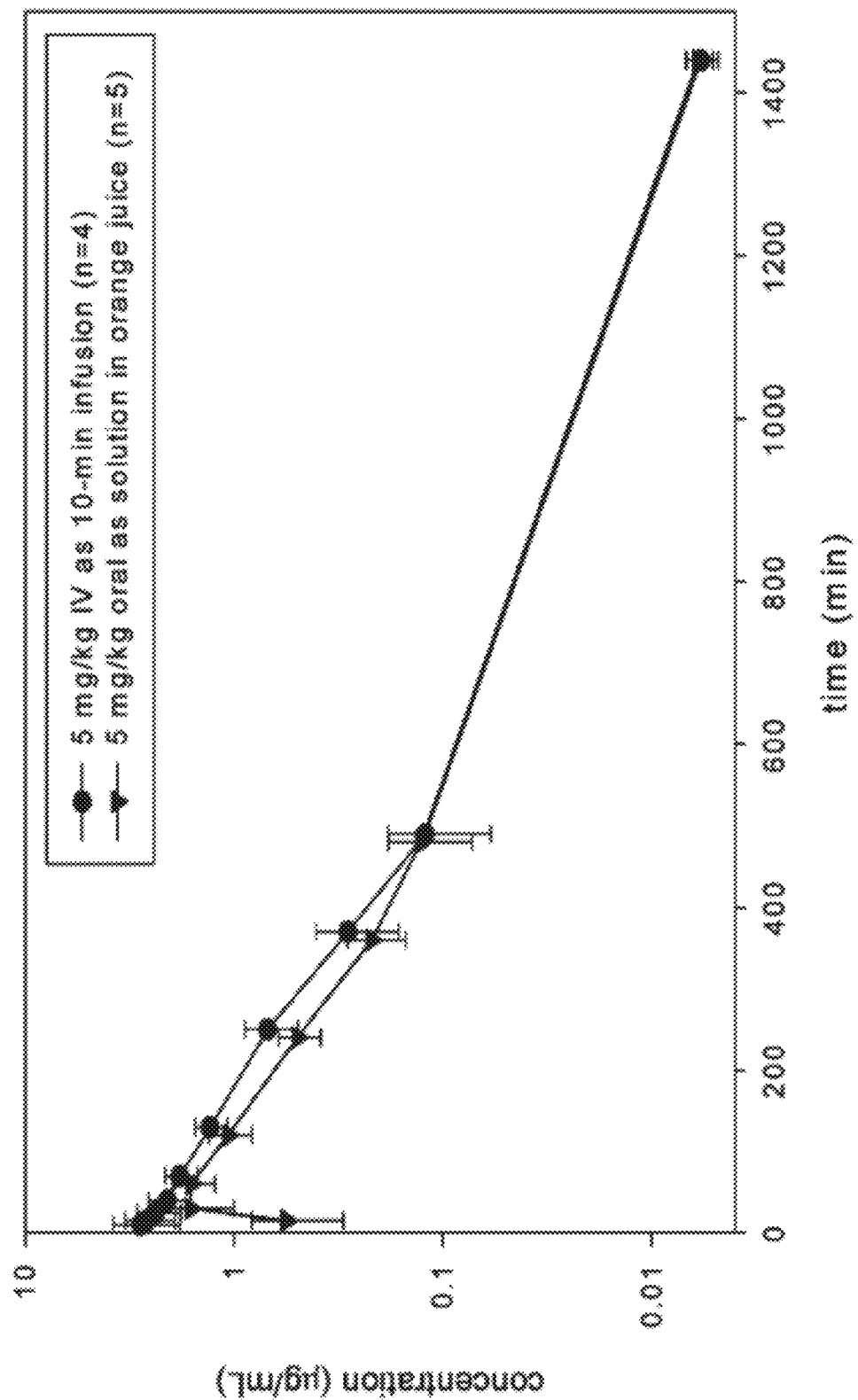
FIG. 6 shows (1R,2R)-2-[(3R)-hydroxypyrrolidinyl]-1-(3, 4-dimethoxyphenethoxy)cyclohexane monohydrochloride plasma concentrations at various times after IV (10-min infusion) or oral drug administration (solution in orange juice) to normal volunteers (dose 5 mg/kg).
Figure 7:
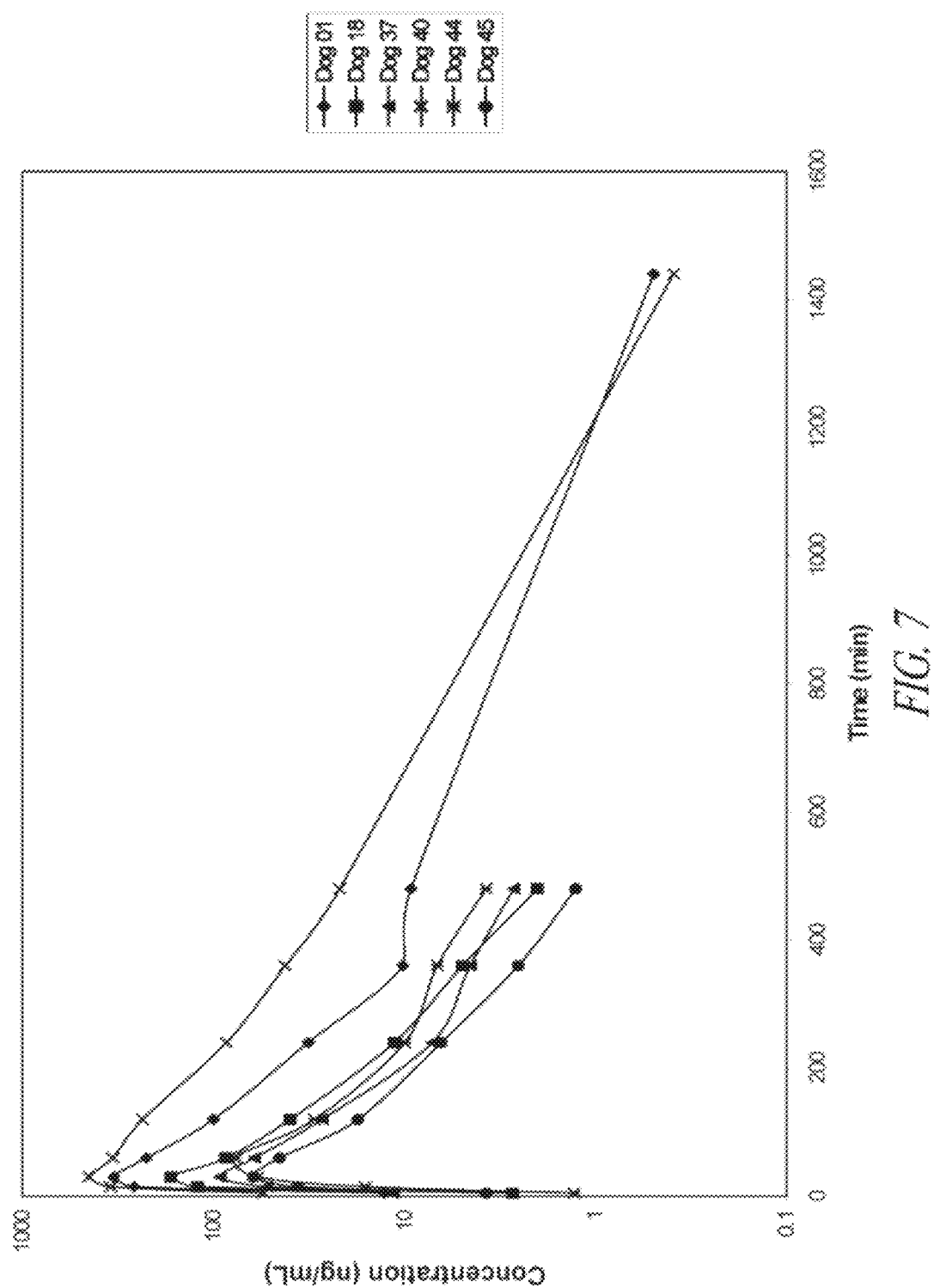
FIG. 7 shows individual Plasma Concentration of (1R,2R)-2-[(3R)-hydroxypyrrolidinyl]-1-(3,4-dimethoxyphenethoxy)cyclohexane monohydrochloride Versus Time Following Oral Gavage Administration in Beagle Dogs.
Figure 8:
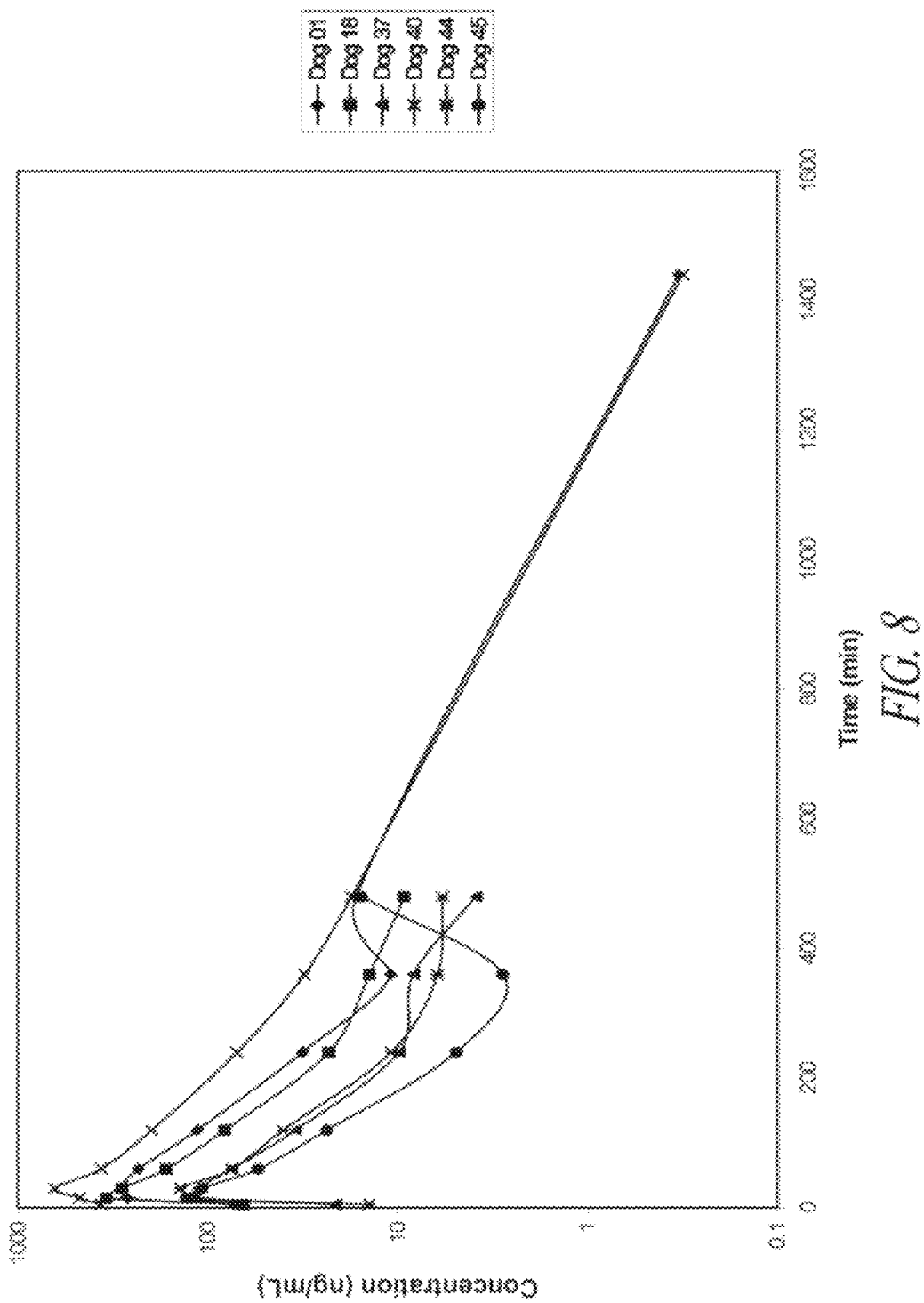
FIG. 8 shows individual Plasma Concentration of (1R,2R)-2-[(3R)-hydroxypyrrolidinyl]-1-(3,4-dimethoxyphenethoxy)cyclohexane monohydrochloride Versus Time Following Intraduodenal Administration in Beagle Dogs.
Figure 9:
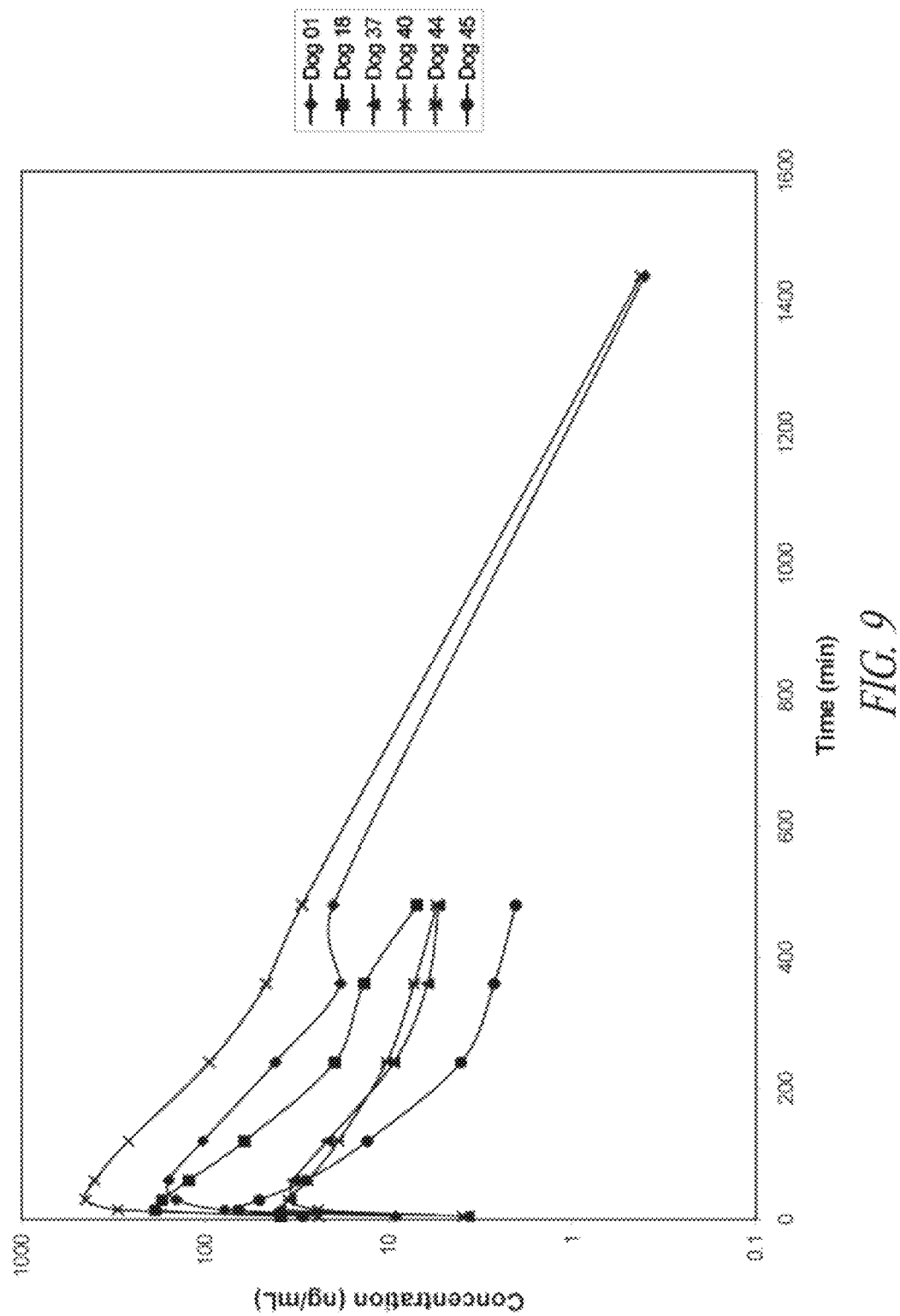
FIG. 9 shows individual Plasma Concentration of (1R,2R)-2-[(3R)-hydroxypyrrolidinyl]-1-(3,4-dimethoxyphenethoxy)cyclohexane monohydrochloride Versus Time Following Intracolonic Administration in Beagle Dogs.

The study drug showed rapid and extensive absorption after a single oral dose in both fasted and fed subjects (Table 11 and FIG. 6). The majority of subjects achieved maximal plasma levels ($C_{max}$) within 30-60 minutes of dosing. The $C_{max}$ in fasted subjects was 1.8±0.4 µg/ml after the 5 mg/kg p.o. dose and 1.3±0.7 µg/ml after the 5 mg/kg p.o. dose in fed subjects. The $C_{max}$ in fasted subjects was 1.9±0.5 µg/ml after the 7.5 mg/kg p.o. dose. There were no statistically significant differences in $C_{max}$, time to maximum plasma levels ($T_{max}$), or bioavailability (F %) between the groups. One subject with slow clearance and a bioavailability of approximately 240% (#05) was excluded from the bioavailability calculations.

TABLE 11

PK and Bioavailability Results

|  | 5 mg/kg fasted | 5 mg/kg fed | 7.5 mg/kg fasted |
| --- | --- | --- | --- |
| Cmax (µg/ml) | 1.8 ± 0.4 | 1.3 ± 0.7 | 1.9 ± 0.5 |
| Tmax (min) | 55 ± 35 | 70 ± 41 | 45 ± 16 |
| AUCall | 470 ± 330 | 330 ± 250 | 290 ± 70 |
| AUCinf | 490 ± 350 | 340 ± 240 | 300 ± 80 |
| AUC/dose | 98 ± 71 | 67 ± 49 | 57 ± 19 |
| F % | 71 ± 21* | 69 ± 50 | 58 ± 19 |
| (min-max) | (46-105)* | (15-139) | (33-89) |

*excluding one outlier (F = 240%)

The oral bioavailability in the three dosing groups were found to be 71±21% (mean±s.d.), 69±50% and 58±19%, for 5 mg/kg fasted, 5 m/kg fed and 7.5 mg/kg fasted respectively, indicating that (1R,2R)-2-[(3R)-hydroxypyrrolidinyl]-1-(3,4-dimethoxyphenethoxy)cyclohexane monohydrochloride is rapidly and extensively absorbed after oral administration. The plasma levels achieved were well within the therapeutic range (median plasma level at $ED_{50}$=1.3 μg/ml) as observed in the recently completed intravenous studies.

The study drug was well tolerated at oral doses of 5-7.5 mg/kg in normal healthy volunteers. Vital signs, BP and lab results remained normal in all subjects. Almost all of the adverse events observed were considered not related to drug and all except one of the observations were mild in nature. Single observations of loose stools, bitter taste and a visual disturbance were considered possibly related to drug. A further volunteer reported two episodes of transient paraesthesia of the right hand that was also considered possibly related to drug. There were no significant changes in clinical laboratory tests or vital signs. There were no clinically relevant changes observed in QTcB, QT, JT, PR, QRS, or HR intervals and no clinically significant findings found in the Holter recordings.

yphenethoxy)cyclohexane monohydrochloride (lot#BC-145-39, 99.3% active) was weighed into a precleaned 20 mL glass vial. 21 mLs of water was added and the sample was inverted several times to dissolve all powder. At the time of dosing all solutions were clear.

The pharmacokinetics of (1R,2R)-2-[(3R)-hydroxypyrrolidinyl]-1-(3,4-dimethoxyphenethoxy)cyclohexane monohydrochloride was evaluated in male beagle dogs ranging in age from 1 to 2 years. All animals were housed one per cage. The animals were fasted for a minimum of 12 hours prior to dosing. Food was returned to the animals at four hours postdose. Water was withheld for one hour predose and supplied ad libitum at one hour postdose. The same six beagle dogs (crossover design) were used for each dosing leg of the study. All animals were dosed on the same day via the same route of administration. The numbers of the animals and the dosing regimen are presented in Table 12.

TABLE 12

Study Design

| STUDY LEG | DOG# | WEIGHT (KG) | ROUTE OF ADMINISTRATION | DOSE VOLUME (ML/KG) | DOSE (MG/KG) |
|---|---|---|---|---|---|
| I | 01-(10213) | 12.9 | ORAL GAVAGE | 0.25 | 5.0 |
|  | 18-(20352) | 9.6 | ORAL GAVAGE | 0.25 | 5.0 |
|  | 37-(20741) | 9.6 | ORAL GAVAGE | 0.25 | 5.0 |
|  | 40-(20941) | 9.4 | ORAL GAVAGE | 0.25 | 5.0 |
|  | 44-(10102) | 12.3 | ORAL GAVAGE | 0.25 | 5.0 |
|  | 45-(20191) | 12.1 | ORAL GAVAGE | 0.25 | 5.0 |
| II | 01-(10213) | 12.9 | INTRADUODENAL | 0.25 | 5.0 |
|  | 18-(20352) | 9.4 | INTRADUODENAL | 0.25 | 5.0 |
|  | 37-(20741) | 9.6 | INTRADUODENAL | 0.25 | 5.0 |
|  | 40-(20941) | 9.5 | INTRADUODENAL | 0.25 | 5.0 |
|  | 44-(10102) | 12.4 | INTRADUODENAL | 0.25 | 5.0 |
|  | 45-(20191) | 11.8 | INTRADUODENAL | 0.25 | 5.0 |
| III | 01-(10213) | 13.1 | INTRACOLONIC | 0.25 | 5.0 |
|  | 18-(20352) | 9.6 | INTRACOLONIC | 0.25 | 5.0 |
|  | 37-(20741) | 9.7 | INTRACOLONIC | 0.25 | 5.0 |
|  | 40-(20941) | 9.7 | INTRACOLONIC | 0.25 | 5.0 |
|  | 44-(10102) | 12.8 | INTRACOLONIC | 0.25 | 5.0 |
|  | 45-(20191) | 12.2 | INTRACOLONIC | 0.25 | 5.0 |

Example 3

Pharmacokinetic Evaluation of (1R,2R)-2-[3R)-Hydroxyprrolidinyl]-1-(3,4-Dimethoxyphenethoxy)cyclohexane monohydrochloride in Dogs In this study, the pharmacokinetics of (1R,2R)-2-[(3R)-hydroxypyrrolidinyl]-1-(3,4-dimethoxyphenethoxy)cyclohexane monohydrochloride in beagle dogs after dosing via oral gavage, intraduodenally (ID) and intracolonically (IC) was investigated. Pharmacokinetic parameters such as $AUC_{0-t}$, $C_{max}$ and $T_{max}$ were determined. The segmental dependence to absorption of (1R,2R)-2-[(3R)-hydroxypyrrolidinyl]-1-(3,4-dimethoxyphenethoxy)cyclohexane monohydrochloride was also evaluated.

Dosing solutions for all routes of administration were prepared using the same procedure as follows: 425 mg of (1R,2R)-2-[(3R)-hydroxypyrrolidinyl]-1-(3,4-dimethox- Animals were dosed via a chronic intraduodenal or colonic access port or by oral gavage. Blood samples were taken from a foreleg vein via a butterfly catheter at the following time points: Oral gavage, ID and IC: 0 (pre-dose), 5, 15, 30, 60, 120, 240, 360, 480 and 1440 minutes postdose. The blood samples were withdrawn and placed into tubes containing sodium heparin as anticoagulant. Blood samples were then centrifuged at 3,000 rpm for 15 minutes at 4° C.

(1R,2R)-2-[(3R)-hydroxypyrrolidinyl]-1-(3,4-dimethoxyphenethoxy)cyclohexane monohydrochloride was extracted from the plasma via solid phase extraction then analyzed by LC/MS/MS. Pharmacokinetic analysis was performed on the plasma concentration of (1R, 2R)-2-[(3R)-hydroxypyrrolidinyl]-1-(3,4-dimethoxyphenethoxy)cyclohexane monohydrochloride for each individual dog at each time point. The data were subjected to non-compartmental analysis using the pharmacokinetic program WinNonLin v. 4.1 (1). Pharmacokinetic parameters are given in Tables 13, 14, and 15.

TABLE 13

Pharmacokinetic Parameters of (1R,2R)-2-[(3R)-hydroxypyrrolidinyl]-1-(3,4-dimethoxyphenethoxy)cyclohexane monohydrochloride after Oral Gavage Administration

| Test Article | Dog | $AUC_{last}$ (min · ng/mL) | $C_{max}$ (ng/mL) | $T_{max}$ (min) |
|---|---|---|---|---|
| COMPOUND A | 01 | 40165 | 332 | 30 |
| | 18 | 14811 | 167 | 30 |
| | 37 | 9568 | 92.6 | 30 |
| | 40 | 78324 | 447 | 30 |
| | 44 | 9883 | 76.8 | 60 |
| | 45 | 6624 | 61.8 | 30 |
| | Average (±SD, N = 6) | 26563 ± 28167 | 196 ± 158 | 35 ± 12 |
| | Average* (±SD, N = 5) | 16211 ± 12263 | 146 ± 100 | 36 ± 12 |

*Average of N = 5, Dog 40 is removed from these averages

TABLE 14

Pharmacokinetic Parameters of (1R,2R)-2-[(3R)-hydroxypyrrolidinyl]-1-(3,4-dimethoxyphenethoxy)cyclohexane monohydrochloride after Intraduodenal Administration

| Test Article | Dog | $AUC_{last}$ (min · ng/mL) | $C_{max}$ (ng/mL) | $T_{max}$ (min) |
|---|---|---|---|---|
| COMPOUND A | 01 | 45301 | 286 | 30 |
| | 18 | 30992 | 343 | 15 |
| | 37 | 13106 | 122 | 15 |
| | 40 | 79131 | 639 | 30 |
| | 44 | 14056 | 140 | 30 |
| | 45 | 10960 | 130 | 15 |
| | Average (±SD, N = 6) | 32257 ± 26535 | 277 ± 200 | 23 ± 8.2 |
| | Average* (±SD, N = 5) | 22883 ± 13296 | 204 ± 92 | 21 ± 7.3 |

*Average of N = 5, Dog 40 is removed from these averages

TABLE 15

Pharmacokinetic Parameters of (1R,2R)-2-[(3R)-hydroxypyrrolidinyl]-1-(3,4-dimethoxyphenethoxy)cyclohexane monohydrochloride after Intracolonic Administration

| Test Article | Dog | $AUC_{last}$ (min · ng/mL) | $C_{max}$ (ng/mL) | $T_{max}$ (min) |
|---|---|---|---|---|
| COMPOUND A | 01 | 38891 | 158 | 60 |
| | 18 | 21948 | 187 | 15 |
| | 37 | 6923 | 39.1 | 15 |
| | 40 | 88823 | 449 | 30 |
| | 44 | 6495 | 35.1 | 30 |
| | 45 | 5560 | 65.8 | 15 |
| | Average (±SD, N = 6) | 28107 ± 32449 | 156 ± 157 | 28 ± 18 |
| | Average* (±SD, N = 5) | 15964 ± 12970 | 97 ± 63 | 27 ± 17.5 |

*Average of N = 5, Dog 40 is removed from these averages

No adverse reactions were observed following oral gavage, intraduodenal or intracolonic administration of (1R,2R)-2-[(3R)-hydroxypyrrolidinyl]-1-(3,4-dimethoxyphenethoxy)cyclohexane monohydrochloride in beagle dogs.

The nominal concentration of the dosing solutions was 20 mg/mL. The dosing solutions were analyzed post-dosing and the concentrations were determined to be 16.6, 17.0 and 17.5 mg/mL for the oral gavage, intraduodenal and intracolonic dosing solutions, respectively. These values were used in all calculations.

Average plasma concentrations (±SD) of (1R,2R)-2-[(3R)-hydroxypyrrolidinyl]-1-(3,4-dimethoxyphenethoxy)cyclohexane monohydrochloride for each point and route of administration are shown in Table 16.

TABLE 16

AVERAGE ± SD (N = 6) PLASMA CONCENTRATIONS (NG/ML) OF (1R,2R)-2-[(3R)-hydroxypyrrolidinyl]-1-(3,4-dimethoxyphenethoxy)cyclohexane monohydrochloride

| Route of Administration | Pre-dose | Time (min) | | | | | | | | |
| | | 5 | 15 | 30 | 60 | 120 | 240 | 360 | 480 | 1440* |
|---|---|---|---|---|---|---|---|---|---|---|
| Oral Gavage | 0 | 14.5 ± 20.4 | 138 ± 135 | 193 ± 161 | 138 ± 116 | 74.8 ± 83.8 | 25.4 ± 30.9 | 11.8 ± 15.0 | 6.80 ± 7.88 | 0.44 |
| Intraduodenal | 0 | 101 ± 133 | 242 ± 147 | 261 ± 202 | 162 ± 121 | 82.0 ± 66.2 | 25.1 ± 24.2 | 12.2 ± 9.95 | 11.4 ± 5.89 | 0.32 |
| Intracolonic | 0 | 18.2 ± 14.7 | 116 ± 107 | 148 ± 159 | 128 ± 144 | 80.0 ± 95.5 | 30.0 ± 34.5 | 15.7 ± 16.1 | 11.6 ± 10.9 | 0.41 |

*All 1440 minute concentrations are reported as N = 2. The concentration of (1R,2R)-2-[(3R)-hydroxypyrrolidinyl]-1-(3,4-dimethoxyphenethoxy)cyclohexane monohydrochloride at 1440 minutes for four of the animals (18, 37, 44 and 45) was below the lower limit of quantitation.

FIGS. 7-10 contain graphical representations of the plasma concentration versus time curves for (1R,2R)-2-[(3R)-hydroxypyrrolidinyl]-1-(3,4-dimethoxyphenethoxy)cyclohexane monohydrochloride in dog.

The average AUClast, $C_{max}$ and $T_{max}$ were similar for all three routes of (1R,2R)-2-[(3R)-hydroxypyrrolidinyl]-1-(3,4-dimethoxyphenethoxy)cyclohexane monohydrochloride administration (Tables 3-6). Compared to other dogs used in the study, dog number 40 had significantly higher AUClast and $C_{max}$ values at all routes tested (Tables 3-6). The reason for the higher AUClast and $C_{max}$ values in this animal is not apparent from the available data. The observed higher values could be, at least partially due to lower systemic clearance of (1R, 2R)-2-[(3R)-hydroxypyrrolidinyl]-1-(3,4-dimethoxyphenethoxy)cyclohexane monohydrochloride in this dog; however, in the absence of intravenous dosing data, it is not possible to confirm this hypothesis. Due to this uncertainty, the average values for AUClast, $C_{max}$ and Tmax were also calculated without data from this animal.

Figure 10:
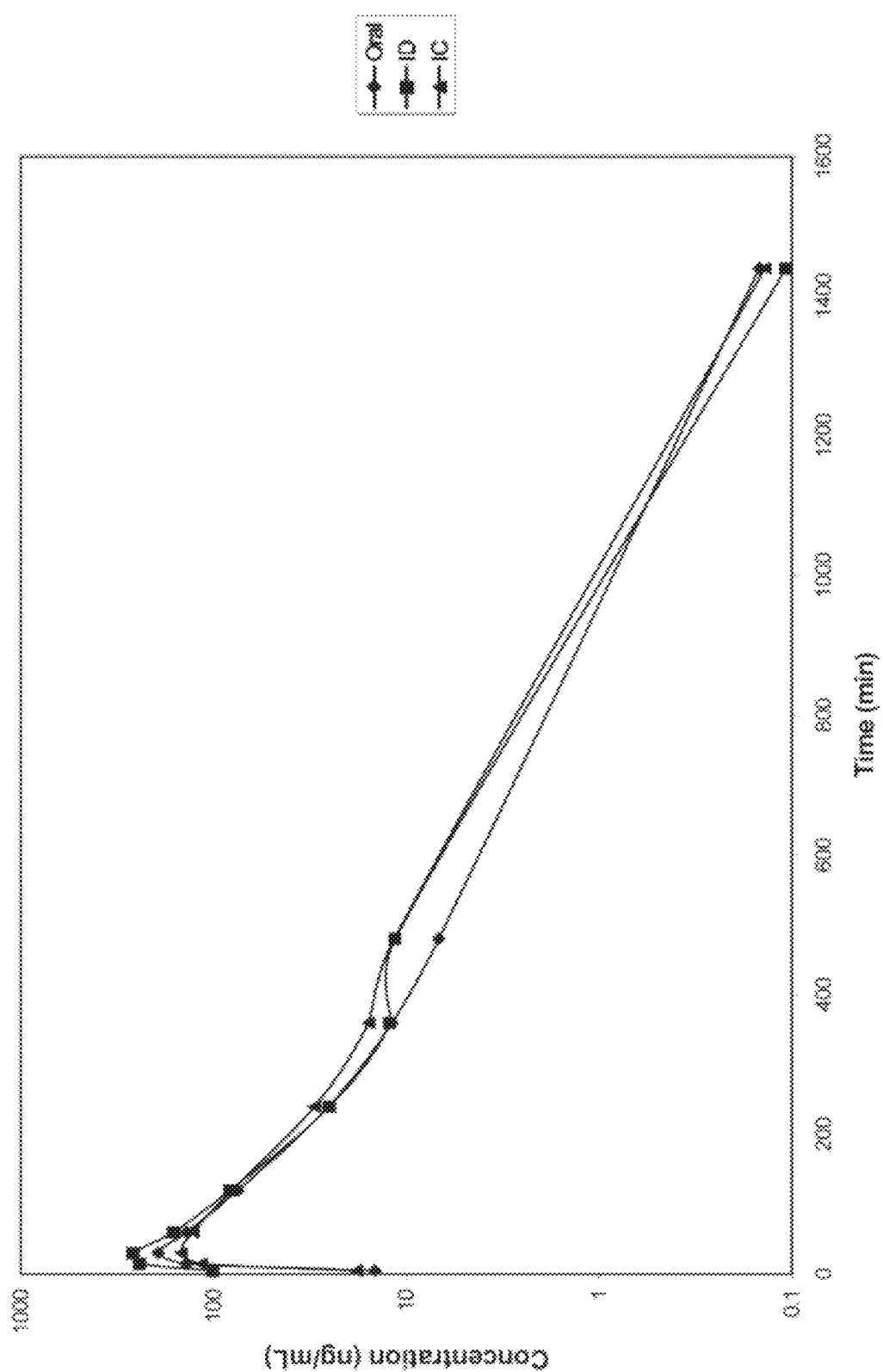
FIG. 10 shows average plasma concentration of (1R,2R)-2-[(3R)-hydroxypyrrolidinyl]-1-(3,4-dimethoxyphenethoxy)cyclohexane monohydrochloride Versus time following administration in beagle dogs (N=6), all routes compared.
Figure 11:
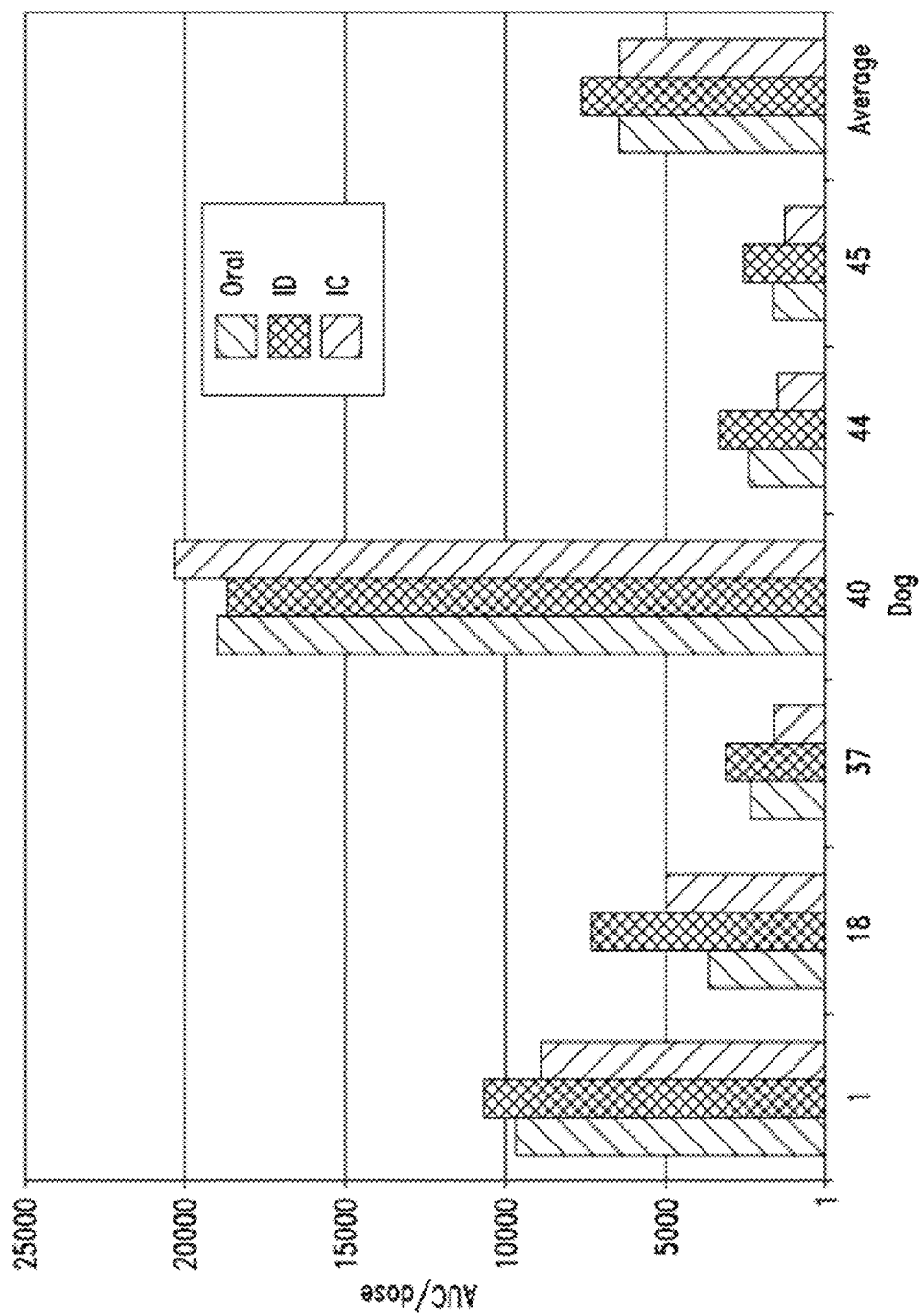
FIG. 11 shows dose normalized AUCs of (1R,2R)-2-[(3R)-hydroxypyrrolidinyl]-1-(3,4-dimethoxyphenethoxy)cyclohexane monohydrochloride for each route of administration in beagle dogs.

Administration of the (1R,2R)-2-[(3R)-hydroxypyrrolidinyl]-1-(3,4-dimethoxyphenethoxy)cyclohexane monohydrochloride via oral gavage, intraduodenal or intracolonic routes resulted in similar AUC/dose values (FIG. 11) for each dog used in this study. Furthermore, average AUClast, $C_{max}$, Tmax and AUC/dose were also similar for all three routes of (1R,2R)-2-[(3R)-hydroxypyrrolidinyl]-1-(3,4-dimethoxyphenethoxy)cyclohexane monohydrochloride administration (FIG. 10 and Tables 3-6). These data suggest that (1R,2R)-2-[(3R)-hydroxypyrrolidinyl]-1-(3,4-dimethoxyphenethoxy)cyclohexane monohydrochloride is absorbed approximately equally following oral gavage, intraduodenal or colonic administration.

All references, patents, and patent applications described in this patent are incorporated herein by reference to the full extent as though each reference, patent, or patent application had been individually incorporated by reference.

Example 4

Pharmacokinetics of and Ion Channel Modulating Compound Following Single Oral Administration to Male Beagle Dogs after 7 Days of 4 Daily Doses The purpose of this study was to investigate the pharmacokinetics of DRUG injection following single oral administration to male beagle dogs after 7 days of 4 daily doses.

The ion channel modulating compound applied was (1R,2R)-2-[(3R)-Hydroxypyrrolidinyl]-1-(3,4-dimethoxyphenethoxy)cyclohexane monohydrochloride ($C_{20}H_{31}NO_4 \cdot HCl$) (referred to as "drug" in this example). This drug was prepared and diluted according to protocol specifications as follows:

| Formulation Preparation | Formulation Use | Formulation Preparation Description |
| --- | --- | --- |
| Study Day −1 | Study Day 1 | Group 1: DRUG injection solution (10 mL) was diluted with 30 mL of sterile water at a target concentration of 5 mg/mL. Group 2: DRUG injection solution (16.5 mL) was diluted with 16.5 mL of sterile water at a target concentration of 10 mg/mL. |
| Study Day 1 | Study Days 2-5 | Group 1: DRUG injection solution (160 mL) was diluted with 480 mL of sterile water at a target concentration of 5 mg/mL Group 2: DRUG injection solution (264 mL) was diluted with 264 mL of sterile water at a target concentration of 10 mg/mL. |
| Study Day 5 | Study Days 6-8 | Group 1: DRUG injection solution (120 mL) was diluted with 360 mL of sterile water at a target concentration of 5 mg/mL. Group 2: DRUG injection solution (198 mL) was diluted with 198 mL of sterile water at a target concentration of 10 mg/mL. |
| Study Day 8 | Study Day 9 | Group 1: DRUG injection solution (11.75 mL) was diluted with 35.25 mL of sterile water at a target concentration of 5 mg/mL. Group 2: DRUG injection solution (20 mL) was diluted with 20 mL of sterile water at a target concentration of 10 mg/mL. |

Dose formulation samples (0.1 mL) were collected from each formulation prior to dosing on Study Days—1, 1, 4, and 8. Dose formulation samples (0.1 mL) were also collected from each formulation following the first dose of each day (Study Days 1, 2, 5, 7, and 8). Samples were used to verify the concentration of the dose applied.

Six male beagle dogs were selected from non-naive animals. The animals were assigned to the study based on acceptable health as determined by the attending veterinarian following a pre-study health evaluation. The pre-study health evaluation included a physical exam, serum chemistry and hematology evaluations. The animals were placed into two groups of 3 animals per group. Study animals were fasted overnight prior to dosing for Study Days 1 and 9 only, and food was returned approximately 4 hours post-dose. Fasting was not required on Study Days 2-8 (multiple dosing days).

On Study Days 1 and 9, Group 1 animals received a single dose of prepared drug via oral gavage at a target dose level of 5 mg/kg and at a dose volume of 1 mL/kg. On Study Days 1 and 9, Group 2 animals received a single dose of prepared drug via oral gavage at a target dose level of 10 mg/kg and at a dose volume of 1 mL/kg. On Study Days 2-8, Group 1 and 2 animals received prepared drug 4 times daily (every 6 hours). Immediately following each dose, the gavage tube was flushed with approximately 10 mL of water prior to removal. Dosing proceeded according to protocol and without incident with the following exceptions:

| Study Day | Group Number | Study Number | Dosing Observation |
|---|---|---|---|
| 5 (Dose 1) | 1 | 1001 | Water flush was not administered immediately following dose. Animal received the water flush following the later doses of the same day. |
| 7 (Dose 3) | 2 | 2001 | While confirming placement of the gavage tube in the stomach, a red substance was observed in the gavage tube. |

Throughout dosing and sample collection, the animals were observed for any clinically relevant abnormalities and the following were observed:

| Study Day | Group Number | Study Number | Clinical Observation |
|---|---|---|---|
| 1 | 1 | 1002 | Excessive salivation was observed approximately 6 minutes post-dose. This condition was not observed at subsequent observations. |
| 2 (Dose 1) | 1 | 1003 | Soft feces (mild) was observed immediately prior to first dose. This condition was not observed at subsequent observations. |
| 7 (Dose 1) | 1 | 1001 | Emesis (~10 mL of food) was observed approximately 2 hours 25 minutes following first dose. This condition was not observed at subsequent observations. |

For Study Days 1 and 9, whole blood samples (1 mL, Heparin anticoagulant) were collected from Groups 1 and 2 prior to dosing and at 0.083, 0.25, 0.50, 1, 2, 4, 6, 8, and 24 hours post-dose. For Study Days 2-8, whole blood samples were collected prior to the first morning dose of each day for Groups 1 and 2. Whole blood samples were placed in an ice bath immediately upon collection for processing. A refrigerated centrifuge (3500 rpm for ~10 minutes at 5±3° C.) was used to process whole blood to plasma.

Results

Figure 12:
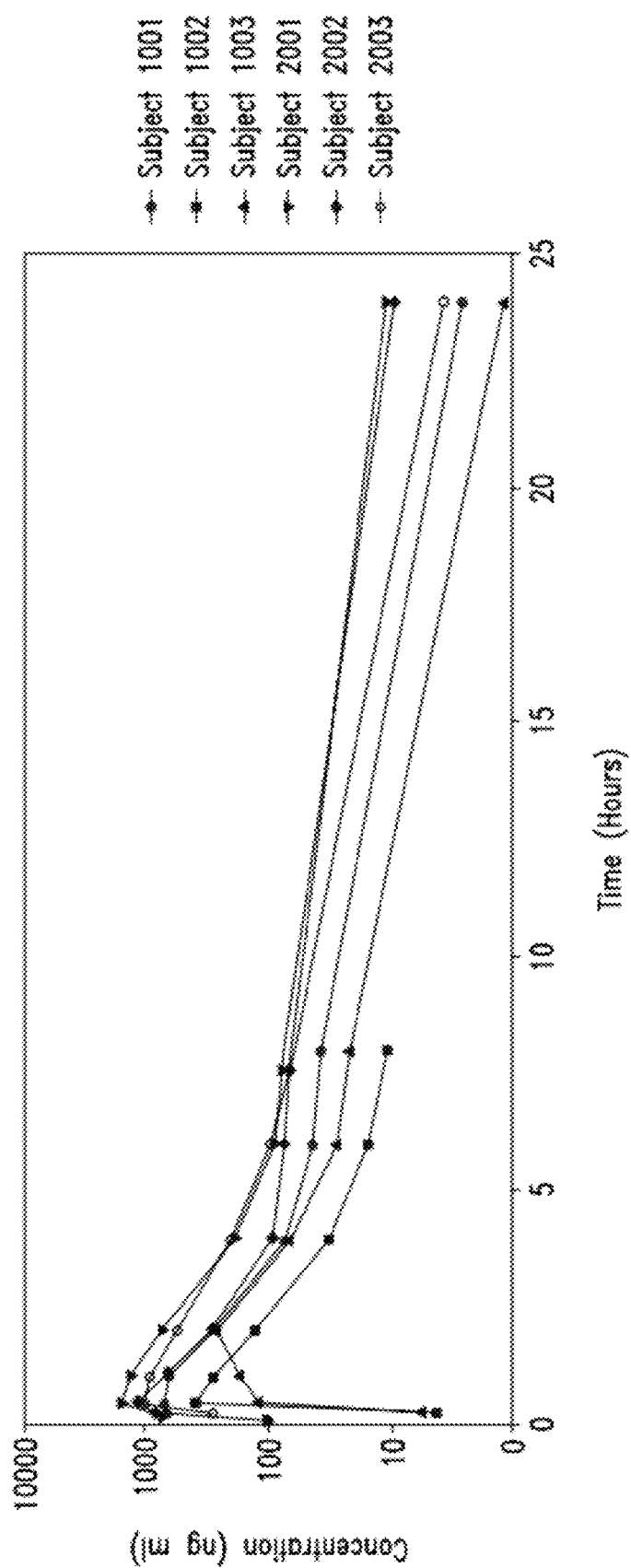
FIG. 12 shows the plasma concentration levels of (1R,2R)-2-[(3R)-hydroxypyrrolidinyl]-1-(3,4-dimethoxyphenethoxy)cyclohexane monohydrochloride after a single oral dose in six dog subjects.
Figure 13:
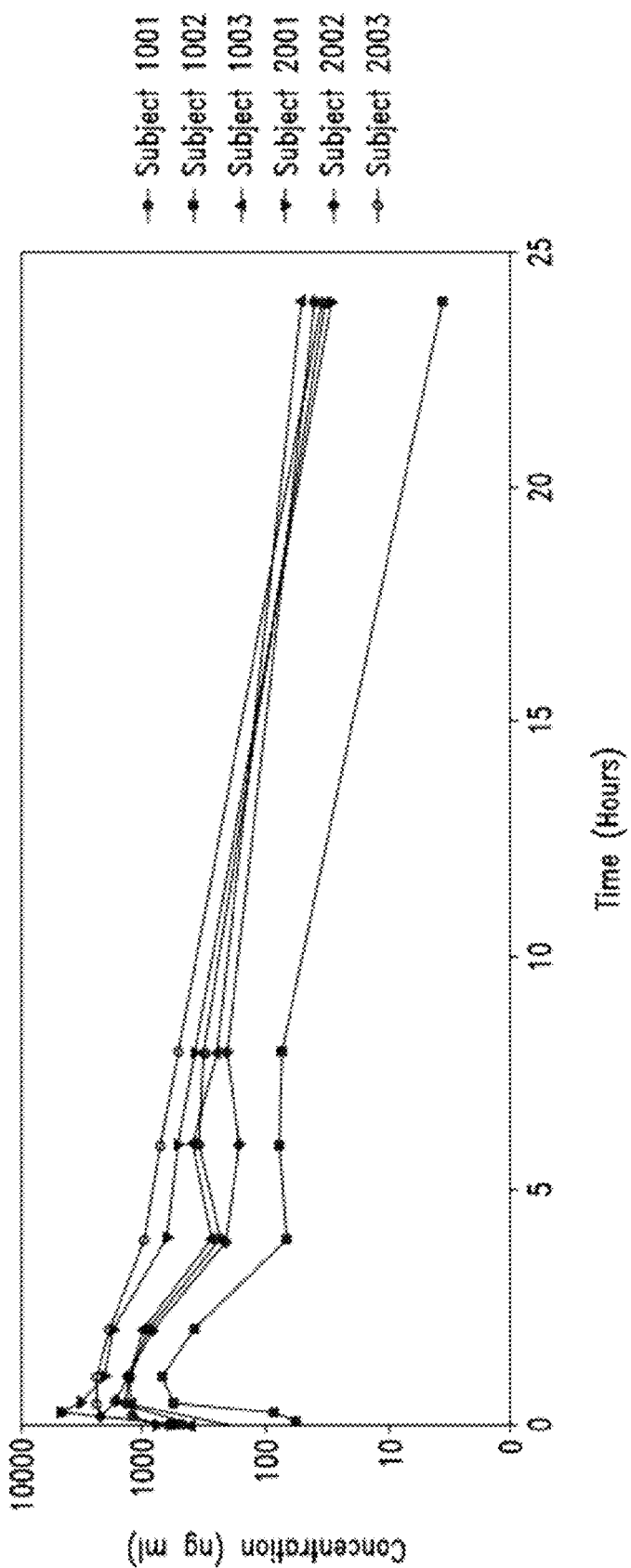
FIG. 13 shows the plasma concentration levels of (1R,2R)-2-[(3R)-hydroxypyrrolidinyl]-1-(3,4-dimethoxyphenethoxy)cyclohexane monohydrochloride after a single oral dose in six dog subjects following seven days of repeated (4×daily) dosing of the drug.

The concentration of drug in the plasma of the dogs on days 1 and 9 are given in the tables below, and shown graphically in FIGS. 12 and 13.

TABLE 17

Drug Assayed concentrating in dog plasma (ng/ml):

| Time (hrs.) | Dog 1001 | Dog 1002 | Dog 1003 | Dog 2001 | Dog 2002 | Dog 2003 |
|---|---|---|---|---|---|---|
| Day 1 (Concentration in ng/ml) | | | | | | |
| 0 | BQL | BQL | BQL | BQL | BQL | BQL |
| 0.083 | 102 | BQL | BQL | 14.5 | 10.3 | BQL |
| 0.25 | 683 | 4.27 | 5.58 | 844 | 861 | 291 |
| 0.5 | 739 | 397 | 128 | 1620 | 1190 | 1070 |
| 1 | 647 | 291 | 177 | 1430 | 651 | 979 |
| 2 | 266 | 135 | 284 | 777 | 301 | 586 |
| 4 | 71.3 | 32.7 | 68.2 | 203 | 92.4 | 210 |
| 6 | 43.9 | 15.3 | 27.5 | 95.7 | 72.4 | 104 |
| 8 | 36.3 | 10.9 | 22.0 | 74.7 | 64.7 | 60.3 |
| 24 | 2.45 | BQL | 1.15 | 9.58 | 10.5 | 3.54 |
| Day 9 (Concentration in ng/ml) | | | | | | |
| 0 | 342 | 95.9 | 277 | 515 | 206 | 526 |
| 0.083 | 367 | 61.2 | 268 | 590 | 229 | 681 |
| 0.25 | 1300 | 89.2 | 608 | 5150 | 2410 | 4660 |
| 0.5 | 1520 | 613 | 1370 | 3510 | 1840 | 2570 |
| 1 | 1430 | 742 | 1390 | 2220 | 1400 | 2560 |

TABLE 17-continued

Drug Assayed concentrating in dog plasma (ng/ml):

| Time (hrs.) | Dog 1001 | Dog 1002 | Dog 1003 | Dog 2001 | Dog 2002 | Dog 2003 |
|---|---|---|---|---|---|---|
| 2 | 1080 | 409 | 915 | 1920 | 885 | 1980 |
| 4 | 248 | 72.3 | 299 | 703 | 227 | 1070 |
| 6 | 372 | 84.8 | 423 | 566 | 179 | 770 |
| 8 | 340 | 79.4 | 274 | 416 | 226 | 558 |
| 24 | 37.7 | 3.72 | 53.9 | 29.9 | 41.4 | 36.1 |

** BQL—Below quantitation limit (1 ng/mL)

Further, the steady-state concentration of drug in blood plasma immediately before given another dose of drug is given below:

TABLE 18

Concentration of drug in dog plasma prior to dosing:

| Day | Time (hrs.) | Dog 1001 | Dog 1002 | Dog 1003 | Dog 2001 | Dog 2002 | Dog 2003 |
|---|---|---|---|---|---|---|---|
| 3 | 0 | 290 | 96.4 | 217 | 499 | 195 | 523 |
| 4 | 0 | 515 | 93.1 | 164 | 899 | 130 | 541 |
| 5 | 0 | 404 | 80.9 | 144 | 349 | 240 | 548 |
| 6 | 0 | 496 | 110 | 212 | 407 | 266 | 756 |
| 7 | 0 | 427 | 92.3 | 245 | 435 | 200 | 501 |
| 8 | 0 | 340 | 75.7 | 181 | 447 | 226 | 419 |

Figure 14:
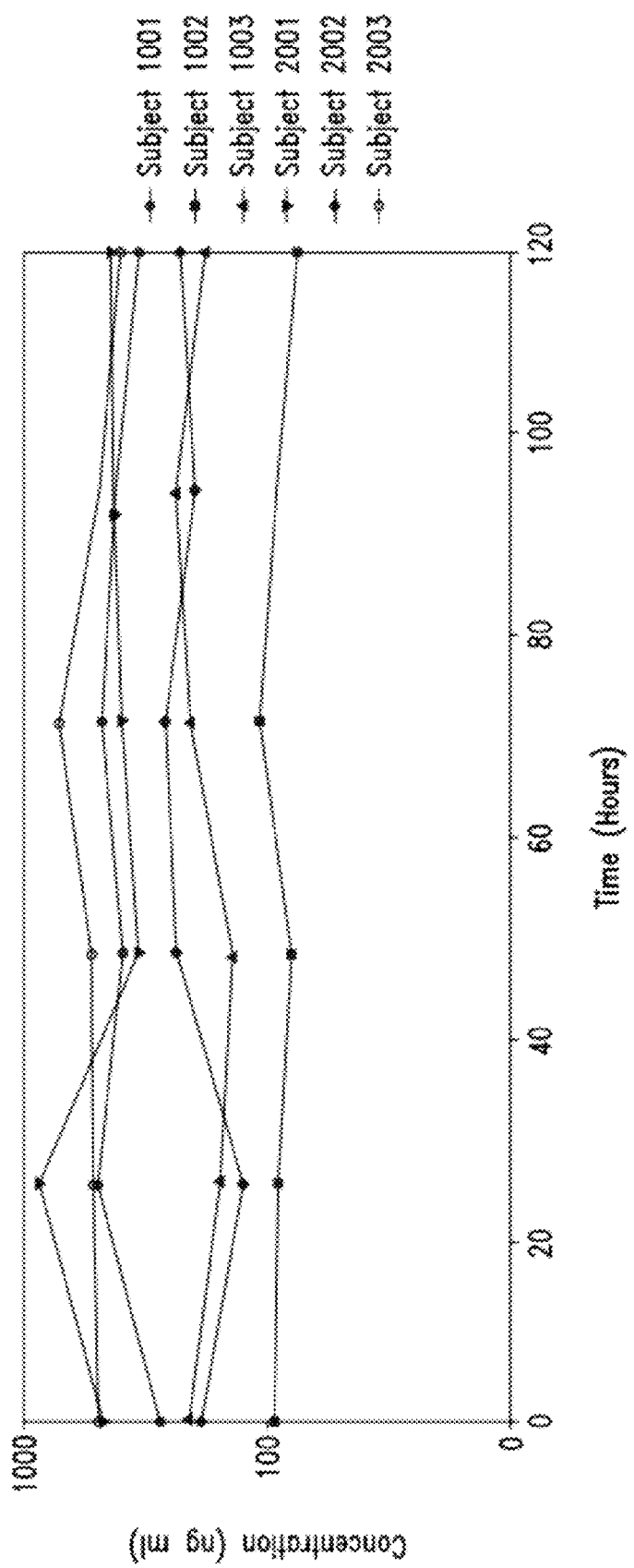
FIG. 14 shows the trough (Cmin) plasma concentration levels of (1R,2R)-2-[(3R)-hydroxypynolidinyl]-1-(3,4-dimethoxyphenethoxy)cyclohexane monohydrochloride for six dog subjects given repeated daily dosing of the drug.

By day 3, the plasma concentration has reached an approximate steady-state for all dogs within both dosing regimes. This data is graphed in FIG. 14 (note that the zero time in FIG. 14, is the time immediately before the first morning dosing on the third day of the study. Subsequent plasma levels were taken before each morning dose on days 4-8). FIG. 14 shows the steady-state trough (Cmin) values for each of the six dogs.

Example 5

Simulated Multiple Dosing Pharmacokinetics

This example describes a simulation of the pharmacokinetics of an ion channel modulating compound, particularly the pharmacokinetics of different multiple dosing regimes. This simulation is based on parameters extracted from experimental data defining the plasma levels of one example of an ion channel modulating compound as described herein.

The following parameters were estimated from the pharmacokinetics and bioavailability of (1R,2R)-2-[(3R)-hydroxypyrrolidinyl]-1-(3,4-dimethoxyphenethoxy)cyclohexane monohydrochloride in beagle dogs. A summary of the estimated parameters is presented in the table below:

TABLE 19

Estimated One-Compartment Model Parameters Modeled Oral Dog Data[a]

| Parameter | Dog 1 | Dog 2* | Dog 3 | Dog 4 | Average | Standard Deviation |
|---|---|---|---|---|---|---|
| Dose (mg/kg) | 20 | 20 | 20 | 20 | 20 | 0 |
| Cmax (ug/mL) | 3.7 | 2.7 | 3.8 | 2.9 | 3.3 | 0.6 |
| Tmax (min) | 15 | 15 | 15 | 15 | 15 | 0 |
| AUCinf (ug · min/mL) | 401 | 259 | 421 | 245 | 332 | 92 |
| F | 91% | 58 | 95 | 55 | 52 | 39 |
| Ka | 0.2 | 0.2 | 0.26 | 0.2 | 0.215 | 0.03 |
| Kel | 0.011002 | 0.012603 | 0.010345 | 0.014748 | 0.012175 | 0.00196 |
| t½ ab (min) | 3.5 | 3.5 | 2.7 | 3.5 | 3.3 | 0.4 |
| t½ el (min) | 63 | 55 | 67 | 47 | 58 | 9 |
| Vd (L/kg) | 4.1 | 3.6 | 4.4 | 3 | 3.8 | 0.6 |

*Used Tmax equal 15 instead of 30. Using Tmax = 30 causes Vd to be approximately 2.2 L/kg.
[a]One compartment model was found to adequately fit the data. There were not enough data points to justify a 2 compartment fit.

All parameters were fit using a one-compartment model, and were in good agreement across all four dogs. The parameters from Dog 3 were used in the remainder of this example to simulate the pharmacokinetics of (1R,2R)-2-[(3R)-hydroxypyrrolidinyl]-1-(3,4-dimethoxyphenethoxy)cyclohexane monohydrochloride.

Figure 15:
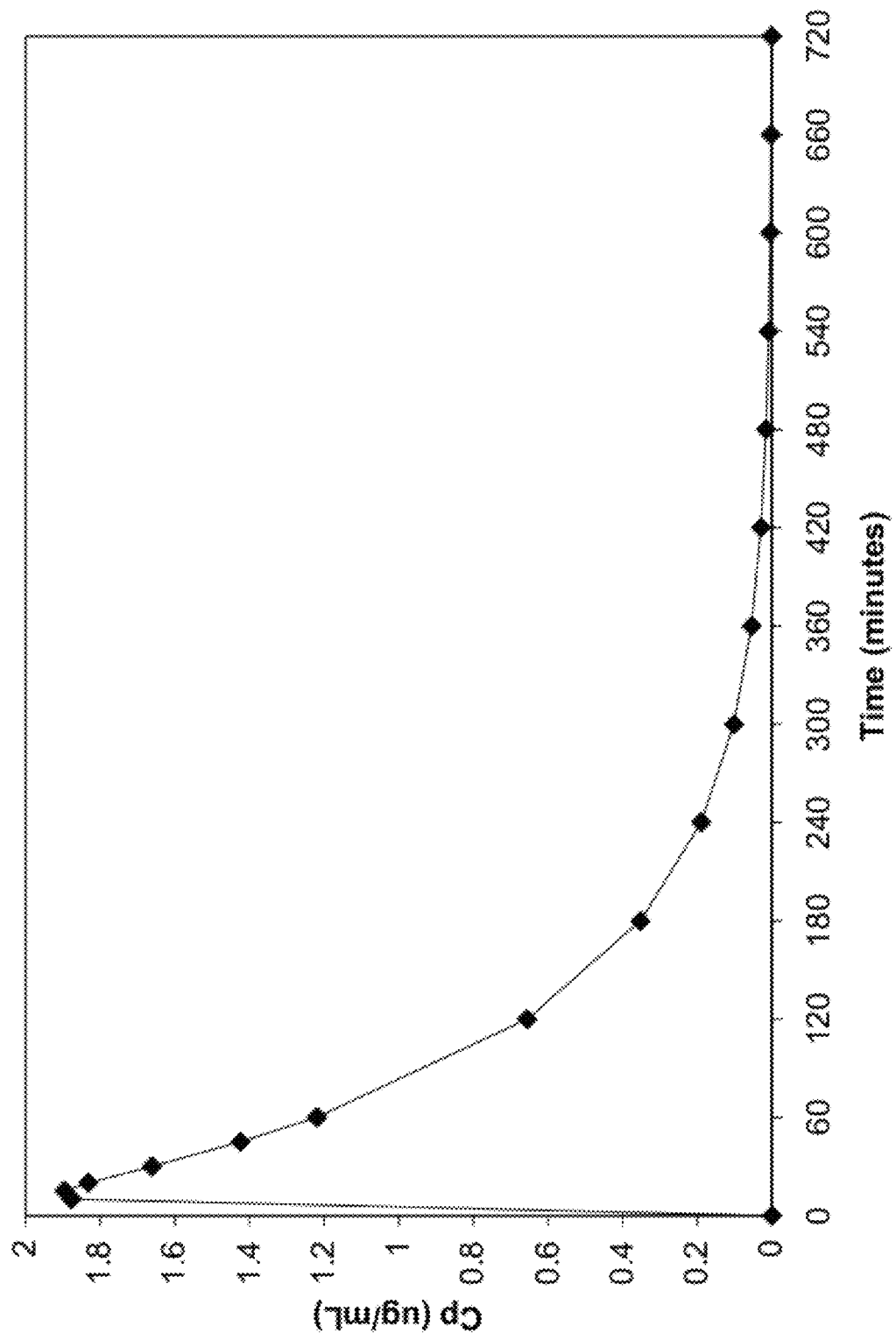
FIG. 15 shows a simulation of the pharmacokinetics of a 100 mg oral dose.

Using the parameters generated, the pharmacokinetics of a single oral (bolus) dose of 100 mg of the drug (approximately 10 mg/kg) may be calculated. FIG. 15 shows a simulation of this single oral dose. Because the data shown is simulated, the pharmacokinetic profile at any time following administration (t) may be determined. Simulation of this data was performed using known methods.

Figure 16:
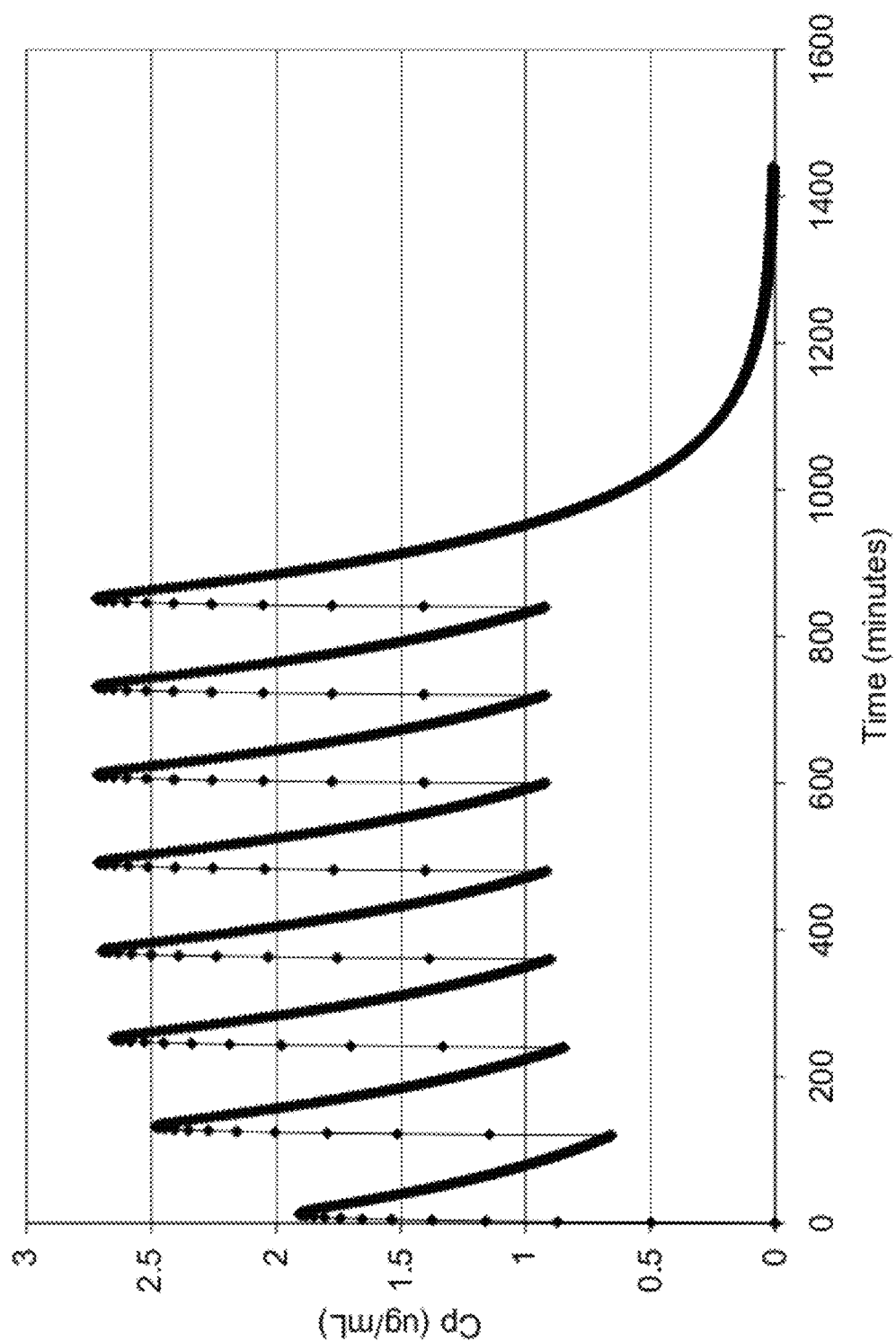
FIG. 16 shows a simulated pharmacokinetic profile for a multiple dosing regime of 100 mg given orally every two hours.

The pharmacokinetics (e.g. plasma concentrations over time) of multiple oral doses may also be simulated. FIG. 16 shows the blood plasma concentration ($C_p$ in μg/ml) for eight doses of 100 mg of drug administered every 2 hours. The steady-state trough ($C_{min}$) value is achieved by six hours (360 minutes). This trough value is approximately 0.92 μg/mL when the drug is given at a dose of 100 mg every 2 hours.

Figure 17:
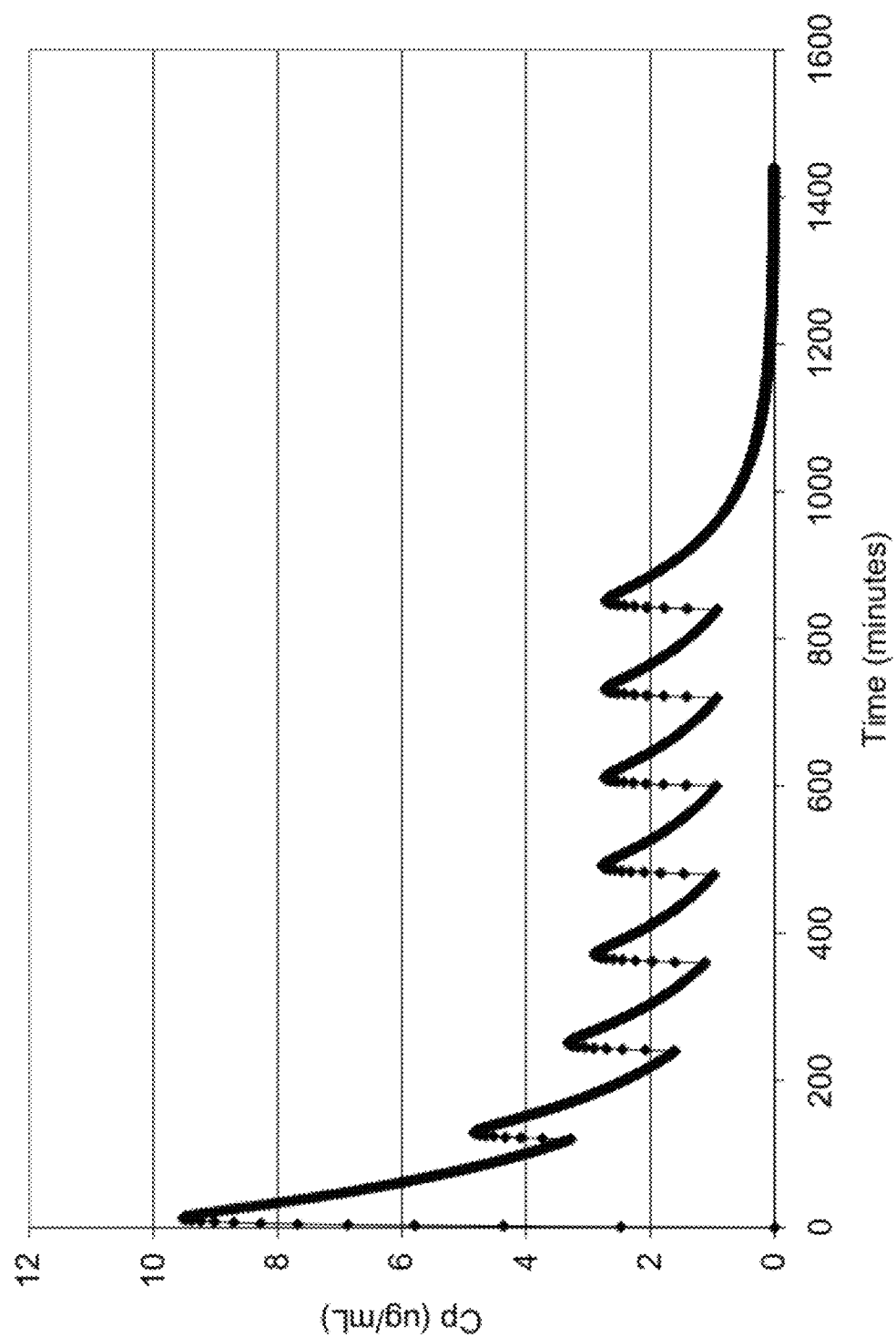
FIG. 17 shows a simulated pharmacokinetic profile for a multiple dosing regime of a loading dose of 500 mg followed by a maintenance dose of 100 mg given orally every two hours.

As described herein, dosing regimes may vary, including variations in the amount of drug given per dose, the method of dosing (formulation), and the time between doses. For example, a "loading dose" of 500 mg followed by several "maintenance" doses of 100 mg given every two hours is simulated in FIG. 17. The initial peak in blood plasma concentration ($C_{max}$) is followed by the saw-tooth pattern as the concentration of the drug achieves a trough. As before, the trough concentration ($C_{min}$) is approximately 0.92 μg/ml. FIG. 18 shows another example in which the loading dose (first dose) is 150 mg, followed by maintenance dose (subsequent doses) of 100 mg.

Drug formulation may also have dramatic effect on the pharmacokinetics of ion channel modulating compounds. For example, the release and continuous release formulations described above may be used to simulate plasma levels. The rate constant (dissolution rate constant) for an IR formulation, a 300 mg Hydrophilic formulation, a hydrophobic formulation, and a hot-melt wax formulation (see the Immediate Release and Controlled Release formulations section, above) were approximated by fitting measured data to a first-order dissolution model. These rate constants are shown in Table 20. As with all of the modeled parameters, approximations of the dissolution rate constants could be made using different methods, such as zero-order kinetics.

TABLE 20

First Order Dissolution Rate Constants for IR and CR Formulations

| Kd | Description |
|---|---|
| 0.111798 | IR |
| 0.005728 | Hydrophilic |
| 0.002366 | Hydrophilic (300 mg) |
| 0.01333 | Hydrophobic |
| 0.006189 | Hot-melt Wax |

Figure 19:
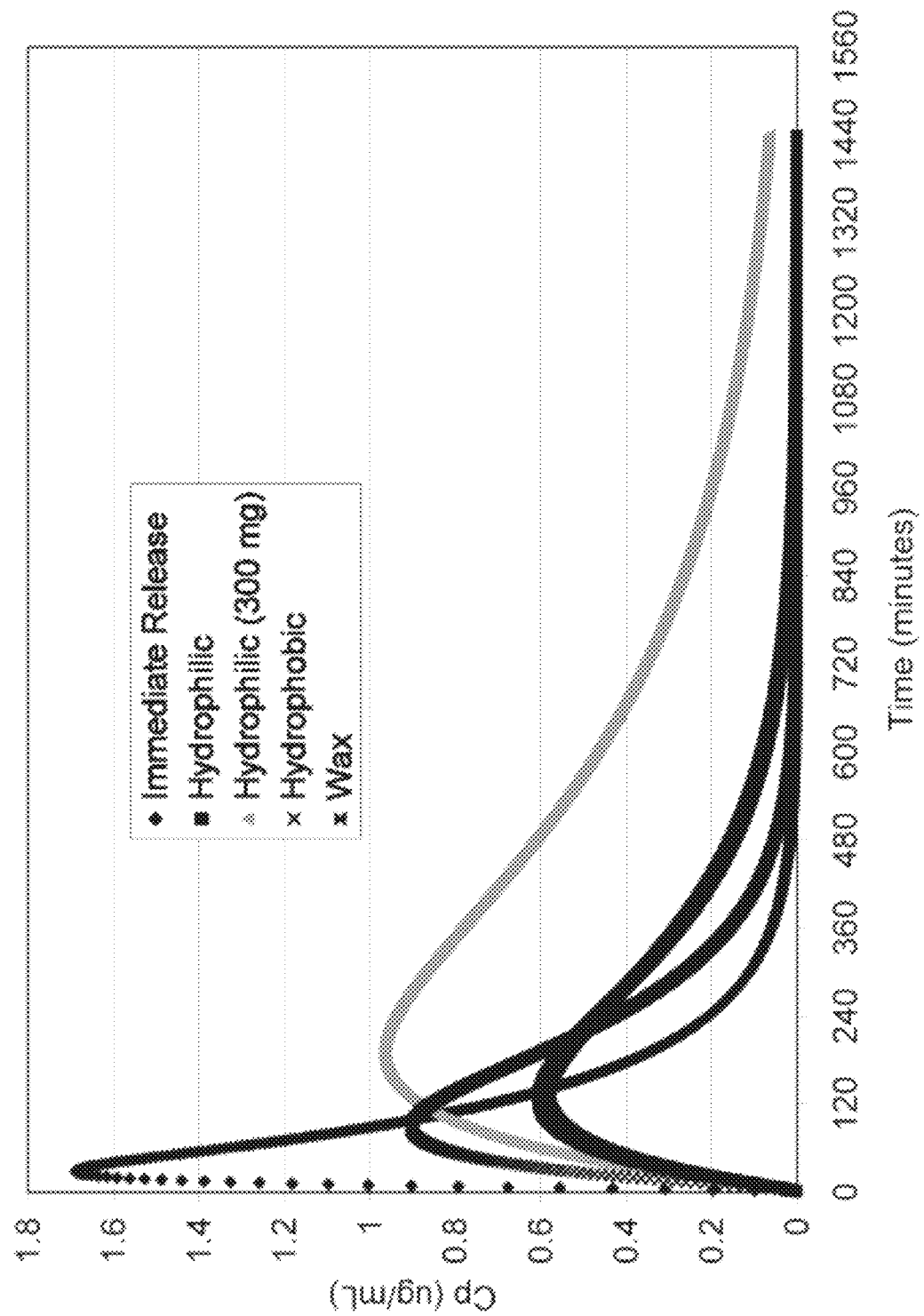
FIG. 19 shows a simulation of a single oral dose of an immediate release drug formulation, four controlled release formulations: a hydrophilic drug formulation, a 300 mg hydrophilic drug formulation, a hydrophobic drug formulation, and a hot-melt wax drug formulation.
Figure 20:
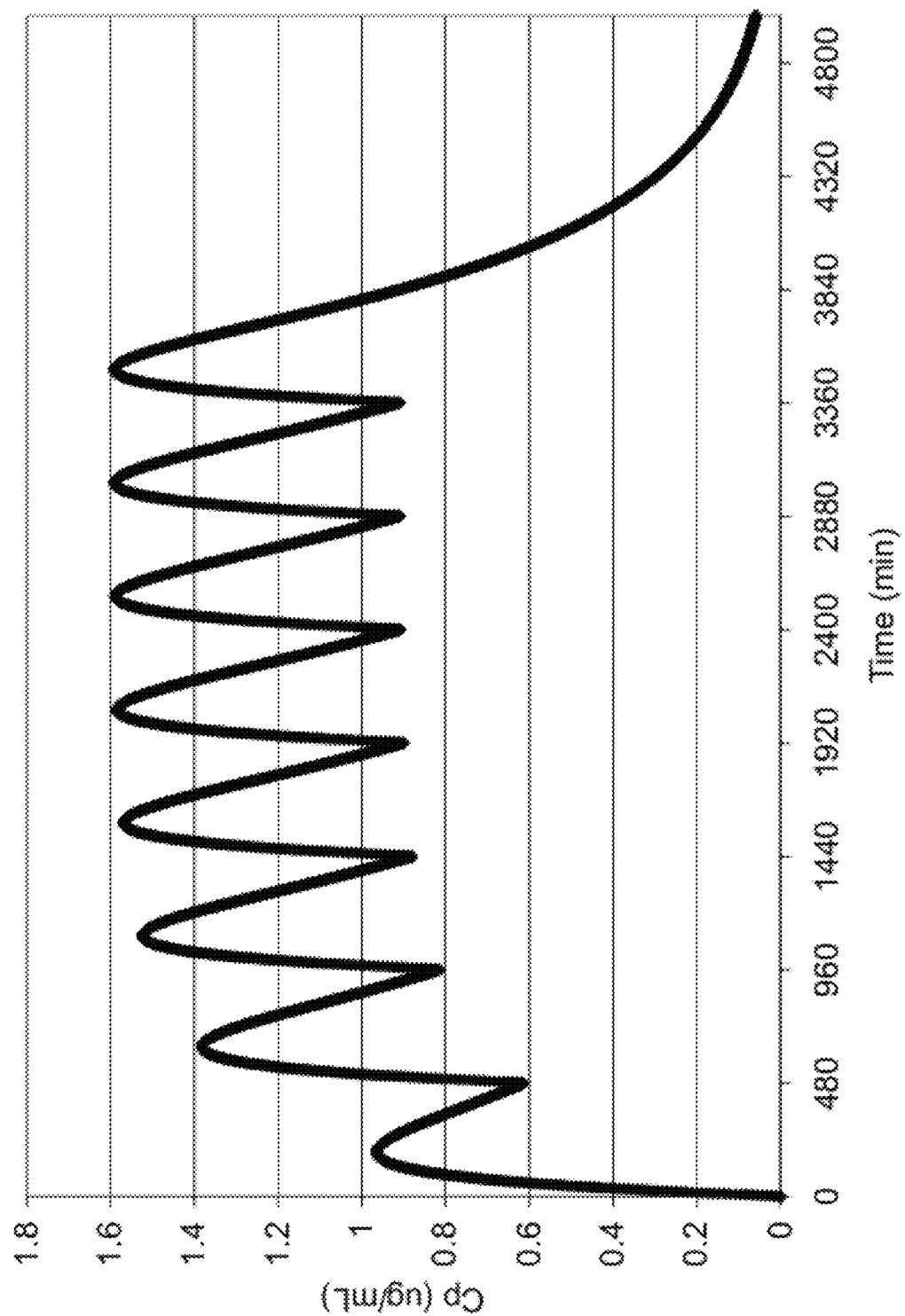
FIG. 20 shows a simulated pharmacokinetic profile for a multiple dosing regime of a a 300 mg hydrophilic drug formulation given orally every eight hours.
Figure 21:
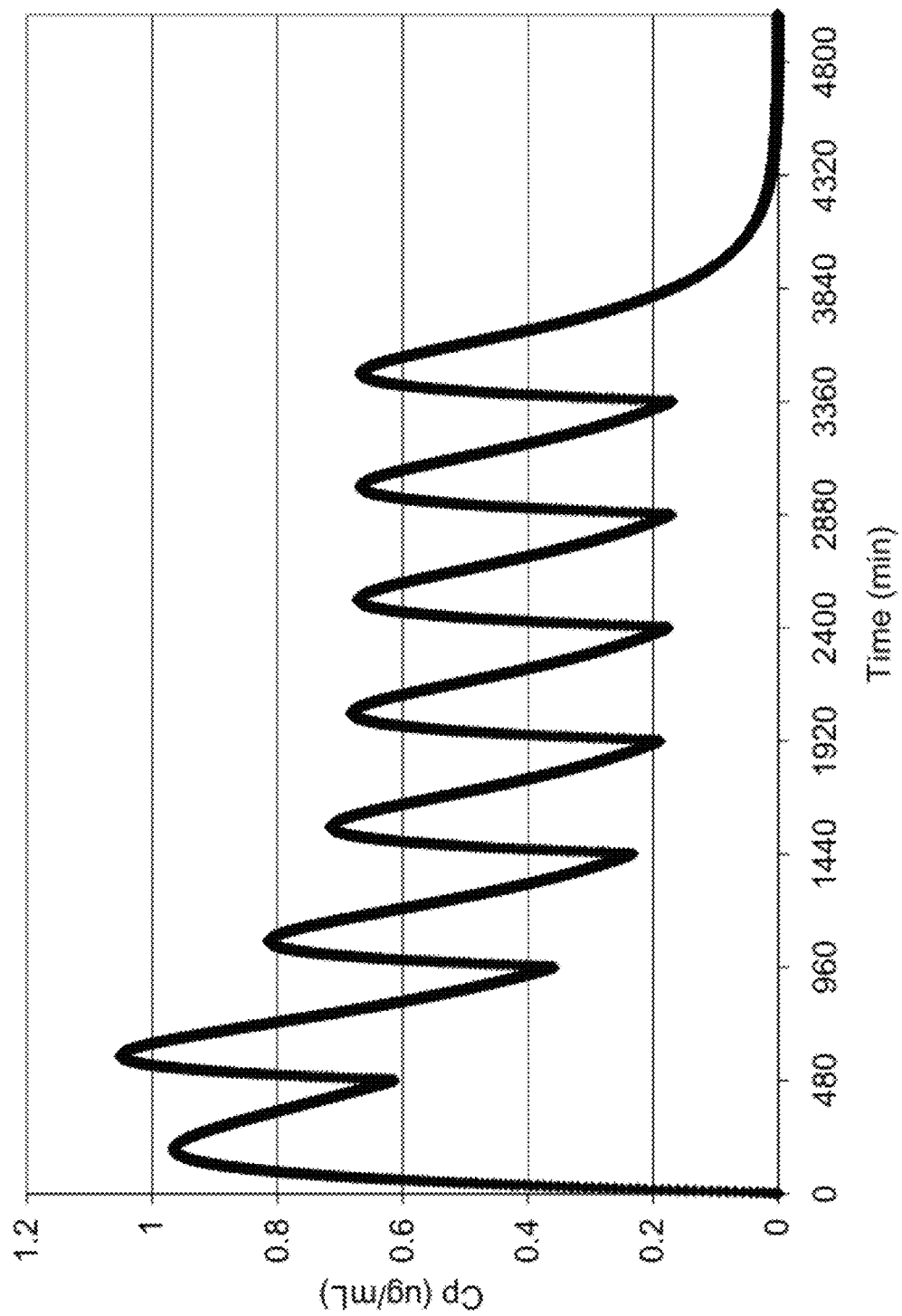
FIG. 21 shows a simulated pharmacokinetic profile for a multiple dosing regime in which a loading dose of a 300 mg hydrophilic drug formulation is followed by a maintenance dose of 100 mg given orally every eight hours.

FIG. 19 shows the pharmacokinetics of these formulations based on these dissolution rate constants for a single dose. A simulation of a multiple-dosing regime using a 300 mg hydrophilic CR tablet is shown in FIG. 20 where maintenance doses are given every eight hours. FIG. 21 shows the simulated blood plasma concentration for a loading dose of a 300 mg hydrophilic CR tablet followed by 7 doses of 100 mg every eight hours.

The simulations of pharmacokinetics described above are intended only to illustrate the methods, formulations and routes of administration described and claimed herein, and are not intended to limit the methods, formulations and routes of administration to any particular theory or embodiment.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treating a human subject undergoing arrhythmia, the method comprising administering to the subject an amount of an ion channel modulating compound in one or more intravenous doses of a formulation, wherein each dose of the formulation independently comprises an ion channel modulating compound of formula

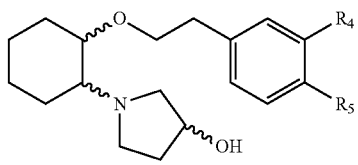

including isolated enantiomeric, diastereomeric and geometric isomers thereof and mixtures thereof, or a solvate or pharmaceutically acceptable salt thereof;
wherein $R_4$ and $R_5$ are independently selected from hydrogen, hydroxy and $C_1$-$C_6$alkoxy; and
wherein the amount of ion channel modulating compound administered to the subject produces in the blood plasma of the subject a total concentration of the ion channel modulating compound with a concentration of greater than about 0.1 µg/ml for some time.

2. The method of claim 1, wherein the total concentration of the ion channel modulating compound has a $C_{max}$ of greater than about 0.1 µg/ml.

3. The method of claim 2, wherein the total concentration of the ion channel modulating compound in the blood plasma of the subject has a $C_{max}$ of between about 0.3 µg/ml and about 20 µg/ml.

4. The method of claim 2, wherein the total concentration of the ion channel modulating compound in the blood plasma of the subject has a $C_{max}$ of between about 0.3 µg/ml and about 15 µg/ml.

5. The method of claim 1, wherein the total concentration of the ion channel modulating compound in the blood plasma of the subject is greater than 0.1 µg/ml for a period of time of at least about 10 hours.

6. The method of claim 1, wherein the total concentration of the ion channel modulating compound in the blood plasma of the subject is greater than 1.0 µg/ml for a period of time of at least about 2 hours.

7. The method of claim 1, wherein the ion channel modulating compound is administered in two or more doses.

8. The method of claim 1, wherein the method comprises administering to the subject one or two doses of the formulation, and wherein each dose of the formulation comprises a monohydrochloride salt of the formula

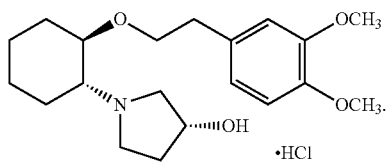

9. The method claim 1, wherein the formulation is an isotonic solution of the ion channel modulating compound.

10. The method of claim 2, wherein the arrhythmia is an atrial arrhythmia.

11. The method of claim 10, wherein the arrhythmia is an atrial fibrillation.

12. The method of claim 1, wherein the arrhythmia is selected from the group comprising ventricular tachycardia, ventricular fibrillation, premature ventricular contractions, supraventricular tachycardia, Wolff-Parkinson-White Syndrome, atrial fibrillation, and premature supraventricular contractions, or wherein the arrhythmia is associated with Long Q-T Syndrome or sick sinus syndrome.

13. A method of administering a therapeutically effective amount of an ion channel modulating compound of formula

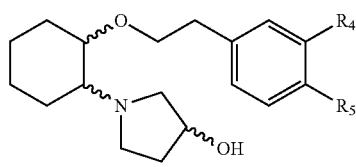

including isolated enantiomeric, diastereomeric and geometric isomers thereof and mixtures thereof, or a solvate or pharmaceutically acceptable salt thereof;
wherein $R_4$ and $R_5$ are independently selected from hydrogen, hydroxy and $C_1$-$C_6$alkoxy;
to a human subject for the treatment of arrhythmia, wherein the method comprises administering to the human subject a first dosage amount of between about 0.1 mg/kg and about 10 mg/kg of the ion channel modulating compound; and, after a time period sufficient to determine the therapeutic effectiveness of the first dosage amount, optionally administering a second dosage amount of between about 0.1 mg/kg and about 10 mg/kg of the ion channel modulating compound, which produces in the blood plasma of the human subject a total concentration of the ion channel modulating compound of greater than about 0.1 µg/ml for at least some time.

14. The method of claim 13, which produces a $C_{max}$ of the ion channel modulating compound in the blood plasma of the human subject of between about 0.3 µg/ml and about 20 µg/ml.

15. The method of claim 13, which produces a $C_{max}$ of the ion channel modulating compound in the blood plasma of the human subject of between about 0.3 µg/ml and about 15 µg/ml.

16. The method of claim 13, which produces a total concentration of the ion channel modulating compound in the blood plasma of the human subject greater than about 0.1 µg/ml for a period of time of at least about 10 hours.

17. The method of claim 13, which produces a total concentration of the ion channel modulating compound in the blood plasma of the human subject greater than about 0.1 µg/ml for a period of time of at least about 2 hours.

* * * * *